(12) United States Patent
Luster et al.

(10) Patent No.: US 6,673,915 B1
(45) Date of Patent: Jan. 6, 2004

(54) NUCLEIC ACID ENCODING MONOCYTE CHEMOTACTIC PROTEIN 4

(75) Inventors: Andrew D. Luster, Wellesley, MA (US); Eduardo A. Garcia-Zepeda, Somerville, MA (US); Mindy N. Sarafi, Jamaica Plains, MA (US)

(73) Assignee: General Hospital Corporation, Boston, MA (US)

( * ) Notice: Subject to any disclaimer, the term of this patent is extended or adjusted under 35 U.S.C. 154(b) by 0 days.

(21) Appl. No.: 09/545,894

(22) Filed: Apr. 7, 2000

Related U.S. Application Data

(63) Continuation of application No. 08/940,687, filed on Sep. 30, 1997, now abandoned.
(60) Provisional application No. 60/027,128, filed on Sep. 30, 1996.

(51) Int. Cl.[7] ............................ C12N 15/19; C12N 5/10; C12N 15/63; C07K 14/52
(52) U.S. Cl. .................... 536/23.5; 435/71.1; 435/71.2; 435/320.1; 435/325; 435/252.3; 435/254.11; 435/471; 530/324
(58) Field of Search .............................. 536/23.1, 23.5; 435/69.5, 71.1, 71.2, 471, 320.1, 325, 252.3, 254.11; 530/324

(56) References Cited

U.S. PATENT DOCUMENTS

| | | | |
|---|---|---|---|
| 5,179,078 A | 1/1993 | Rollins et al. | 514/2 |
| 5,413,778 A | 5/1995 | Kunkel et al. | 424/1.41 |
| 5,459,128 A | 10/1995 | Rollins et al. | 514/8 |
| 5,981,230 A | * 11/1999 | Li et al. | 435/69.5 |

FOREIGN PATENT DOCUMENTS

| | | |
|---|---|---|
| DE | 4125251 | 9/1992 |
| JP | 04-45796 | 2/1992 |
| JP | 05-271093 | 10/1993 |
| JP | 07-089866 | 4/1995 |
| WO | WO 90/08777 | 8/1990 |
| WO | WO 95/07985 | 3/1995 |
| WO | WO 95/13295 | 5/1995 |
| WO | WO 95/19167 | 7/1995 |
| WO | WO 95/19436 | 7/1995 |
| WO | WO 96/05856 | 2/1996 |
| WO | WO 97/31098 | 8/1997 |

OTHER PUBLICATIONS

Allavena et al., "Induction of natural killer cellmigration by monocyte chemotactic protein–1,–2 and –3", Eur. J. Immunol., 24:3233–3236, (1994).

Bischoff et al., "Monocyte chemotactic protein 1 is a potent activator of human basophils", J. of Exp. Med., 175:1271–1275, (1992).

Cook et al., "Requirement of MI–1α for an inflammatory response to viral infection", Science, 269:1583–1585, (1995).

Cunningham et al., Science 244:1081–1085 (1989).

George et al., "Macromolecules Sequencing and Synthesis", Chapter 12, pp. 127–149, Alan R. Liss, Inc. NY (1998).

Gong et al., "Antagonists of monocyte chemoattractant protein 1 identified by modification of functionally critical NH2–terminal residues", J. of Exp. Med., 181:631–640, (1995).

Huffinagle et al., "The role of monocyte chemotactic protein–1 (MCP–1) in the recruitment of monocytes and CD4+ T cells during a pulmonary *Cryptococcus neoformans* infection", J. Immunol., 155:4790–4797, (1995).

Luo et al., "Biologic activities of the murine β–chemokine TCA3", J. Immunol., 153:4616–4624, (1994).

Loetscher et al., "Monocyte chemotactic proteins MCP–1, MCP–2, and MCP–3 are major attractants for human CD4+ and CD8+ T lymphocytes", The FASEB J., 8:1055–1060, (1994).

Luster et al., IP–10, A–C–X–C– chemokine, elicits a potent thymus–dependent antitumor response in vivo., J. of Exp. Med., 178:1057–1065, (1993).

Nakano et al., "Protection against lethal bacterial infection in mice by monocyte–chemotactic and—activating factor", Infection and Immunity, 62",:377–383, (1994).

Rollins et al., "Suppression of tumor formation in vivo by expression of the JE gene in malignant cells", Molecular and Cellular Biology, 11:3125–3131, (1991).

Sekido et al., "Prevention of lung reperfusion injury in rabbits by a monoclonal antibody against interleukin–8", Nature, 365:654–657, (1994).

Sharpe et al., "Growth inhibition of murine melanoma and human colon carcinoma by recombinant human platelet factor 4", J. of the Nat'l Cancer Inst., 82:848–853, (1990).

Uguccioni et al., "Actions of the chemotactic cytokines MCP–1, MCP–2, MCP–3, RANTES, MIP–1α and MIP–1β on human monocytes", Eur. J. Immunol., 25:64–68, (1995).

Uguccioni et al., "Monocyte chemotactic Protein 4 (MCP–4), a novel structural and functional analogue of MCP–3 and eotaxin", J. Exp. Med., 183:2379–2384, (1996).

* cited by examiner

*Primary Examiner*—Prema Mertz
(74) *Attorney, Agent, or Firm*—Clark & Elbing LLP; Kristina Bieker-Brady

(57) ABSTRACT

Substantially pure nucleic acid molecules encoding the monocyte chemotactic proteins MCP-4 and MCP-5. These molecules and the polypeptides they encode are useful in treating diseases or conditions that: (1) are exacerbated by a local immune response, (2) would benefit from a local immune response, or (3) are caused by infectious agents that gain entry to mammalian cells via the chemokine receptors bound by MCP-4 or MCP-5.

4 Claims, 40 Drawing Sheets

```
                                                          -23
                                         SEQ ID NO: 2  Met Lys Val Ser Ala Val Leu
                                                       --- --- --- --- --- --- ---
SEQ ID NO: 1 aacattgtgaaatctccaactcttaaccttcaac ATG AAA GTC TCT GCA GTG CTT  55
                                                                     ↓ +1
Leu Cys Leu Leu Leu Met Thr Ala Ala Phe Asn Pro Gln Gly Leu Ala Gln Pro
--- --- --- --- --- --- --- --- --- --- --- --- --- --- --- --- --- ---
CTG TGC CTG CTG CTC ATG ACA GCA GCT TTC AAC CCC CAG GGA CTT GCT CAG CCA 109

Asp Ala Leu Asn Val Pro Ser Thr Cys Cys Phe Thr Phe Ser Ser Lys Lys Ile
--- --- --- --- --- --- --- --- --- --- --- --- --- --- --- --- --- ---
GAT GCA CTC AAC GTC CCA TCT ACT TGC TGC TTC ACA TTT AGC AGT AAG AAG ATC 163

Ser Leu Gln Arg Leu Lys Ser Tyr Val Ile Thr Thr Ser Arg Cys Pro Gln Lys
--- --- --- --- --- --- --- --- --- --- --- --- --- --- --- --- --- ---
TCC TTG CAG AGG CTG AAG AGC TAT GTG ATC ACC ACC AGC AGG TGT CCC CAG AAG 217

Ala Val Ile Phe Arg Thr Lys Leu Gly Lys Glu Ile Cys Ala Asp Pro Lys Glu
--- --- --- --- --- --- --- --- --- --- --- --- --- --- --- --- --- ---
GCT GTC ATC TTC AGA ACC AAA CTG GGC AAG GAG ATC TGT GCT GAC CCA AAG GAG 271

Lys Trp Val Gln Asn Tyr Met Lys His Leu Gly Arg Lys Ala His Thr Leu Lys
--- --- --- --- --- --- --- --- --- --- --- --- --- --- --- --- --- ---
AAG TGG GTC CAG AAT TAT ATG AAA CAC CTG GGC CGG AAA GCT CAC ACC CTG AAG 325
+75
Thr ***
--- ---
ACT TGA  actctgctaccccctactgaaatcaagctggagtacgtgaaatgacttttccattctcctctg 393
gcctcctcttctatgctttggaatacttctaccataatttttcaaataggatgcattcggttttgtgattca
aaatgtactatgtgttaagtaatattggctattatttgacttgttgctggtttggagttttatttgagtatt 535
gctgatctttctaaagcaaggccttgagcaagtaggttgctgtctctaagccccttcccttccactatg
agctgctggcagtgggtttgtattcggttcccaggggttgagagcatgcctgtgggagtcatggacatgaa 677
gggatgctgcaatgtaggaaggagagctctttgtgaatgtgaggtgttgctaaatatgttattgtggaaag
atgaatgcaatagtaggactgctgacattttgcagaaaatacattttatttaaaatctcctaaaaaaaaa 819
aaaa
```

Fig. 1A

```
                                                       -22
SEQ ID NO: 4  Met Lys Ile Ser Thr Leu Leu Cys
              --- --- --- --- --- --- --- ---
SEQ ID NO:3 ctagctttcatttgaagtcttgacctcaac ATG AAG ATT TCC ACA CTT CTA TGC  56
                                                            +1
                                                            ▶ Gly Pro Asp Ala
Leu Leu Leu Ile Ala Thr Thr Ile Ser Pro Gln Val Leu Ala Gly Pro Asp Ala
--- --- --- --- --- --- --- --- --- --- --- --- --- --- --- --- --- ---
CTC CTG CTC ATA GCT ACC ACC ATC AGT CCT CAG GTA TTG GCT GGA CCA GAT GCG  110

Val Ser Thr Pro Val Thr Cys Cys Tyr Asn Val Val Lys Gln Lys Ile His Val
--- --- --- --- --- --- --- --- --- --- --- --- --- --- --- --- --- ---
GTG AGC ACC CCA GTC ACG TGC TGT TAT AAT GTT GTT AAG CAG AAG ATT CAC GTC  164

Arg Lys Leu Lys Ser Tyr Arg Arg Ile Thr Ser Ser Gln Cys Pro Arg Glu Ala
--- --- --- --- --- --- --- --- --- --- --- --- --- --- --- --- --- ---
CGG AAG CTG AAG AGC TAC AGG AGA ATC ACA AGC AGC CAG TGT CCC CGG GAA GCT  206

Val Ile Phe Arg Thr Ile Leu Asp Lys Glu Ile Cys Ala Asp Pro Lys Glu Lys
▶ --- --- --- --- --- --- --- --- --- --- --- --- --- --- --- --- ---
GTG ATC TTC AGG ACC ATA CTG GAT AAG GAG ATC TGT GCT GAC CCC AAG GAG AAG  272

Trp Val Lys Asn Ser Ile Asn His Leu Asp Lys Thr Ser Gln Thr Phe Ile Leu
--- --- --- --- --- --- --- --- --- --- --- --- --- --- --- --- --- ---
TGG GTT AAG AAT TCC ATA AAC CAC TTG GAT AAG ACG TCT CAA ACC TTC ATC CTT  326

Glu Pro Ser Cys Leu Gly ***
--- --- --- --- --- --- ---
         +82
GAA CCT TCA TGT CTA GGC TGA gagttccaaaaactcttacgtatttcccctgaagttccccac  390
gggcagtgtgatatttattatgatatctaaaagagatgtttttaataatttaaacaaacttgcttaaata
atatttaatggtattaagtaatatttgggccaattaaccgaatctaattt(a)₂₂                514
```

Fig. 1B

SEQ ID NO:2 Hu MCP4    MKVSAVLLCLLLMTAAFNPQGLAQPDALNVPSTCCFTFSSKKISLQRLKSYVITTSR-CPQKAVIFRTKLGKEICADPKEKWVQNYMKHLGRKAHTLKT
SEQ ID NO:5 Hu MCP1    MKVSAALLCLLLIAATFIPQGLAQPDAINAPVTCCYNFTNRKISVQRLASYRRITSSKCPKEAVIFKTIVAKEICADPKQKWVQDSMDHLDKQTQTPKT
SEQ ID NO:6 Hu MCP2    ------------AQPDSVSIPITCCFNVINRKIPIQRLESYTRITNIQCPKEAVIFKTKRGKEVCADPKERWVRDSMKHLDQIFQNLKP
SEQ ID NO:7 Hu MCP3    MKASAALLCLLLTAAAFSPQGLAQPVGINTSTCCYRFINKKIPKQRLESYRRTTSSHCPREAVIFKTKLDKEICADPTQKWVQDFMKHLDKKTQTPKL
SEQ ID NO:8 Hu EOT     MKVSAALIWLLLIAAAFSPQGLAGPASV--PTTCCFNLANRKIPLQRLESYRRITSGKCPQKAVIFKTKLAKDICADPKKKWVQDSMKYLDQKSPTPKP
SEQ ID NO:9 Hu MIP1 alpha MQVSTAALAVLLCTMALCNQVLSAPLAADTPTACCFSYTSRQIPQNFIADY-FETSSQCSKPSVIFLTKRGRQVCADPSEEWVQKYVSDLELSA
SEQ ID NO:10 Hu MIP1 beta MKLCVTVLSLLMLVAAFCSPALSAPMGSDPPTACCFSYTARKLPRNFVVDY-YETSSLCSQPAVVQTKRSKQVCADPSESWVQEYVYDLELN
SEQ ID NO:11 Hu RANTES MKVSAARLAVILIATALCAPASASPYSSDTTP-CCFAYIARPLPRAHIKEY-FYTSGKCSNPAVVFVTRKNRQVCANPEKKWVMS
SEQ ID NO:12 Mu MCP1   MQVPVMLLGLLFTVAGWSIHVLAQPDAVNAPLTCCYSFTSKMIPMSRLESYKRITSSRCPKEAVVFVTKLKREVCADPKKEWVQTYIKNLDRNQMRSEP>>>
SEQ ID NO:13 Mu MCP3   MRISATLLCLLLIAAAFSIQVWAQPDG-PNASTCCYVKK-QKIPKRNLKSYRRITSSRCPWEAVIFKTKKGMEVCAEAHQKWVEEAIAYLDMKTPTPKP
SEQ ID NO:14 Mu EOT    MQSSTALLFLLLTVTSFTSGVLAHPGSI--PTSCCFIMTSKKIPNTLLKSYKRITNNRCTLKAIVFKTRLGKEICADPKKKWVQDATKHLDQKLQTPKP

Fig. 2A

```
          -23                                        +1                    +10
mMCP-5    M K I S T - L L C L L L I A T T I S P Q V L A G P D A V S T P V T
mJE       M Q V P V M L L G L L F T V A G W S I H V L A Q P D A V N A P L T
mFIC      M R I S A T L L C L L L I A A A F S I Q V W A Q P D G P N A S - T
mEotaxin  M Q S S T A L L F L L L T V T S F T S Q V L A H P G S I - - P T S
hMCP-1    M K V S A A L L C L L L I A A T F I P Q G L A Q P D A I N A P V T
hMCP-2    - - - - - - - - - - - - - - - - - - - - - A Q P D S V S I P I T
hMCP-3    M K A S A A L L C L L L T A A A F S P Q G L A Q P V G I N T S T T
hMCP-4    M K V S A V L L C L L L M T A A F N P Q G L A Q P D A L N V P S T
hEotaxin  M K V S A A L L W L L L I A A A F S P Q G L A G P A S V - - P T T +11                                                        +43
mMCP-5    C C Y N V V K Q K I H V R K L K S Y R R I T S S Q C P R E A V I F
mJE       C C Y S F T S K M I P M S R L E S Y K R I T S S R C P K E A V V F
mFIC      C C Y - V K K Q K I P K R N L K S Y R R I T S S R C P W E A V I F
mEotaxin  C C F I M T S K K I P N T L K S Y K R I T N N R C T L K A I V F
hMCP-1    C C Y N F T N R K I S V Q R L A S Y R R I T S S K C P K E A V I F
hMCP-2    C C F N V I N R K I P I Q R L E S Y T R I T N I Q C P K E A V I F
hMCP-3    C C Y R F I N K K I P K Q R L E S Y R R T S S H C P R E A V I F
hMCP-4    C C F T F S S K K I S L Q R L K S Y - V I T T S R C P Q K A V I F
hEotaxin  C C F N L A N R K I P L Q R L E S Y R R I T S G K C P Q K A V I F +44                                                        +78
mMCP-5    R T I L D K E I C A D P K E K W V K N S I N H L D K T S Q T F I L
mJE       V T K L K R E V C A D P K K E W V Q T Y I K N L D R N Q M R S E P
mFIC      K T K K G M E V C A E A H Q K W V E E A I A Y L D M K T P T P K P
mEotaxin  K T R L G K E I C A D P K K K W V Q D A T K H L D Q K L Q T P K P
hMCP-1    K T I V A K E I C A D P K Q K W V Q D S M D H L D K Q T Q T P K T
hMCP-2    K T K R G K E V C A D P K E R +77                                                        +109
mMCP-5    E P S C L G
mJE       T T L F K T A S A L R S S A P L N V K L T R K S E A N A S T T F S
mFIC
mEotaxin
hMCP-1
hMCP-2
hMCP-3
hMCP-4
hEotaxin +110            +125
mJE       T T T S S T S V G V T S V T V N
```

Fig. 2B

NUCLEIC ACID ENCODING MONOCYTE CHEMOTACTIC PROTEIN 4

This application is a continuation of and claims priority from U.S. patent application Ser. No. 08/940,687, filed Sep. 30, 1997, now abandoned which claims priority from U.S. provisional application No. 60/027,128, filed Sep. 30, 1996.

BACKGROUND OF THE INVENTION

The invention relates to novel chemoattractants.

Six different types of white blood cells (leukocytes) are typically found in the blood. These are neutrophils, eosinophils, basophils, monocytes, lymphocytes, and plasma cells. The neutrophils and monocytes are primarily responsible for attacking and destroying invading bacteria, viruses, and other harmful agents. Neutrophils circulate within the bloodstream as mature, functional cells. Monocytes, however, circulate as immature cells that have a limited ability to fight infectious agents. It is only when monocytes are stimulated by chemotactic agents to move through the capillary wall into surrounding tissue that they become fully active. Once monocytes enter the tissues they begin to swell and many lysosomes and mitochondria appear in their cytoplasm. At this point, monocytes become called macrophages, which are extremely effective phagocytes. Each macrophage can engulf as many as 100 bacterial cells, as well as large particles, including whole red blood cells, malarial parasites, and necrotic tissue.

Chemokines are chemotactic cytokines that contribute to various immune and inflammatory responses by regulating the movement of selected blood-borne leukocytes into the tissues (Baggiolini et al., Adv. Immunol. 55:97–179, 1994; Oppenheim et al., Ann. Rev. Immunol. 9:617–648, 1991). All known chemokines have been assigned to one of three families on the basis of the chromosomal location of the genes that encode them and on the motif formed by conserved cysteine residues in the mature proteins. Two of these families, designated α and β, have many members, all of which have four conserved cysteine residues. The first two cysteines of α chemokines are separated by a single amino acid (CXC motif), and these proteins are encoded by genes clustered on human chromosome 4. In contrast, the first two cysteines of all β family chemokines are adjacent to one another (CC motif), and these proteins are encoded by genes clustered on human chromosome 17.

Chemokines having the CXC motif (α chemokines) primarily affect neutrophils and lymphocytes, and they can modulate angiogenesis. Chemokines having the CC motif (β chemokines) affect monocytes, lymphocytes, eosinophils, and basophils with variable selectivity. In addition, certain chemokines in the α and β family can inhibit HIV replication in T cells and monocytes, respectively.

The third chemokine family currently has only one member: the T cell-specific chemoattractant, lymphotactin (Kelner et al., Science 266:1395–1399, 1994). The gene encoding lymphotactin is located on human chromosome 1, and the protein sequence contains only the second and fourth cysteines found in the α and β chemokine families (Kennedy et al., J. Immunol. 155:203–209, 1995).

The monocyte chemoattractant proteins (MCPs), which constitute a subfamily of the β chemokines described above, include the three human MCP proteins (MCP-1, MCP-2, and MCP-3). These proteins are ~65% identical, and all have Gln as their N-terminal amino acid (Van Damme et al., J. Exp. Med. 176:59–65, 1992; Yoshimura et al., J. Exp. Med. 169:1449–1459, 1989).

The chemokine eotaxin is also a β chemokine. It is related in sequence to the MCP proteins, but does not contain an amino-terminal Gln residue. Eotaxin appears to be unique among the chemokines in that it causes the selective infiltration of eosinophils when injected subcutaneously and when administered directly to the lungs of naive guinea pigs.

Five genes encoding human β chemokine receptors, referred to as CKR1 through CKR5, have been cloned. (Charo et al., Proc. Natl. Acad. Sci. USA 91:2752–2756, 1994; Combadiere et al., DNA and Cell Biol. 14:673–380, 1995; Combadiere et al., J. Leukocyte Biol. in press, 1996; Gao et al., J. Exp. Med. 177:1421–1427, 1993; Neote et al., Cell 72:415–425, 1993; Power et al., J. Biol. Chem. 270:19495–19500, 1995; Samson et al., Biochem. 35:3362–3367, 1996). CKR2a and CKR2b are splice variants of the same gene. These receptors are not ubiquitously expressed: CKR1, CKR4, and CKR5 appear to be widely expressed on leukocytes, while expression of CKR2 and CKR3 is mainly restricted to monocytes and eosinophils, respectively.

SUMMARY OF THE INVENTION

The invention features substantially pure nucleic acid molecules that encode MCP-4 and MCP-5, two novel members of the β-chemokine family. The invention also includes polypeptides encoded by these nucleic acid molecules.

The nucleic acid molecules may consist of genomic DNA, cDNA, or mRNA, and, due to the degenerate nature of the genetic code, may vary in sequence provided that the encoded polypeptides are MCP-4 or MCP-5, as shown, for example, in FIGS. 1A and 1B, respectively.

Substantially pure MCP-4 and MCP-5 polypeptides, biologically active fragments of these polypeptides, including immunogenic fragments, are also considered within the scope of the invention. The biological activity of any given fragment of MCP-4 or MCP-5 may be readily determined by conducting an assay of, e.g., monocyte chemotaxis, as described herein. The preferred polypeptides of the invention are both substantially homologous to MCP-4 or MCP-5 and retain the biological activity of the relevant polypeptide, as described herein.

The nucleic acid molecules can encode a mammalian MCP-4 or MCP-5 polypeptide, such as those from a human, mouse, rat, guinea pig, cow, sheep, horse, pig, rabbit, monkey, dog, or cat. Preferably, the nucleic acid molecule encoding MCP-4 encodes human MCP-4 and the nucleic acid molecule encoding MCP-5 encodes murine MCP-5 or, more preferably, human MCP-5.

The nucleic acid molecules can be placed under the control of a promoter, which may be constitutively active or induced by one or more external agents. The promoter can provide the means to achieve tissue-specific or cell type-specific expression of the nucleic acid molecules of the invention. Alternatively, or in addition, the nucleic acid molecules can be operably linked to a DNA regulatory sequence. Skilled artisans will recognize that the nucleic acid molecules can be placed into a vector construct, such as a plasmid or viral vector, which may in turn be used to transduce living cells with the nucleic acid molecules of the invention. Cells can be transfected with plasmid vectors by standard methods including, but not limited to, liposome-, polybrene-, or DEAE dextran-mediated transfection (see, e.g., Feigner et al., Proc. Natl. Acad. Sci. USA 84:7413, 1987; Ono et al., Neurosci. Lett. 117:259, 1990; Brigham et al., Am. J. Med. Sci. 298:278, 1989), electroporation (Neumann et al., EMBO J. 7:841, 1980), calcium phosphate precipitation (Graham et al., Virology 52:456, 1973; Wigler et al., Cell 14:725, 1978; Felgner et al., supra) microinjection (Wolff et al., Science 247:1465, 1990), or velocity driven microprojectiles ("biolistics"). Viruses known to be useful for gene transfer include adenoviruses, adeno associated virus, herpes virus, mumps virus, poliovirus, retroviruses, Sindbis virus, and vaccinia virus such as canary pox virus.

The nucleic acid constructs described above are useful in a variety of ways. For example, the constructs may be used as a source of recombinantly produced MCP-4 or MCP-5 polypeptides. Alternatively, the constructs may be administered themselves in a therapeutic approach, as described below. In addition, the constructs may be used to generate transgenic animals that overexpress, or fail to express, MCP-4 or MCP-5. The animal can be a mouse, a worm, or any other animal considered useful for research or drug development. Transgenesis has become routine in the art of molecular biology.

MCP-4 or MCP-5 polypeptides expressed by transfected cells can be purified and injected into an animal, such as a rabbit, in order to generate polyclonal antibodies that specifically bind MCP-4 or MCP-5. Monoclonal antibodies may also be prepared using standard hybridoma technology (see, e.g., Kohler et al., Nature 256:495, 1975; Kohler et al., Eur. J. Immunol. 6:292 and 6:511, 1976; Hammerling et al., In Monoclonal Antibodies and T Cell Hybridomas, Elsevier, NY, 1981). Alternatively, in various embodiments, an immunologically-active antibody fragment, such as an Fab', (Fab')$_2$, or genetically engineered Fv fragment (see U.S. Pat. No. 4,946,778, hereby incorporated by reference) may also be useful. Once generated, the antibodies may be purified according to standard methods and injected into a mammal, such as a human, in order to inhibit the inflammatory response caused by chemotaxis of various leukocytes, particularly monocytes.

Preferably, the nucleic acid molecules of the invention, cells that express these molecules, or a therapeutic composition containing the encoded polypeptides, are administered to a mammal in order to stimulate a local immune response. This approach would be particularly beneficial to mammals that are suffering from cancer. The cancer may be evident as, for example, a lymphoma (such as Hodgkin's lymphoma), a plasmacytoma, a melanoma, a sarcoma, or a tumor within the lung or gastrointestinal tract.

In the event that the desired result is inhibition (rather than stimulation) of a local immune response, a mutant MCP-4 or MCP-5 polypeptide, antibodies or fragments thereof that specifically bind MCP-4 or MCP-5, or antisense MCP-4 or MCP-5 oligonucleotides may be administered. The mutant MCP-4 or MCP-5 polypeptides may lack, for example, between one and ten of the amino acid residues present at the amino terminus of the mature polypeptides. Alternatively, the mutant polypeptides may contain additional amino acid residues, for example between 3 and 10 amino acid residues, at the amino-terminus of the mature polypeptides. Where amino acid residues are added, they may be random or they may be selected to have particular biological properties such as stability or hydrophilicity. Antisense MCP-4 or MCP-5 oligonucleotides preferably consist of at least eight nucleotides, and have a sequence that is the reverse and complement of that found within the genes encoding these polypeptides.

Suppression or inhibition of the local immune response would be beneficial when, for example, the mammal has been diagnosed as having asthma, chronic obstructive pulmonary disease, cystic fibrosis, sinusitis, rhinitis, atherosclerosis, glomerulonephritis, multiple sclerosis, or an inflammatory bowel disease.

The nucleic acid molecules of the invention are also useful in treating a mammal that is suffering from an infectious disease, such as acquired immune deficiency syndrome (AIDS) or malaria. Preferably, the method of treatment consists of administering to the infected mammal an MCP-4 or MCP-5 polypeptide, or a fragment thereof that is sufficient to bind the chemokine receptors by which these infectious agents gain entry to the cell.

The local immune response may also be modulated by administering a compound that modulates the chemotactic activity of MCP-4 or MCP-5. Examples of such modulators include interferon-gamma, tumor necrosis factor-α, interleukin-1, and interleukin-4. Additional modulatory compounds may be discovered by, for example, the method described herein, whereby a population of cells that express MCP-4 or MCP-5 is obtained, a subset of these cells is contacted with a candidate modulatory compound and the level of MCP-4 or MCP-5 expression in the subset of cells is compared with the level of expression in an equivalent number of cells in the initial population that were not contacted with the potential modulator. A difference in the level of MCP-4 or MCP-5 expression would indicate the presence of a compound that modulates MCP-4 or MCP-5 expression. Either gene expression or protein expression may be readily assessed by methods well known to skilled artisans. For example, mRNA expression could be assessed by Northern blot or RNAse protection analyses and protein expression could be assessed by Western blot analysis.

By "polypeptide" is meant any chain of more than two amino acids, regardless of post-translational modification such as glycosylation or phosphorylation.

By "substantially pure" is meant that the substance in question, be it a nucleic acid molecule, a polypeptide, or an antibody, has been separated from the components that naturally accompany it. Typically, a polypeptide is substantially pure when it is at least 60%, by weight, free from the proteins and naturally-occurring organic molecules with which it is naturally associated. Preferably, a preparation of MCP-4 or MCP-5 is at least 75%, more preferably at least 90%, and most preferably at least 99% pure, by weight. A substantially pure polypeptide may be obtained, for example, by extraction from a natural source (e.g., a mammalian cell), by expression of a recombinant nucleic acid encoding the polypeptide, or by chemically synthesizing the polypeptide. Purity can be measured by any appropriate method, such as column chromatography, polyacrylamide gel electrophoresis, or by HPLC analysis. In reference to a DNA molecule, "substantially pure" means that the molecule is free of the genes that flank it in the naturally-occurring genome of the organism from which it is obtained. The term therefore includes, for example, a recombinant DNA molecule which is incorporated into a vector; into an autonomously replicating plasmid or virus; into the genomic DNA or a prokaryote or eukaryote; or which exists as a separate molecule (e.g., a cDNA or a genomic or cDNA fragment produced by the polymerase chain reaction (PCR) or by restriction endonuclease digestion). It also includes a recombinant DNA which is part of a hybrid gene encoding additional polypeptide sequence.

By "substantially identical" to MCP-4 and MCP-5 is meant a sequence having at least 80% identity to the MCP-4 and MCP-5 sequences shown in FIGS. 1A and 1B. Preferably, the identity is 90% and most preferably the identity is 95%.

By "operably linked" is meant that a gene or portion of a gene is connected to one or more regulatory elements, which are also a particular DNA sequences, in such a way as to permit expression of the gene when the appropriate molecules (e.g., transcriptional activator proteins) are bound to the regulatory element(s).

The term "transgenic" as used in reference to an animal or a cell, means an animal or cell into which a DNA sequence has been inserted by artifice and which becomes a part of the genome of the animal or cell.

By "biological activity" of MCP-4 or MCP-5 is meant the biological activity (preferably monocyte chemoattractant activity) which is at least 50% of that observed using MCP-4 or MCP-5, having the sequence shown in FIGS. 1A and 1B respectively, in any of the assays describes herein. Preferably the activity is 80% of the activity observed with the MCP-4 and MCP-5 polypeptides of FIGS. 1A and 1B, and most preferably, the activity is 95% of that observed with the MCP-4 and MCP-5 polypeptides of FIGS. 1A and 1B.

By "modulatory compound" or "modulator" is meant any compound that is capable of increasing or decreasing the expression or activity of MCP-4 or MCP-5. Expression may be modified at the level of transcription, translation, or post-translation. Activity may be modified at the level of receptor binding or within the cytoplasm of a cell. Activity may be assessed as, for example, monocyte chemotaxis per unit of MCP-4 or MCP-5 protein. Activity would be considered stimulated if, for example, the number of monocytes in a target tissue is at least 20% greater than the number of monocytes in a control, untreated tissue that is in all other substantive ways identical to the treated tissue. Conversely, activity would be considered inhibited if, for example, the number of monocytes in a target tissue is at least 20% less than the number of monocytes in a control, untreated tissue that is in all other substantive ways identical to the treated tissue.

Other features and advantages of the invention will be apparent from the following description and from the claims.

Figure 3A:
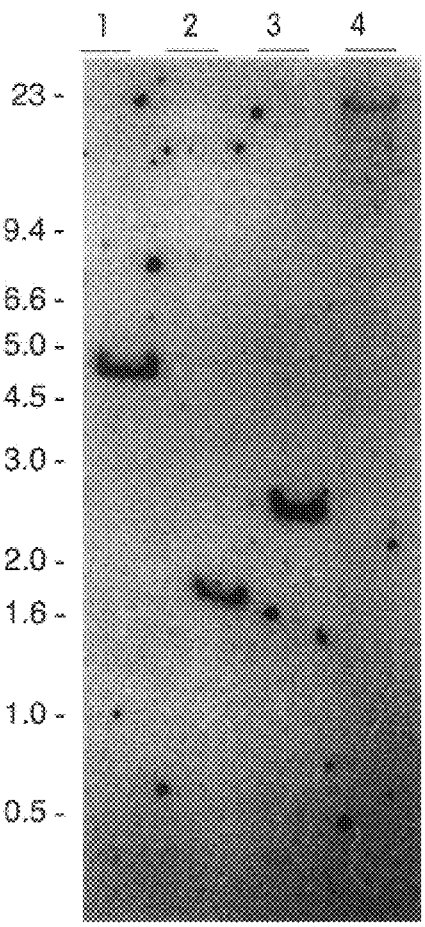
FIGS. 3A and 3B are scanned images of a Southern blot probed at high stringency (FIG. 3A) or low stringency (FIG. 3B) with a $^{32}$P-labeled human MCP-4 cDNA probe. Human genomic DNA was digested with PstI (lane 1), BglII (lane 2), HindIII (lane 3), or EcoRI (lane 4).
Figure 3B:
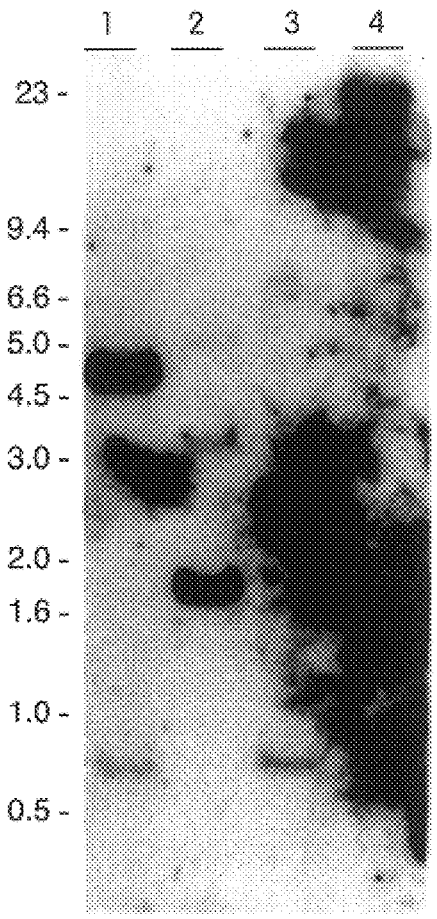
Figure 3C:
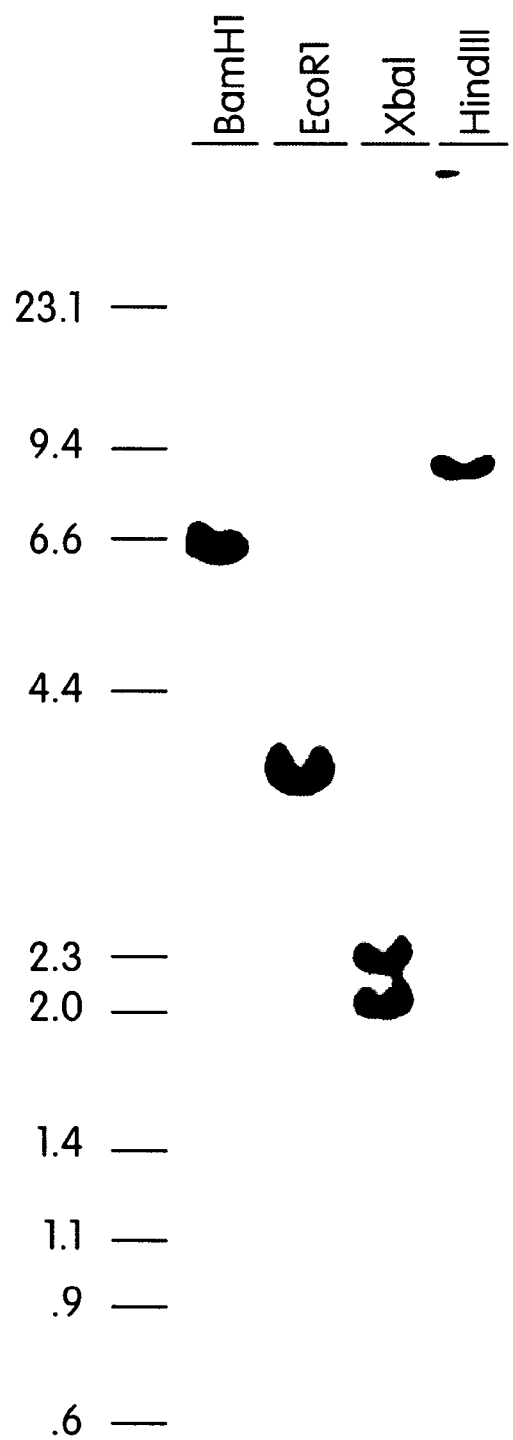
FIG. 3C is a scanned image of a Southern blot probed with a full-length MCP-5 cDNA probe. Mouse genomic DNA was digested with BamHI (lane 1), EcoRI (lane 2), XbaI (lane 3), or HindIII (lane 4).

In each of FIGS. 3A–3C, the position of molecular weight markers are indicated (in kb) on the left.

Figure 3D:
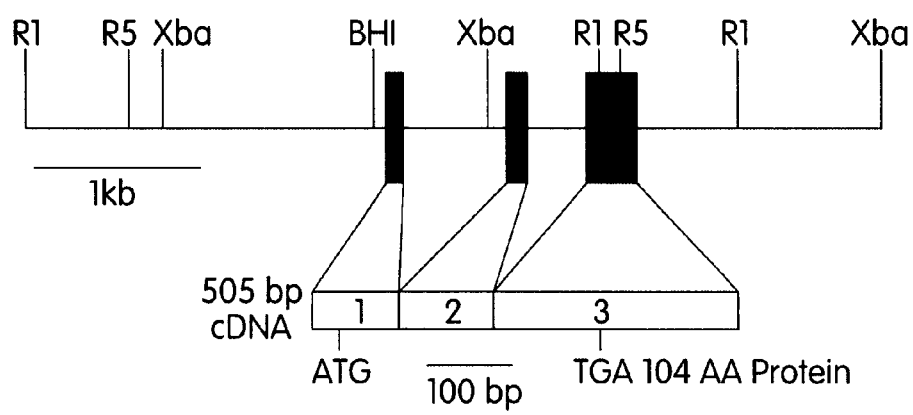

FIG. 3D is a representation of the genomic organization of the mouse MCP-5 gene, including selected restriction sites (top). The mature mRNA is also shown schematically (bottom), with the locations of the start (ATG) and stop codons (TGA) indicated.

Figure 3E:
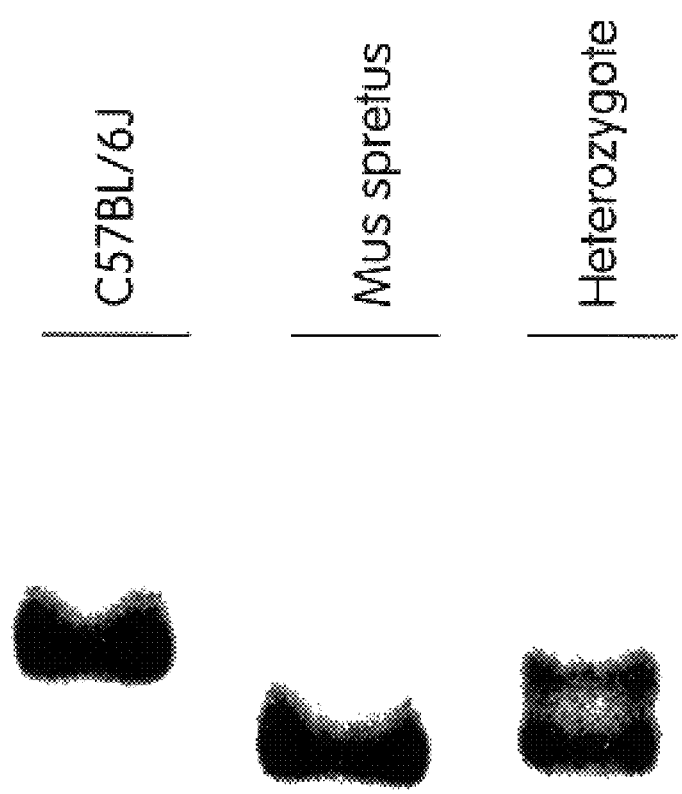

FIG. 3E is a scanned image of PCR products obtained by amplifying genomic DNA from C57BL/6J, *Mus spretus*, and heterozygous mice with primers in intron 2 of MCP-5.

Figure 3F:
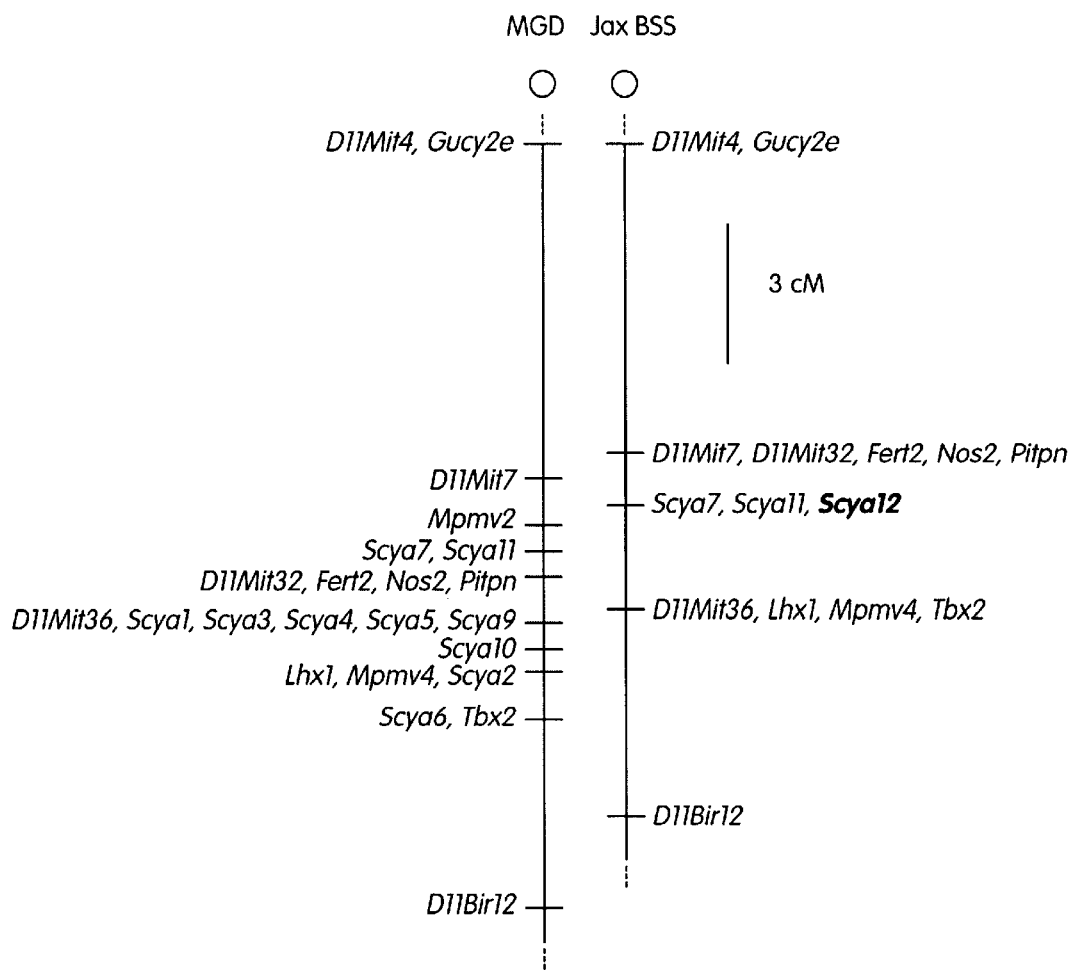

FIG. 3F is a map depicting the location of the MCP-5 gene on mouse chromosome 11.

Figure 4A:
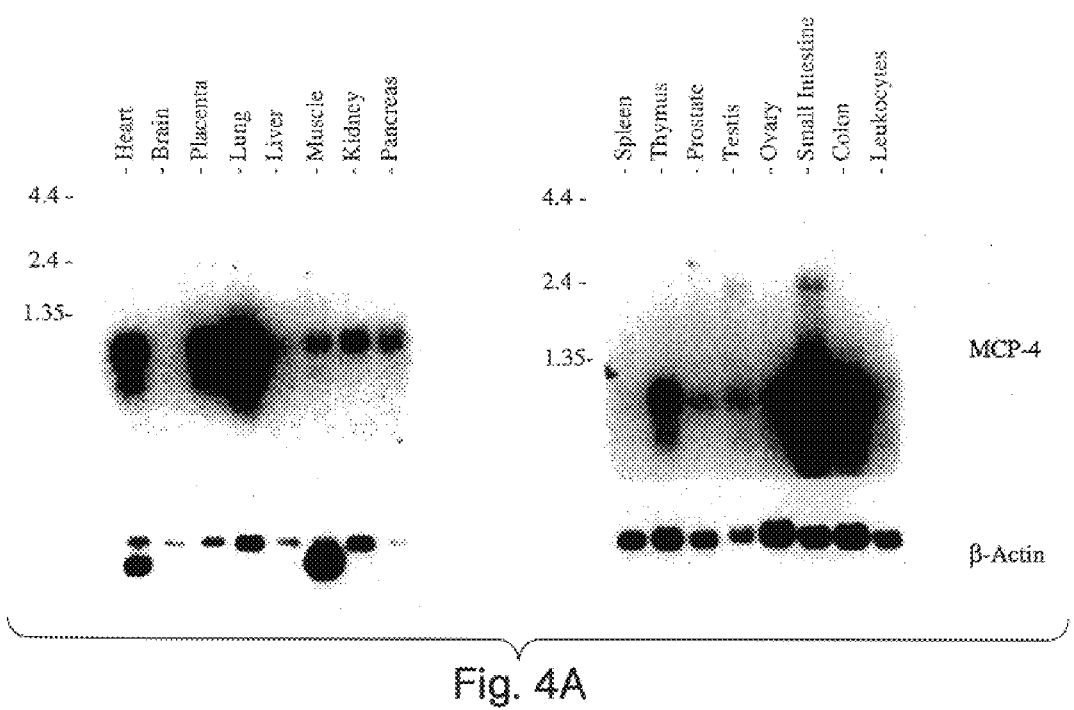

FIG. 4A is a scanned image of a Northern blot that was probed with a $^{32}$P-labeled human MCP-4 cDNA probe (upper blots) and a human β-actin cDNA probe (lower blots). Poly-A$^+$ mRNA was isolated from the human tissues indicated. The position of molecular weight markers is shown (in kb) on the left.

Figure 4B:
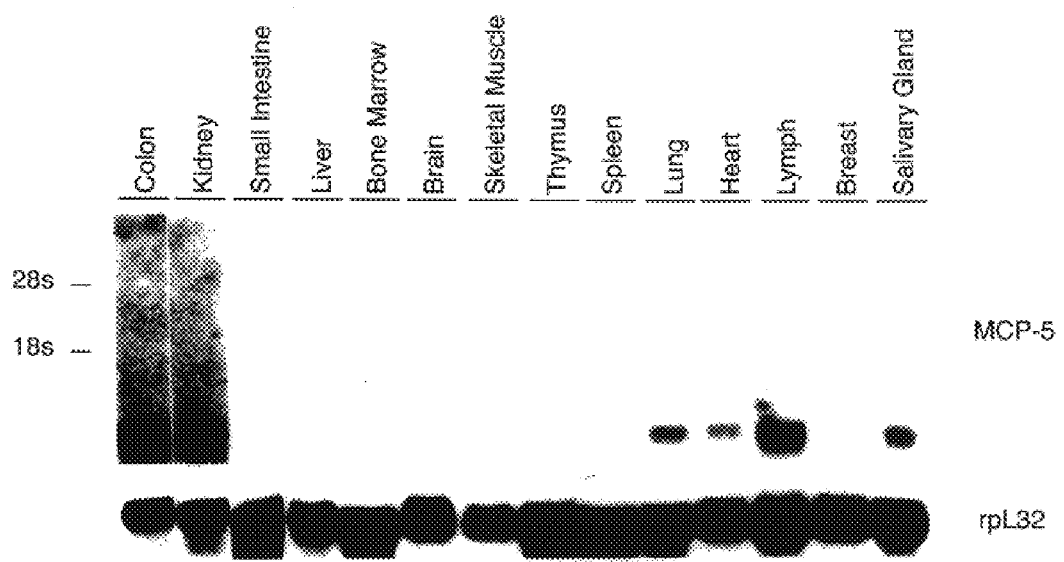

FIG. 4B is a scanned image of a Northern blot depicting MCP-5 expression in normal mouse tissues. The blot was probed sequentially with cDNA probes for MCP-5 and, as a control for RNA loading, rpL32 ribosomal protein. The positions of 18s and 28s RNA are indicated on the left.

Figure 4C:
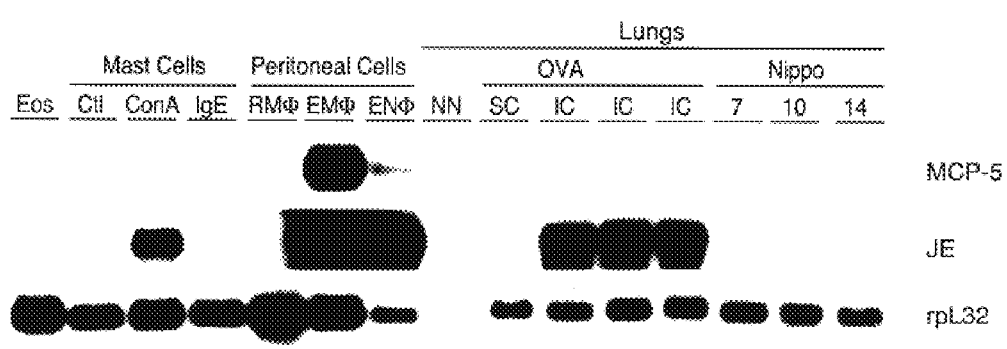

FIG. 4C is a scanned image of a Northern blot depicting MCP-5 expression in murine leukocytes and in tissues of mice that serve as models of pulmonary inflammation. Each lane represents an individual mouse from a representative experiment (n=3).

Figure 4D:
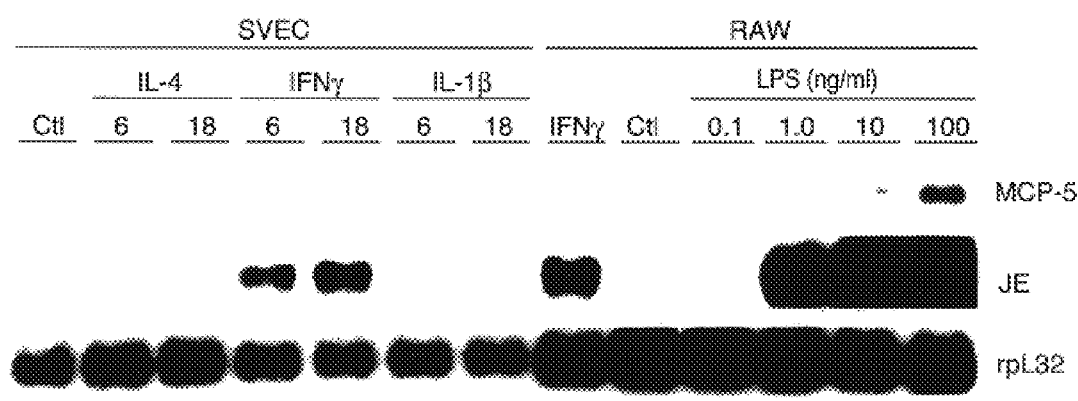

FIG. 4D is a scanned image of a Northern blot depicting MCP-5 expression in activated macrophages (from the RAW 264.7 macrophage cell line) and endothelial cells (SVEC cells). The cells were untreated (Ctl) or treated with IL-4 IFNγ, IL-1β, or LPS as indicated.

Figure 5A:
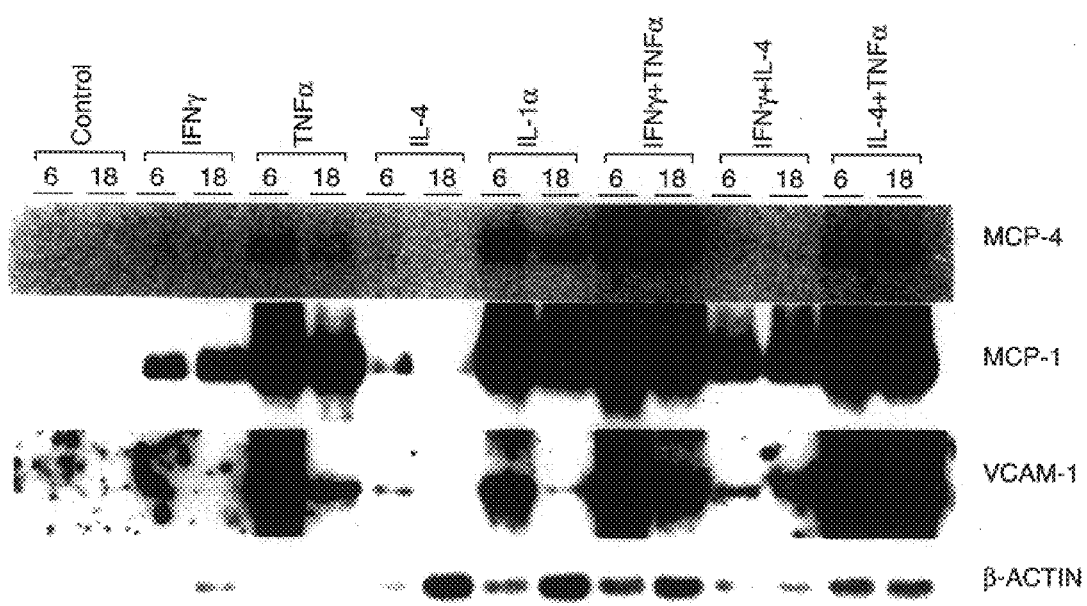

FIG. 5A is a series of scanned image of a Northern blot that was probed sequentially with MCP-4, MCP-1, VCAM-1 and β-Actin cDNA probes. Total RNA isolated from human umbilical vein endothelial cells was treated for the time shown with IFNγ, TNFα, IL-4, or IL-1α, or a combination of IFNγ/TNFα, IFNγ/IL-4, or TNFα/IL-4.

Figure 5B:
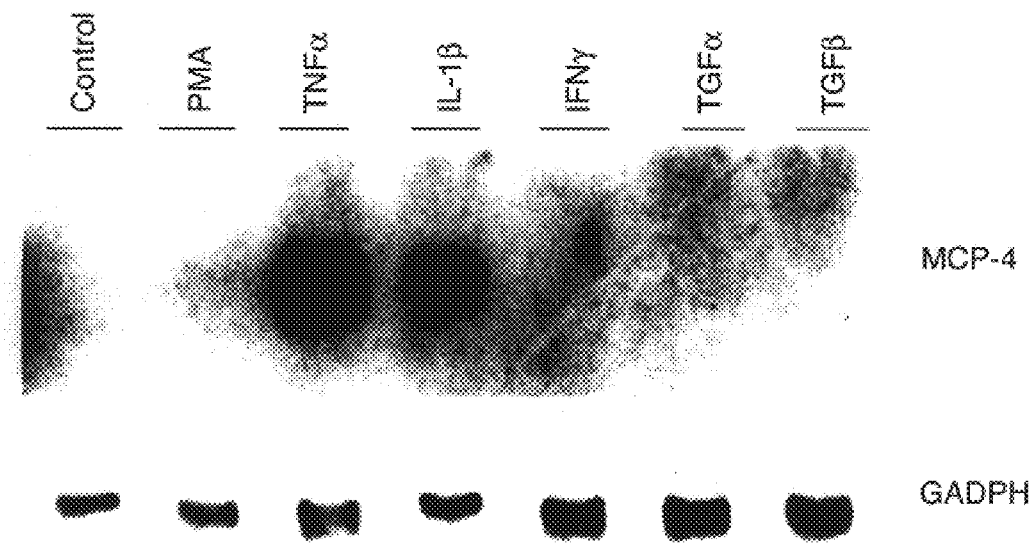

FIG. 5B is a pair of scanned image of a Northern blot hybridized sequentially with MCP-4 and GADPH cDNA probes. The samples consisted of total RNA, which was isolated from cells of the human respiratory epithelial cell line A549. The cells were either untreated (control) or treated with the cytokines listed above the corresponding lane of the blot (PMA, TNFα, IL-1β, IFNγ, TGFα, and TGFβ).

Figure 5C:
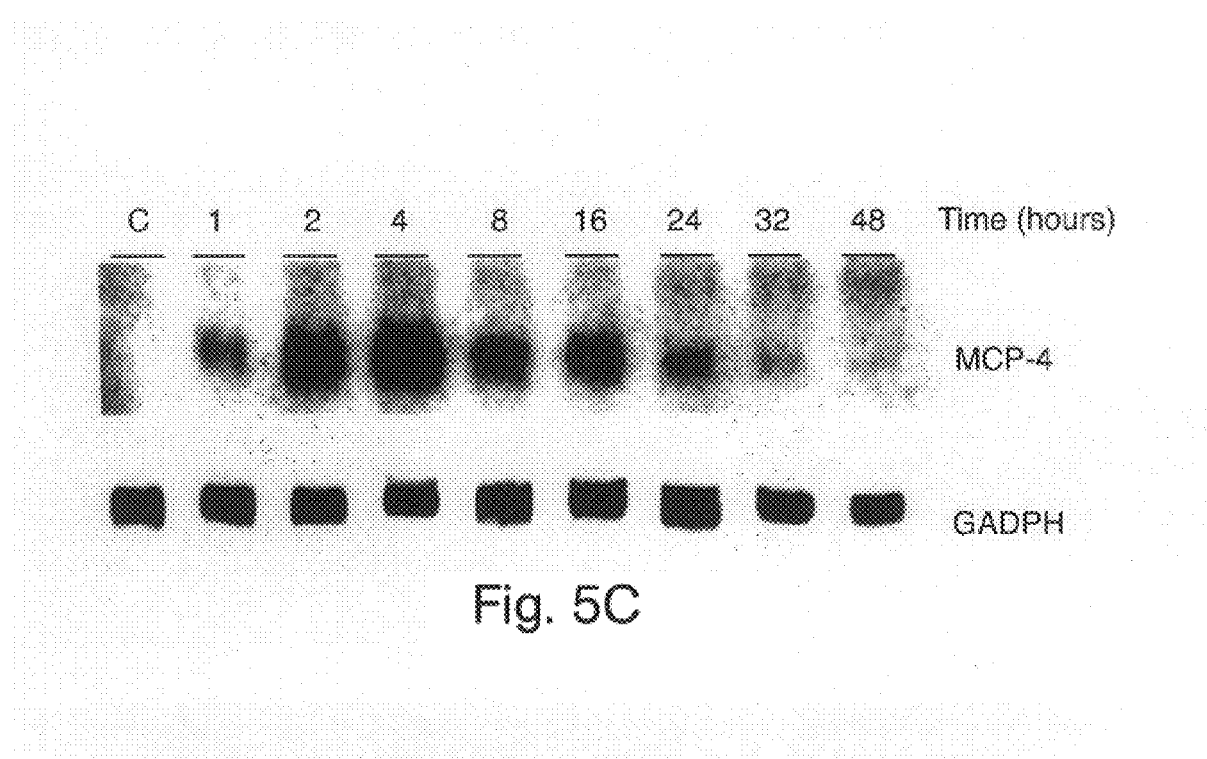

FIG. 5C is a pair of scanned image of a Northern blot that was hybridized sequentially with MCP-4 and GADPH cDNA probes. The samples consisted of total RNA, which was isolated from cells of the human respiratory epithelial cell line A549 at various times after treatment with 0.1 ng/ml IL-1β.

Figure 5D:
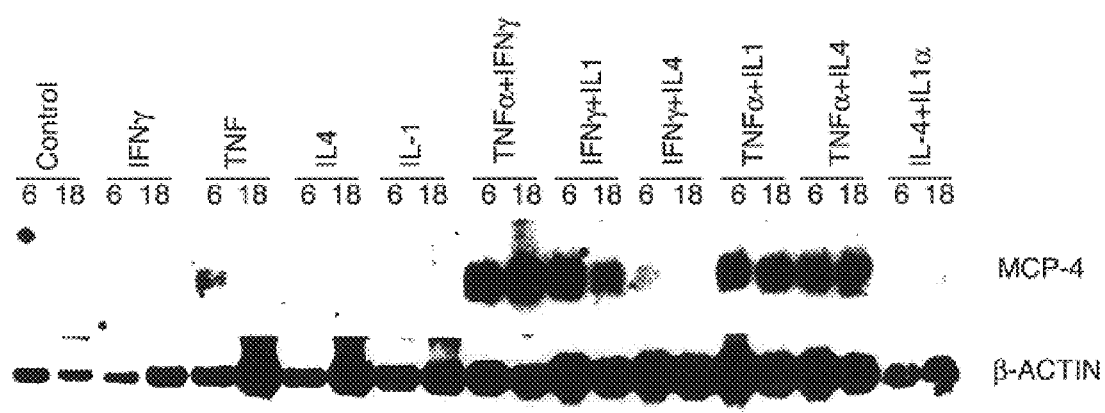

FIG. 5D is a pair of photographs of a Northern blot that was hybridized sequentially with MCP-4 and β-actin cDNA probes. Total RNA was isolated from the human respiratory epithelial cell line BEAS-2B either before (control), 6 hours, or 18 hours after stimulation with the cytokines listed above the corresponding lanes.

Figure 6A:
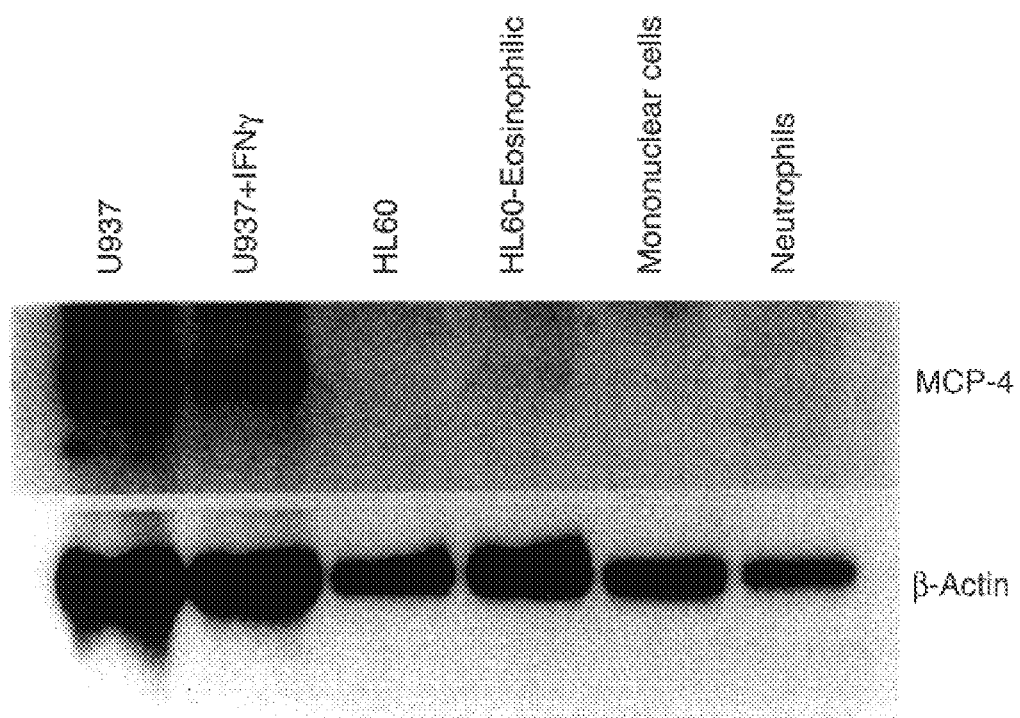

FIG. 6A is a pair of photographs of a Northern blot that was hybridized sequentially with MCP-4 and β-actin cDNA probes. Total RNA was isolated from untreated U937 cells (control; lane 1), U937 cells stimulated for 18 hours with IFNγ (lane 2), untreated HL60 cells (lane 3), an eosinophilic subline of HL60 cells that were cultured with butyric acid (HL60-Eosinophilic; lane 4), human peripheral blood mononuclear cells (lane 5), and neutrophils (lane 6).

Figure 6B:
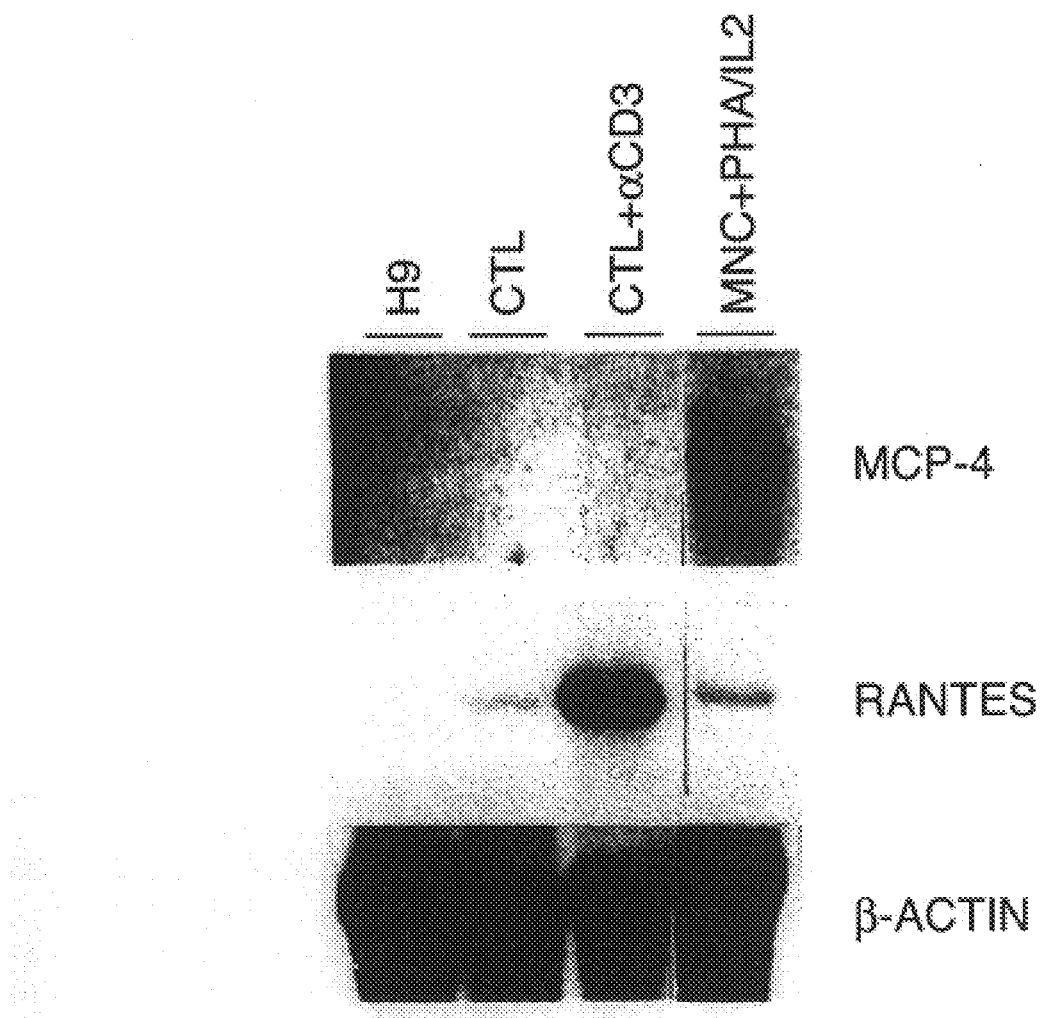

FIG. 6B is a series of photographs of Northern blots that were hybridized with either MCP-4, RANTES, or β-actin probes. Total RNA was isolated from H9 T cells (lane 1) $CD8^{30}$ HIV-specific cytolytic T cell clones that were unstimulated (lane 2) or stimulated with anti-CD3 (lane 3), and peripheral blood mononuclear cells cultured in the presence of PHA and IL-2 (lane 4).

Figure 6C:
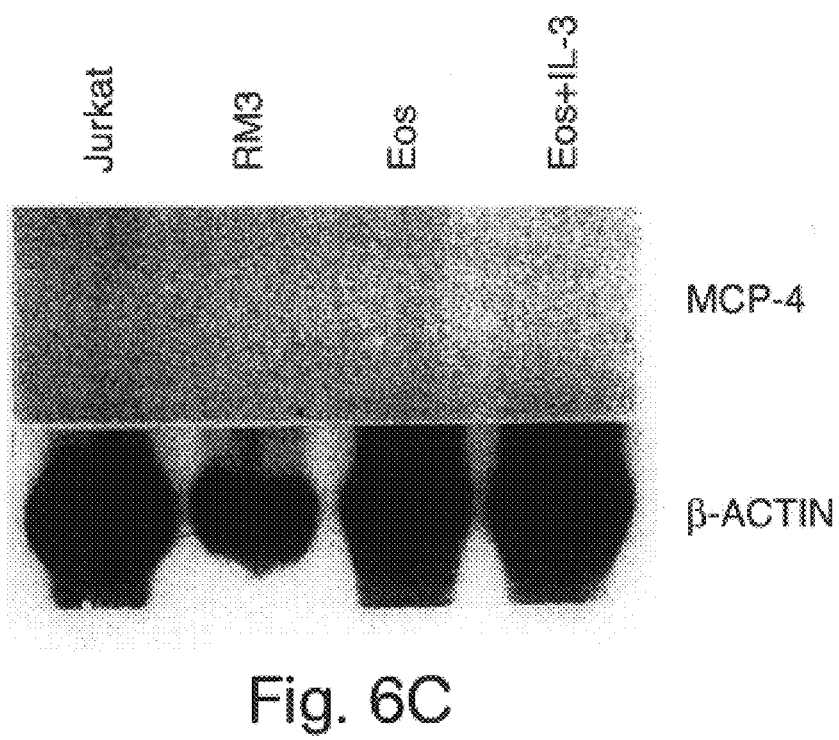

FIG. 6C is a pair of photographs of a Northern blot that was hybridized sequentially with MCP-4 and β-actin cDNA probes. Total RNA was isolated from Jurkat Cells (lane 1), the RM3 subline of Raji cells (lane 2), freshly isolated purified peripheral blood eosinophils, either before (lane 3) or after (lane 4) culture with IL-3.

Figure 7:
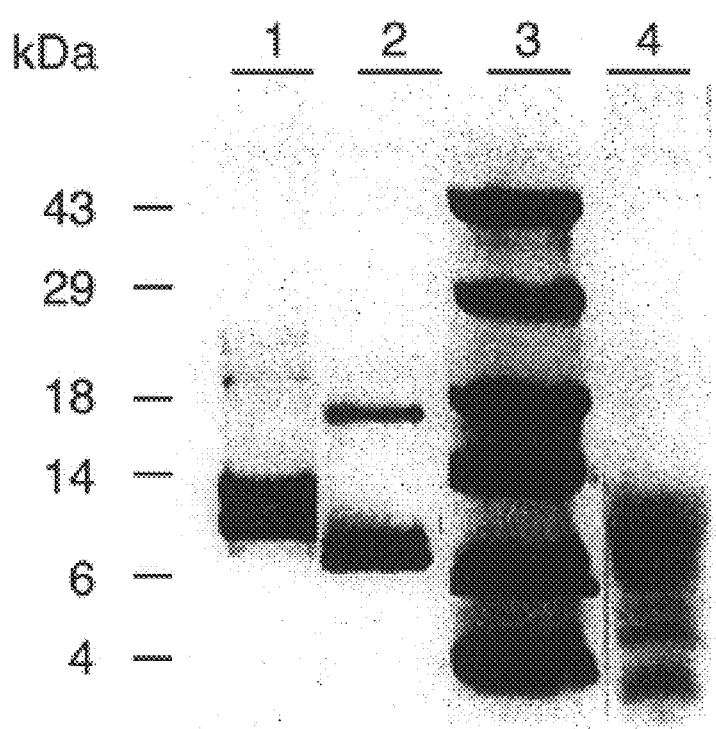

FIG. 7 is a photograph of an SDS-polyacrylamide gel (12.5%; Tris/Tricine) on which was electrophoresed recombinant MCP-4 His tagged protein (produced by *E. coli*) before factor Xa cleavage (lane 1; Coomassie stained), recombinant MCP-4 with the mature N-terminal Gln (PeproTech; lane 2; Coomassie stained), molecular weight standards (lane 3; values in kDa are indicated on the far left), and affinity purified MCP-4-FLAG protein (lane 4; Western blot).

Figure 8:
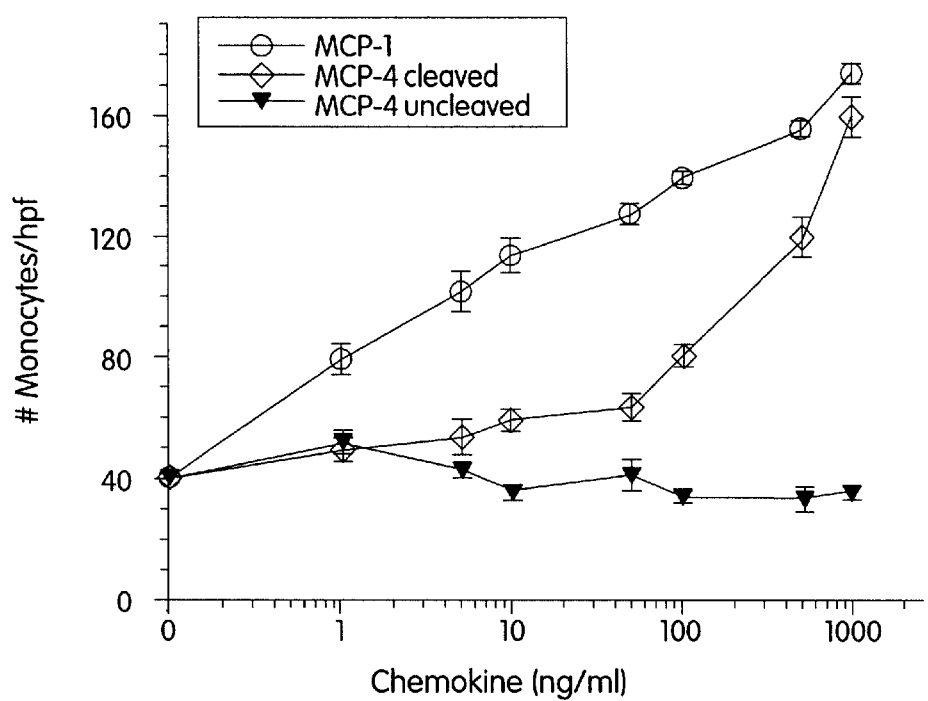

FIG. 8 is a line graph depicting chemotaxis of human elutriated monocytes to recombinant MCP-4 (produced by *E. coli*) before (uncleaved; closed triangles) and after factor Xa cleavage (cleaved; open diamonds). The chemotactic response to MCP-1 is also shown (open circles). The results are expressed as the mean±SEM for replicate samples.

Figure 9A:
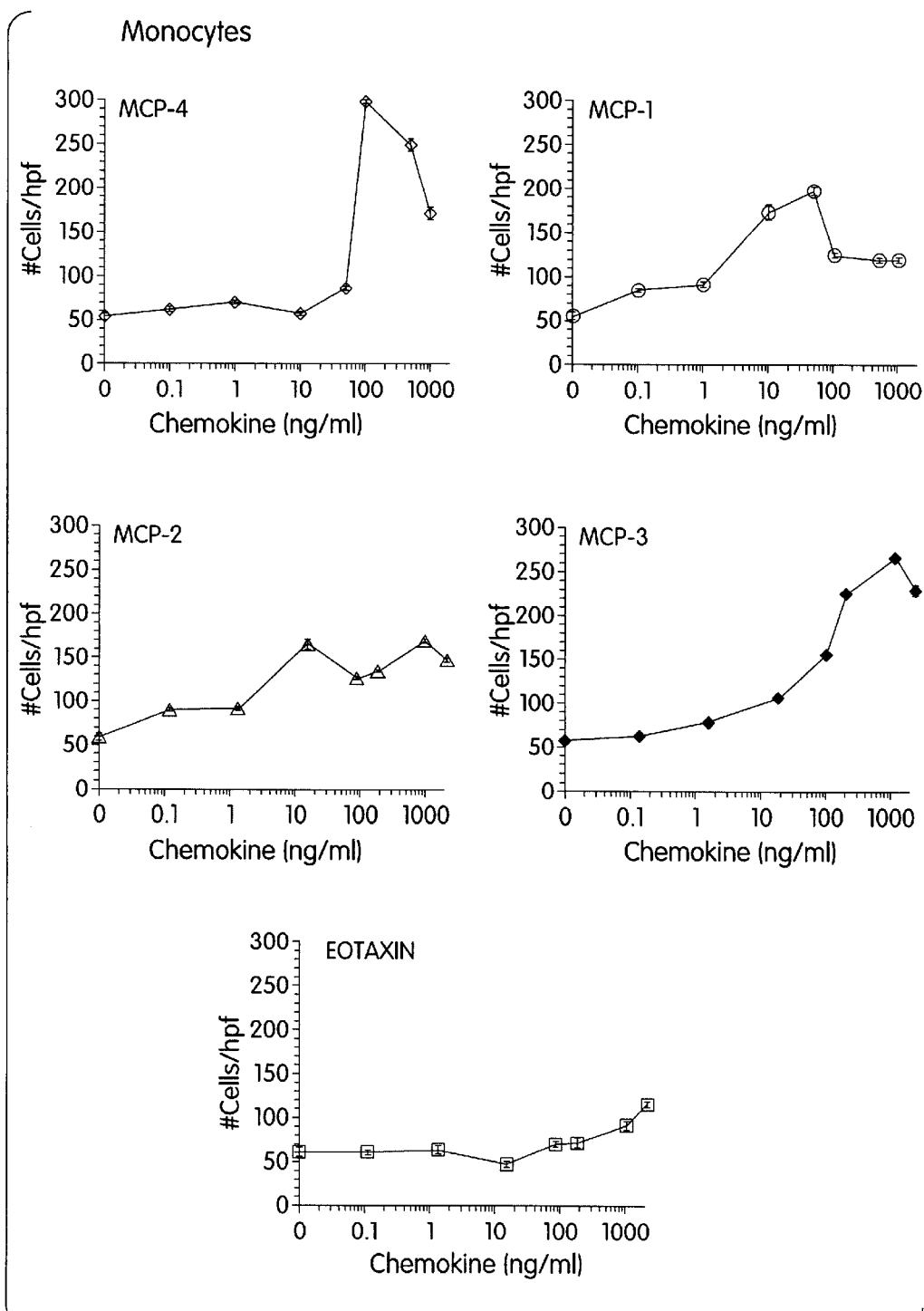

FIG. 9A is a panel of line graphs depicting chemotaxis of monocytes to MCP-4. Monocytes were subjected to chemotaxis in a modified Boyden chamber, and the number of cells that migrated through the membrane were counted (Y axis). Control chemotactic stimuli are indicated.

Figure 9B:
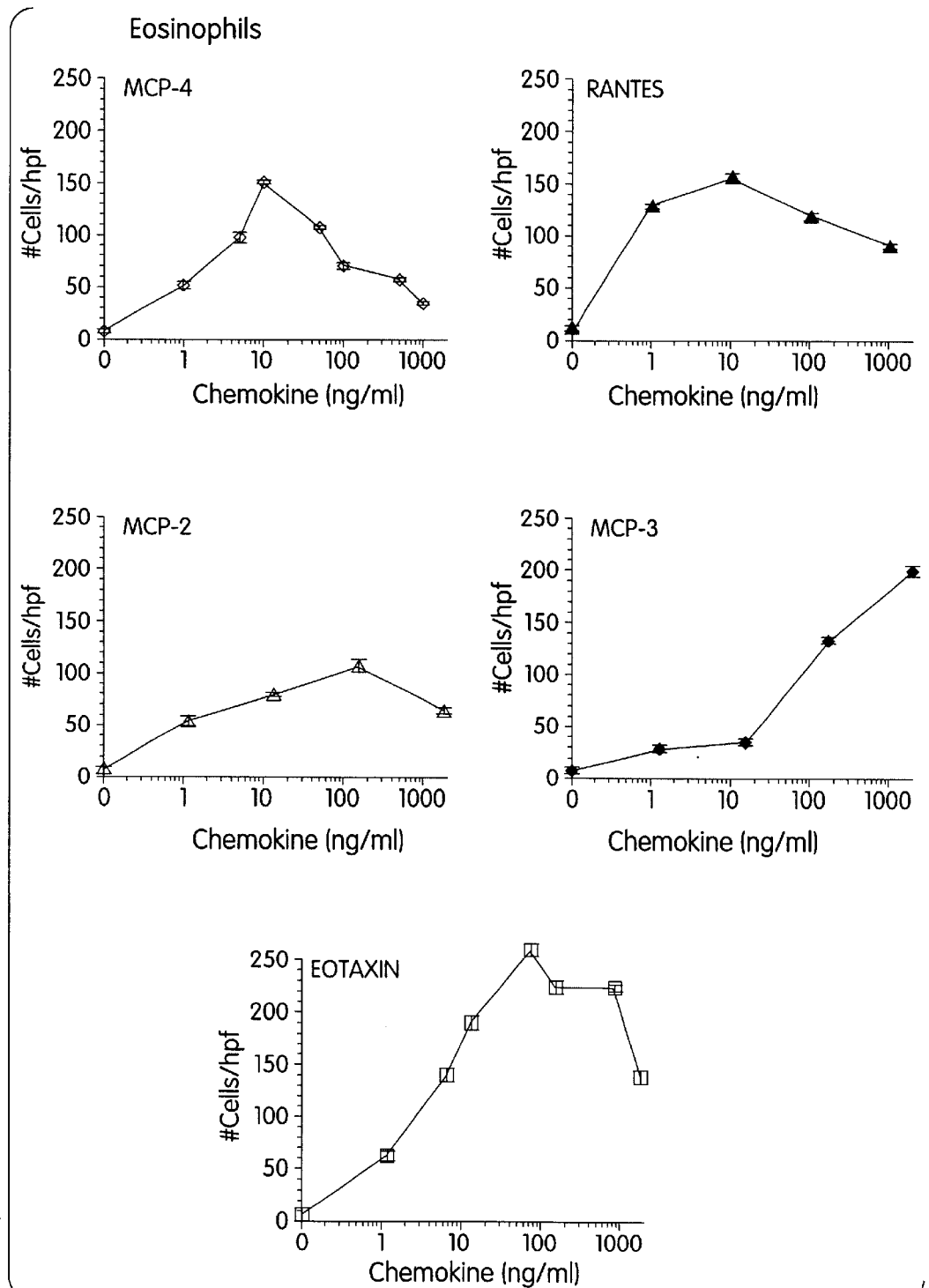

FIG. 9B is a panel of line graphs depicting chemotaxis of eosinophils to MCP-4. Monocytes were subjected to chemotaxis in a modified Boyden chamber, and the number of cells that migrated through the membrane were counted. Control chemotactic stimuli are indicated.

Figure 9C:
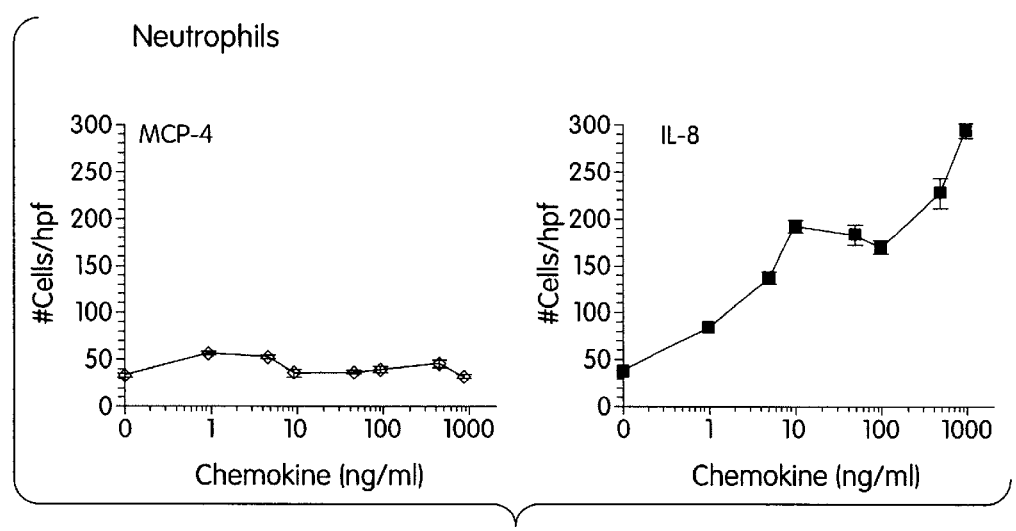

FIG. 9C is a panel of line graphs depicting chemotaxis of eosinophils. Neutrophils were subjected to chemotaxis in the presence of MCP-4 in a modified Boyden chamber, and the number of cells that migrated through the membrane were counted (shown on left-hand graph). A control chemotactic stimulus, IL-8, is also shown (right-hand graph).

In each of FIGS. 9A, 9B, and 9C, the chemotaxis results are expressed as the mean±SEM for replicate samples from one of five donors tested.

FIGS. 9D–9G are line graphs depicting chemotaxis of human peripheral blood mononuclear cells (9D; n=4), mouse thiogylcolate elicited peritoneal macrophages (9E; n=1), mouse eosinophils (9F; n=5), and mouse neutrophils (9G; n=3) following exposure to increasing concentrations of the indicated chemokines in a modified Boyden chamber.

In each of FIGS. 9D–9G, the results are expressed as the mean±SEM for 8 hpf (high powered fields) counted in replicate wells.

Figure 10A:
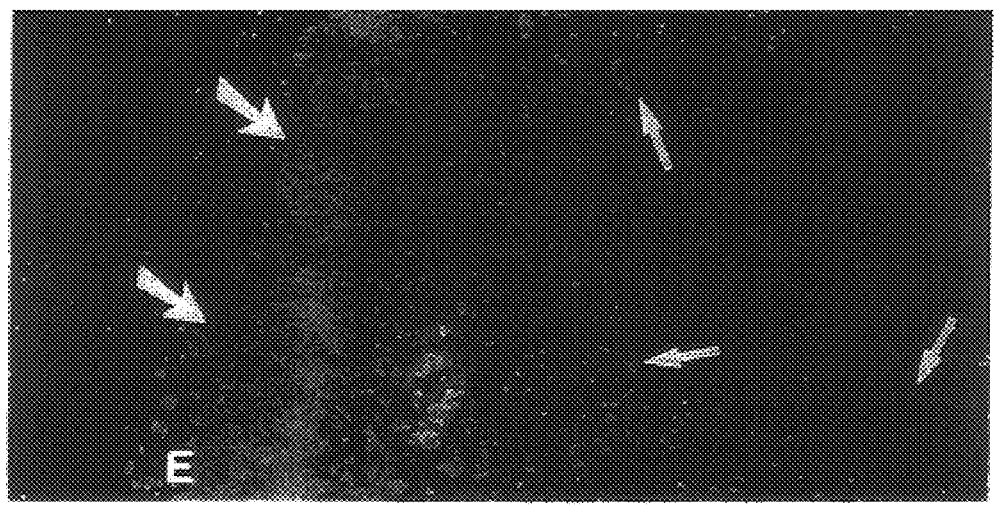

FIG. 10A is a dark field photomicrograph of a section of tissue, obtained from a human patient with hypertrophic sinusitis, that was hybridized with a radiolabelled MCP-4 cRNA probe. "E" labels the epithelium.

Figure 10B:
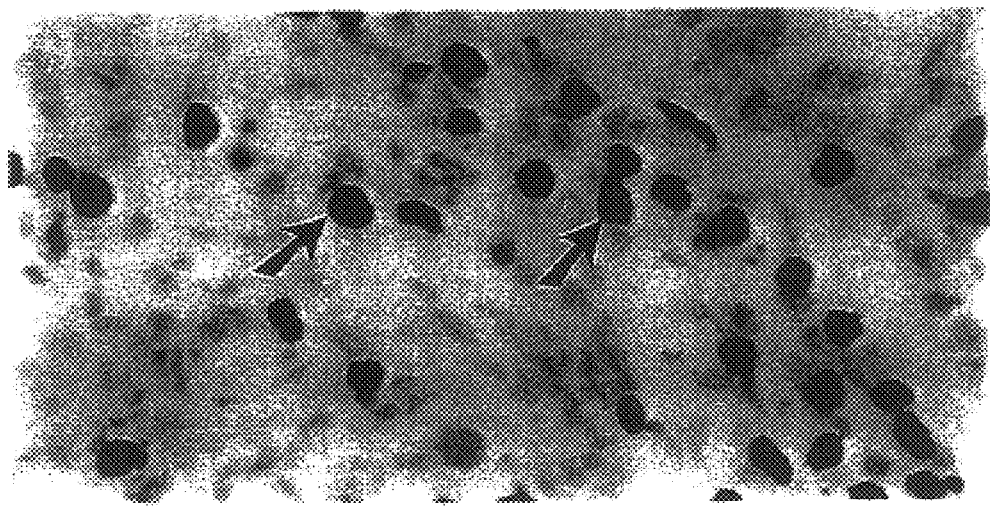

FIG. 10B is a bright field photomicrograph of a section of tissue, obtained from a human patient with hypertrophic sinusitis, that was hybridized with a digoxigenin-labeled MCP-4 cRNA probe. The arrows point to mononuclear cells.

Figures 1, 11A:
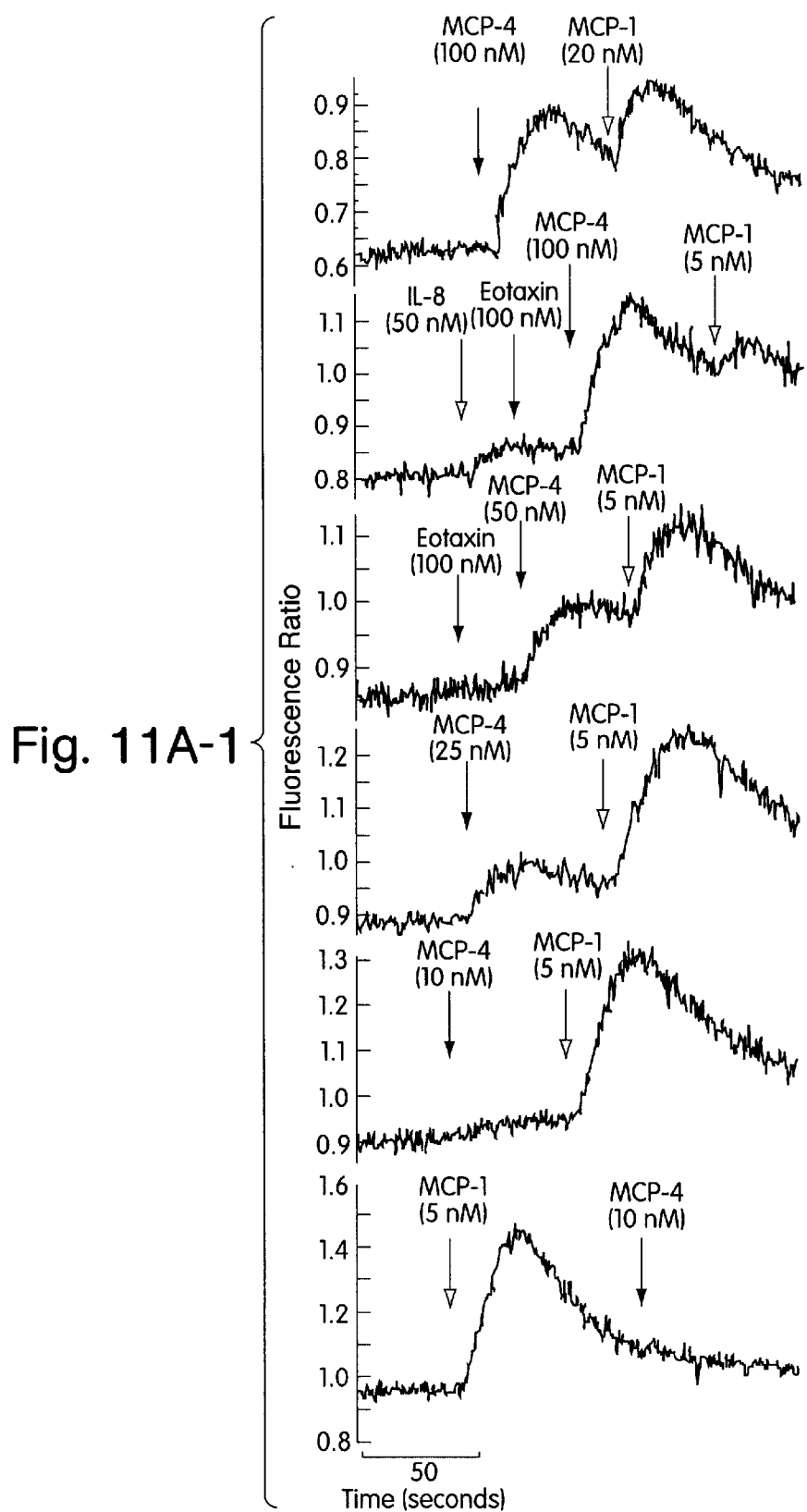
FIG. 1A is a schematic representation of the nucleotide sequence (bottom line; SEQ ID NO:1) and predicted amino acid sequence (top line; SEQ ID NO:2) of human MCP-4. The stop codon is indicated by asterisks; the predicted site for signal peptidase cleavage is indicated by an arrow; and a putative mRNA destabilizing sequence is underlined. The putative mature protein is numbered from +1 to +75.
FIG. 1B is a schematic representation of the nucleotide sequence (bottom line; SEQ ID NO:3) and predicted amino acid sequence (top line; SEQ ID NO:4) of murine MCP-5. The intron/exon borders are indicated by triangles; the ATTTA sequence (which may decrease mRNA stability) is singly underlined; the predicted polyadenylation signal is doubly underlined; and the predicted site for a signal peptidase cleavage is marked with an arrow (just 5' to the +1 site).

FIG. 11A is a series of tracings representing calcium flux stimulated by MCP-4 in mononuclear cells. Fura-2-loaded cells were exposed sequentially to the indicated chemokines with the concentration of each stimulus indicated in parenthesis below the name of the chemokine. Calcium flux is reported as ratio fluorescence of fura-2.

Figures 2, 11A:
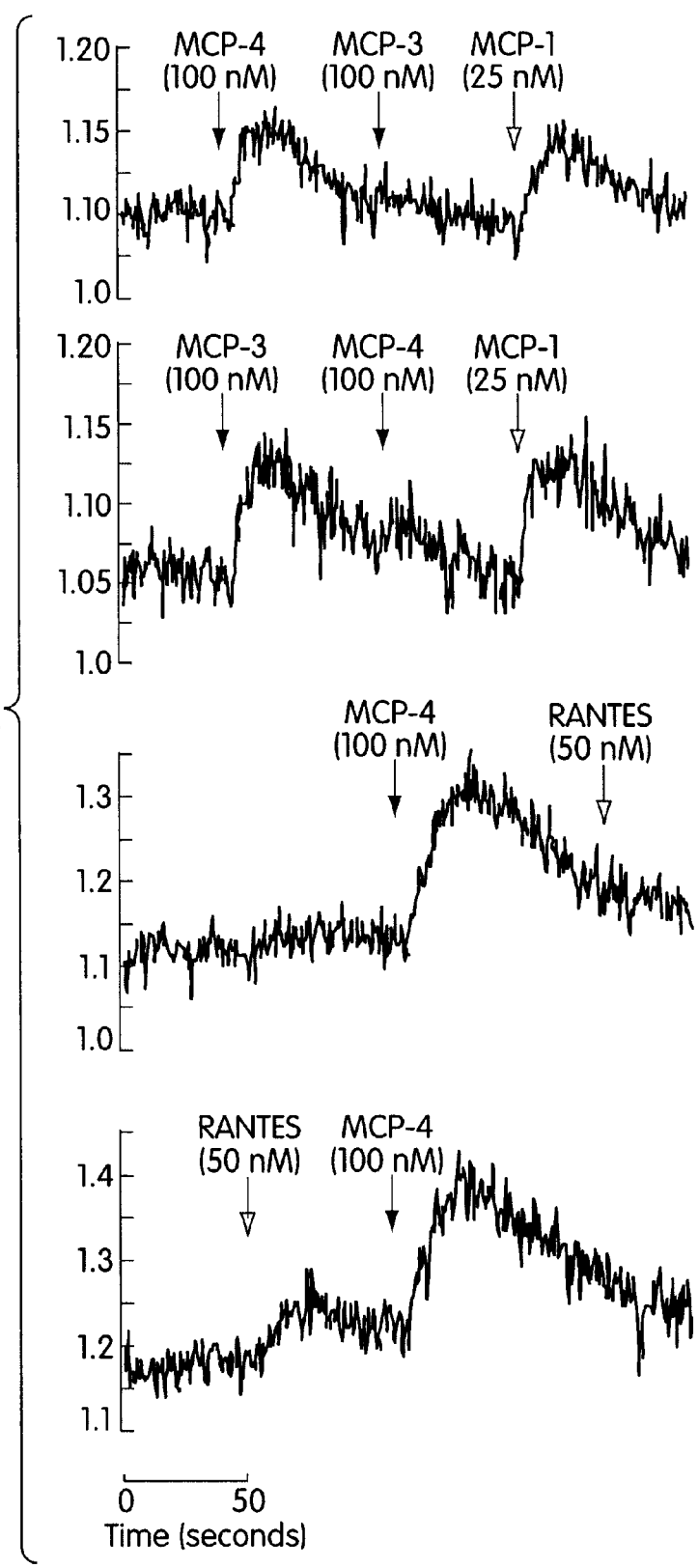
FIG. 2A is a schematic representation of the human MCP-4 amino acid sequence (SEQ ID NO:2), aligned with other chemokines having the CC motif (indicated by bold face type; SEQ ID NOs:5–14). The +1 predicts the mature N-terminus after signal peptidase cleavage (arrow), and gaps to maximize alignment are indicated by (-). The last 48 amino acids of murine MCP-1 have been omitted.
FIG. 2B is a schematic representation of the amino acid sequence of human MCP-4 (SEQ ID NO:2) murine MCP-5 (SEQ ID NO:4), and other mouse and human CC chemokines (SEQ ID NOs:5–8 and 14–16). Conserved amino acids are boxed, and the position of leader sequence cleavage is indicated by an arrow.
Figure 11B:
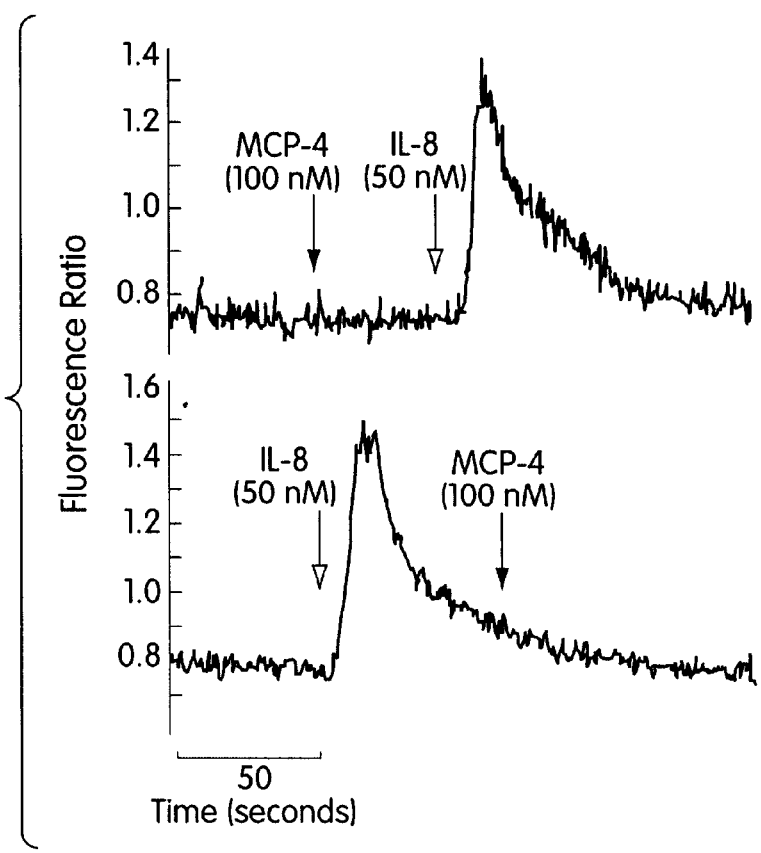

FIG. 11B is a series of tracings representing calcium flux stimulated by MCP-4 in neutrophils. Fura-2-loaded cells were exposed to chemokines, as described for FIG. 11A above, and changes in intracellular fluorescence were monitored.

Figure 11C:
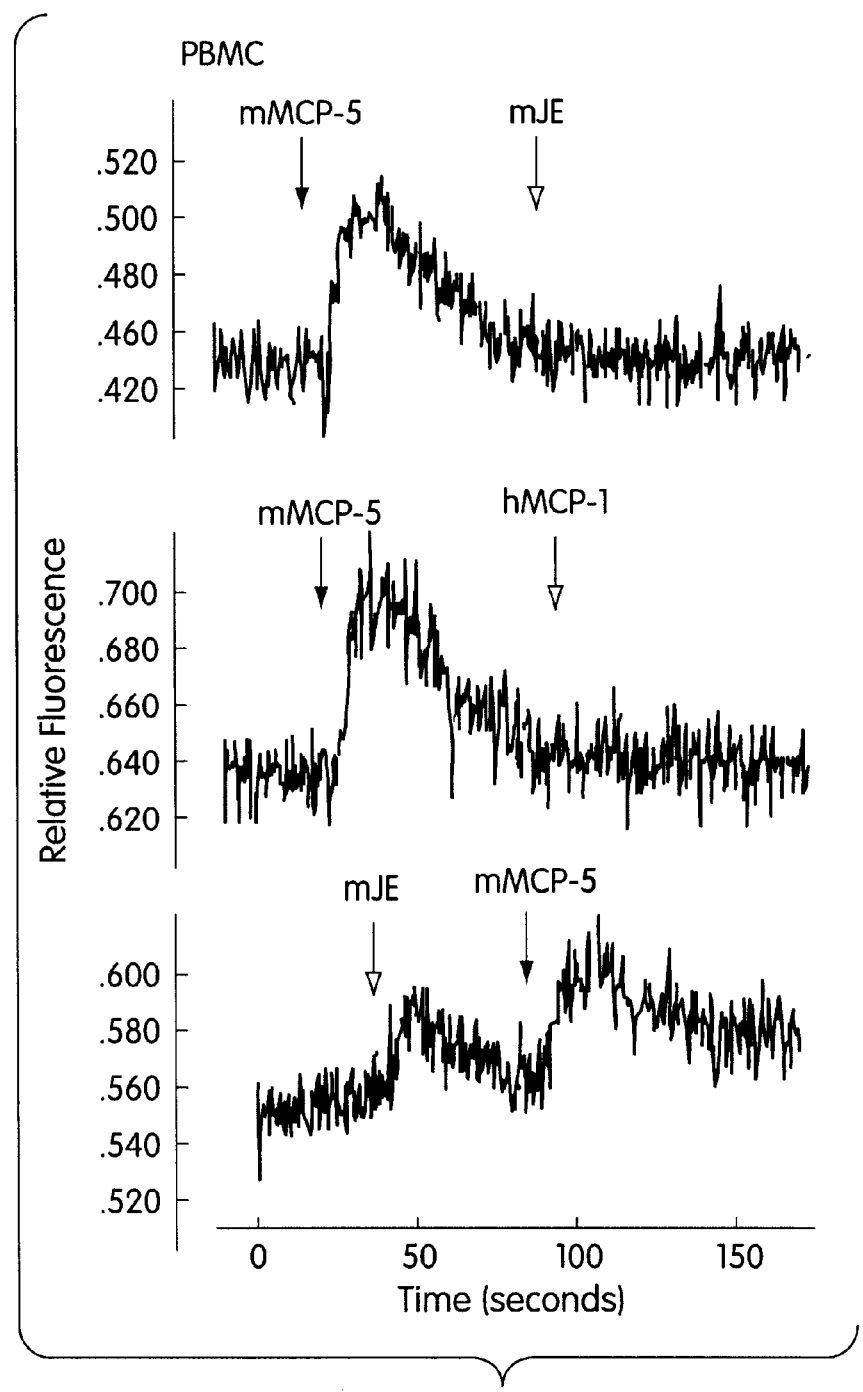
Figure 11D:
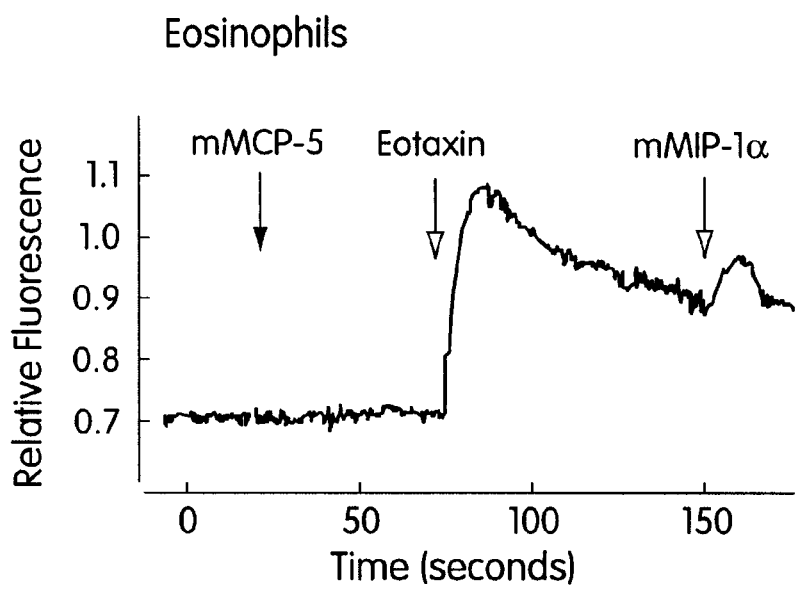
Figure 11E:
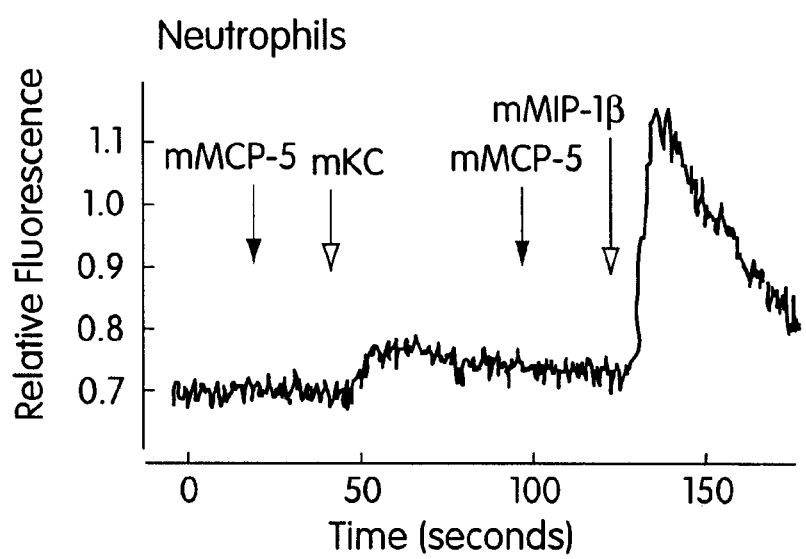

FIGS. 11C–11E are a series of tracings representing calcium flux in human peripheral blood mononuclear cells (11C), eosinophils (11D), and neutrophils (11E) following sequential application of 100 nM of mMCP-5, mJE, hMCP-1, mMIP-1β, mMIP-1α, eotaxin, and mKC, as indicated.

Figure 11F:
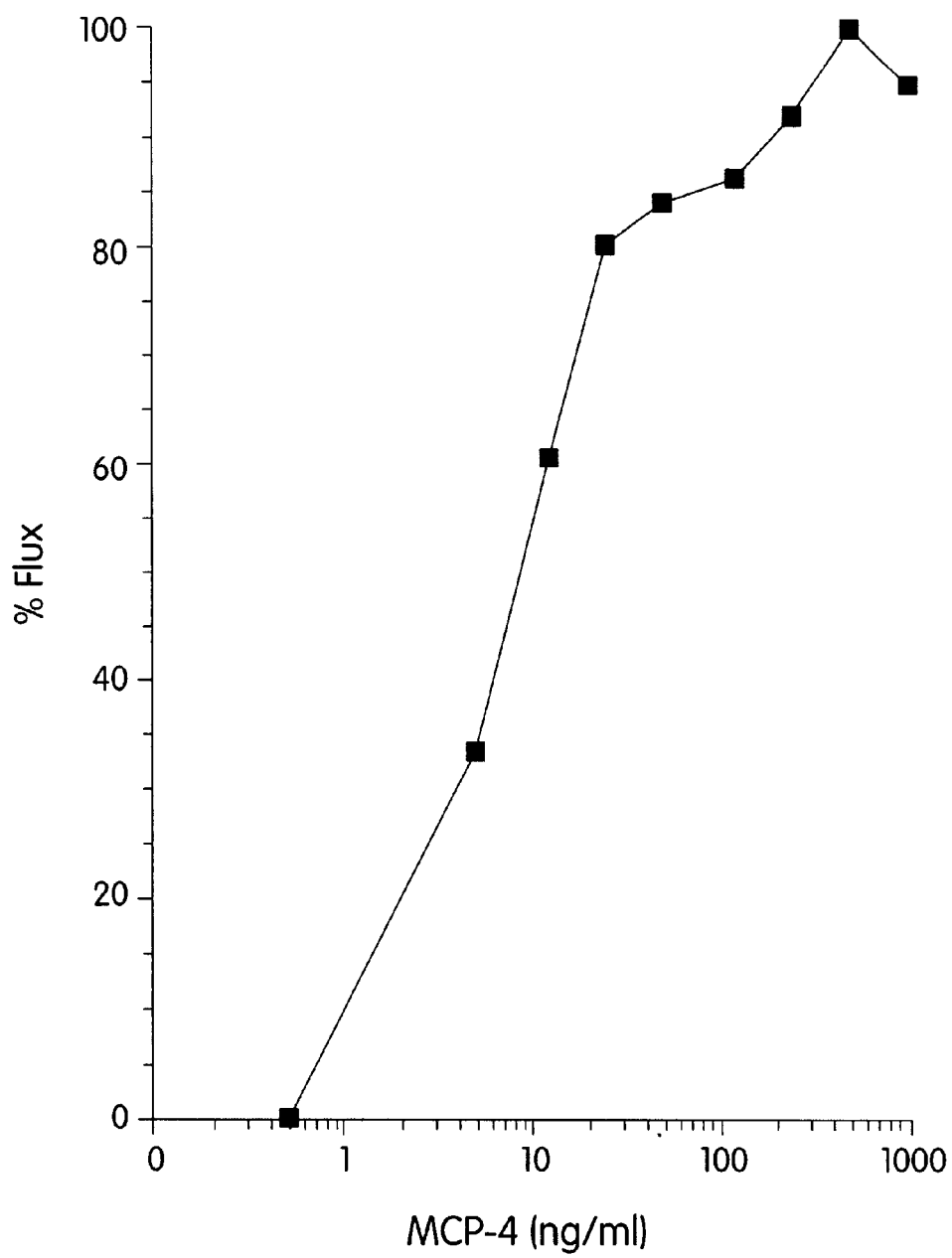

FIG. 11F is a line graph depicting the concentration dependence of MCP-4 induced calcium flux in human mononuclear cells. The magnitude of the calcium transient peak induced by MCP-4 is plotted as a percentage of the maximal response observed for MCP-5.

Figure 12A:
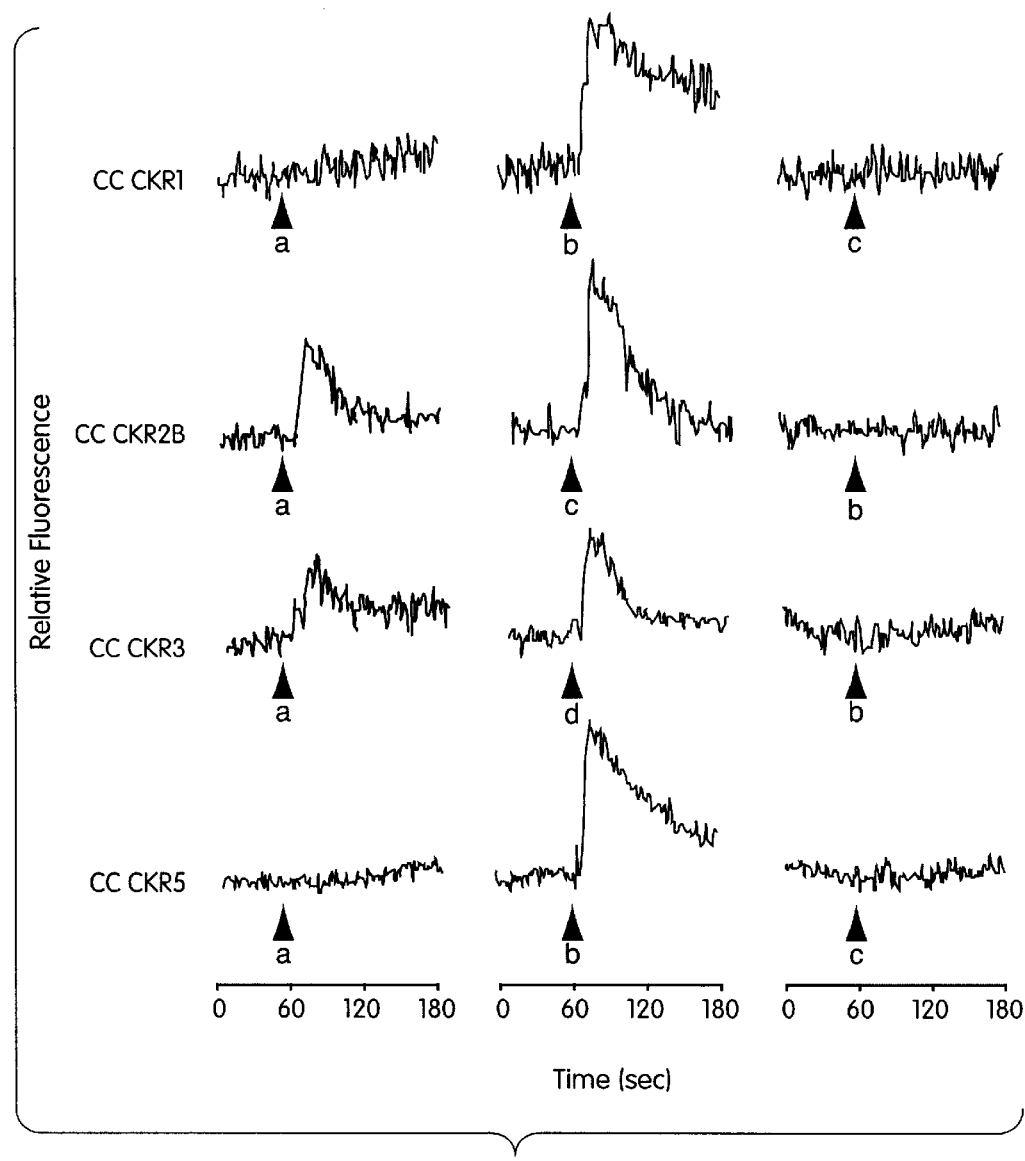

FIG. 12A is a series of tracings representing the selectivity of various chemokine receptors to MCP-4. Calcium flux was monitored by the relative fluorescence of fura-2-loaded HEK 293 cells stably expressing cloned CC chemokine receptors. Each row of tracings corresponds to the receptor indicated on the left. Arrows indicate the time of addition of the indicated chemokine at 50 nM (a=MCP-4, b=MIP-1α, c=MCP-1, and d=eotaxin).

Figures 1, 12B:
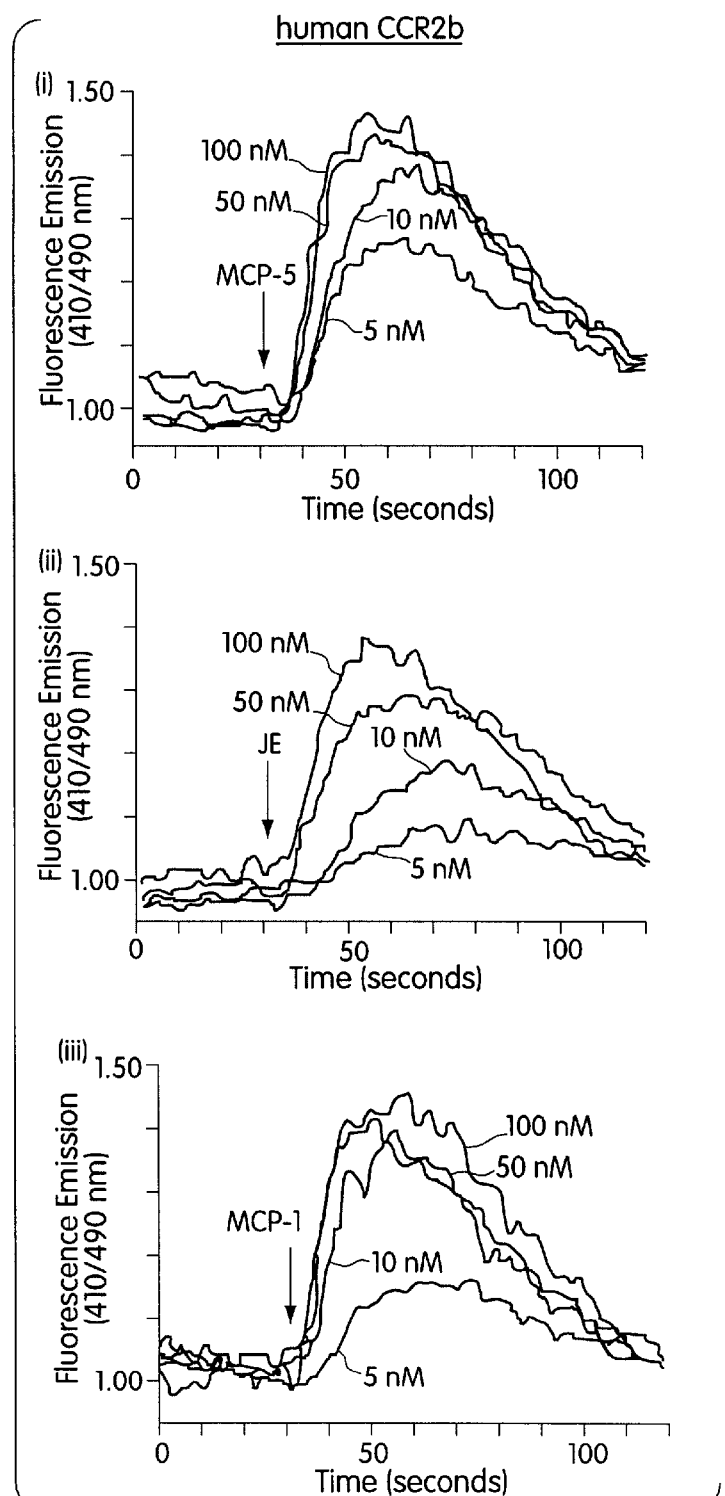
Figures 2, 12B:
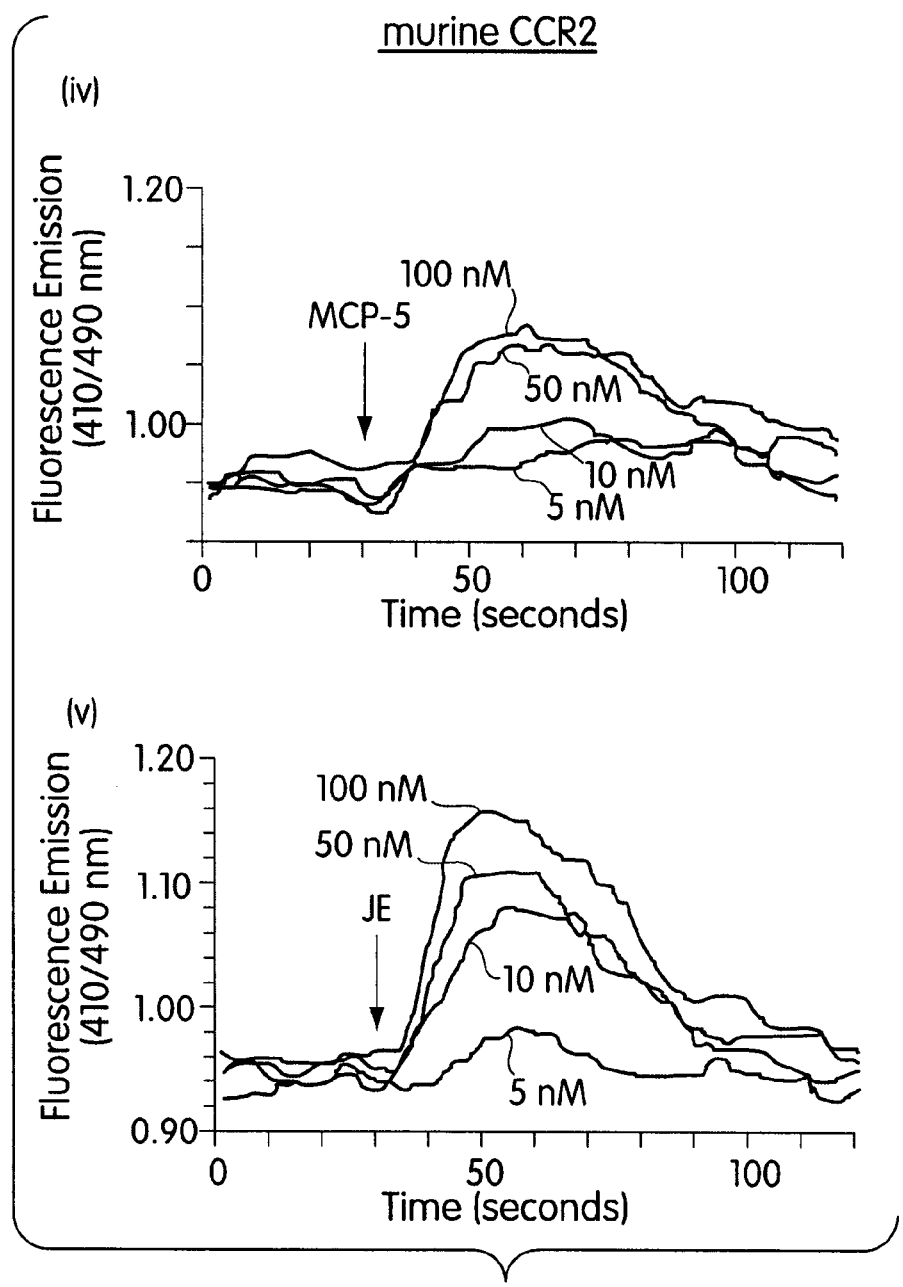

FIG. 12B is a series of line graphs that identify CCR2 as a functional MCP-5 receptor. HEK-293 cells stably expressing human CCR2b (i, ii, and iii) or murine CCR2 (iv, v) were loaded with indo-1 AM, and intracellular calcium concentrations were monitored by ratio fluorescence in response to the indicated concentrations of MCP-5 (i, iv), JE (ii, v), and MCP-1 (iii).

Figure 12C:
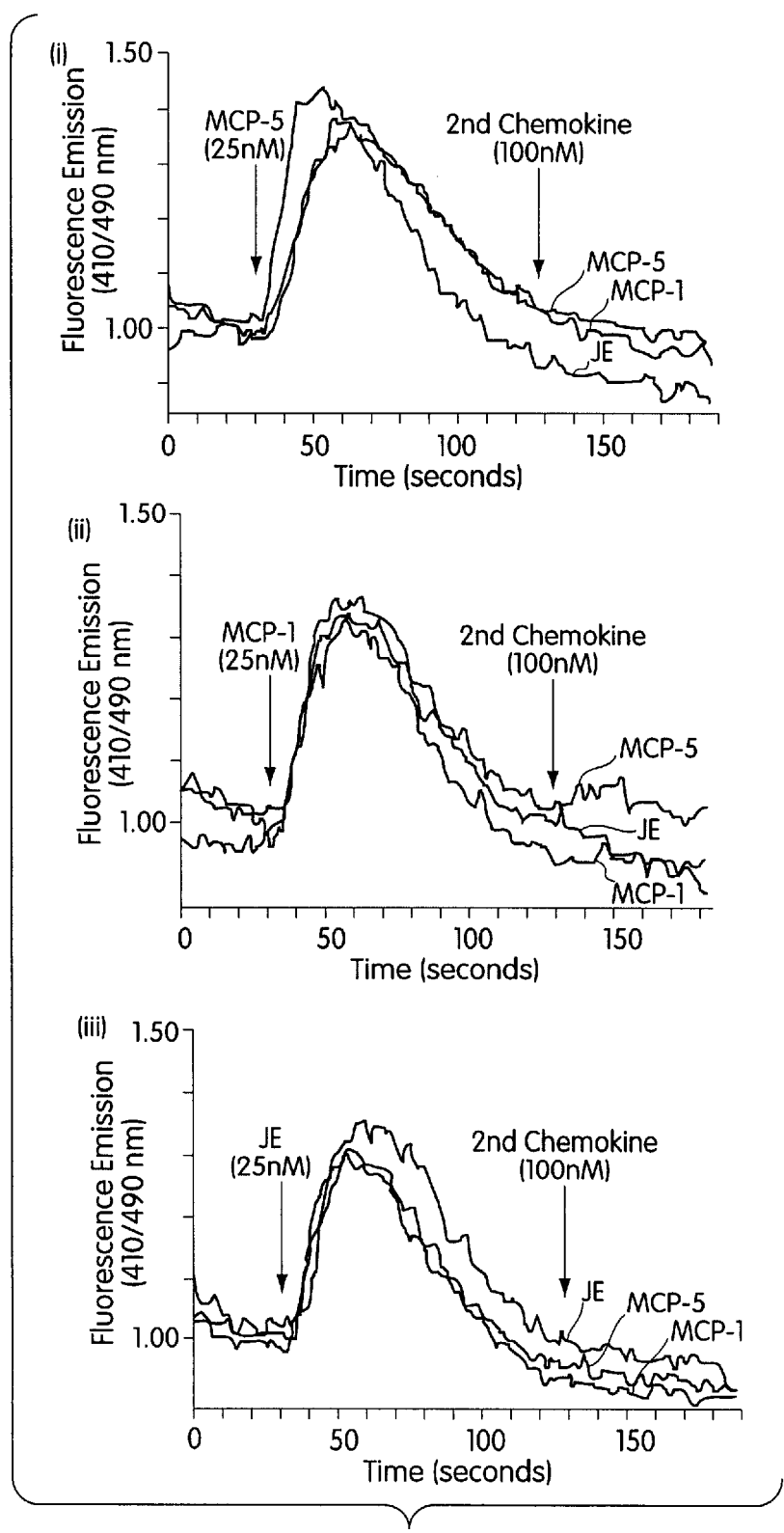

FIG. 12C is a series of line graphs that illustrate desensitization of CCR2b by MCP-5. HEK-293 cells stably expressing human CCR2b were exposed to MCP-5 (i), MCP-1 (ii), or JE (iii) and subsequently challenged with 100 nM MCP-5, 100 nM MCP-1, or 100 nM JE.

Figure 13:
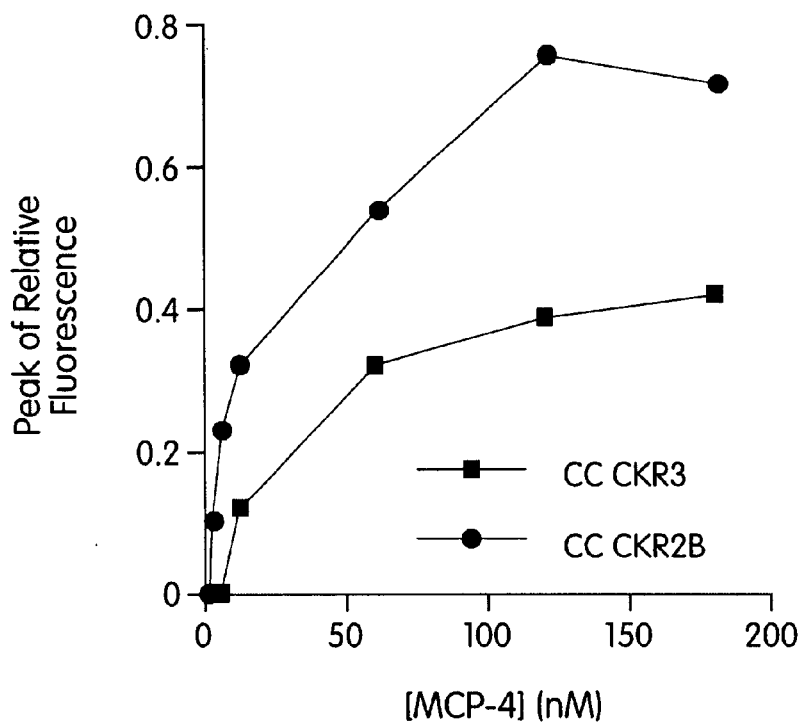

FIG. 13 is a line graph in which the magnitude of the calcium transient peak induced by MCP-4 is plotted as a percentage of the maximal response observed for MCP-1 in the case of CKR2b (circles) and eotaxin in the case of CC CKR3 (squares).

Figure 14A:
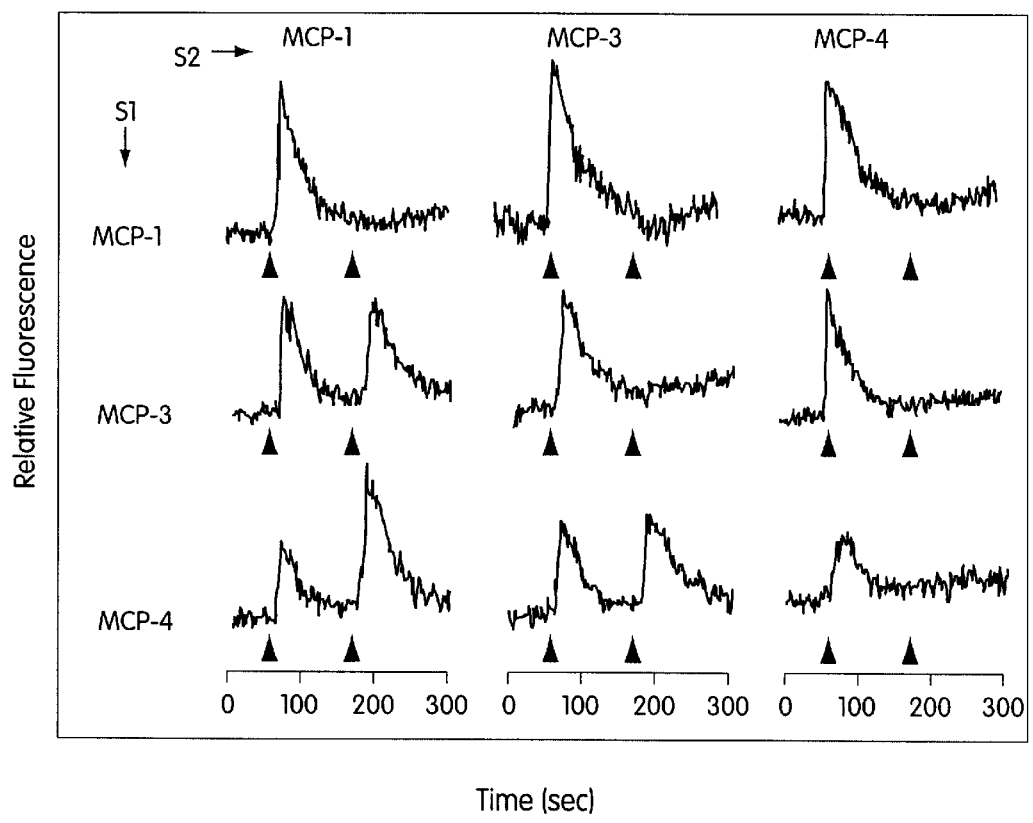

FIG. 14A is a series of tracings depicting desensitization of calcium transients in HEK 293 cells stably transfected with CKR2b. Relative fluorescence was monitored before and during sequential addition of chemokines at the times indicated by the arrows. The first stimulus added (S1) for each tracing is indicated at the left of the row in which it is found. The second stimulus added (S2) is indicated at the top of the column in which the tracing is found.

Figure 14B:
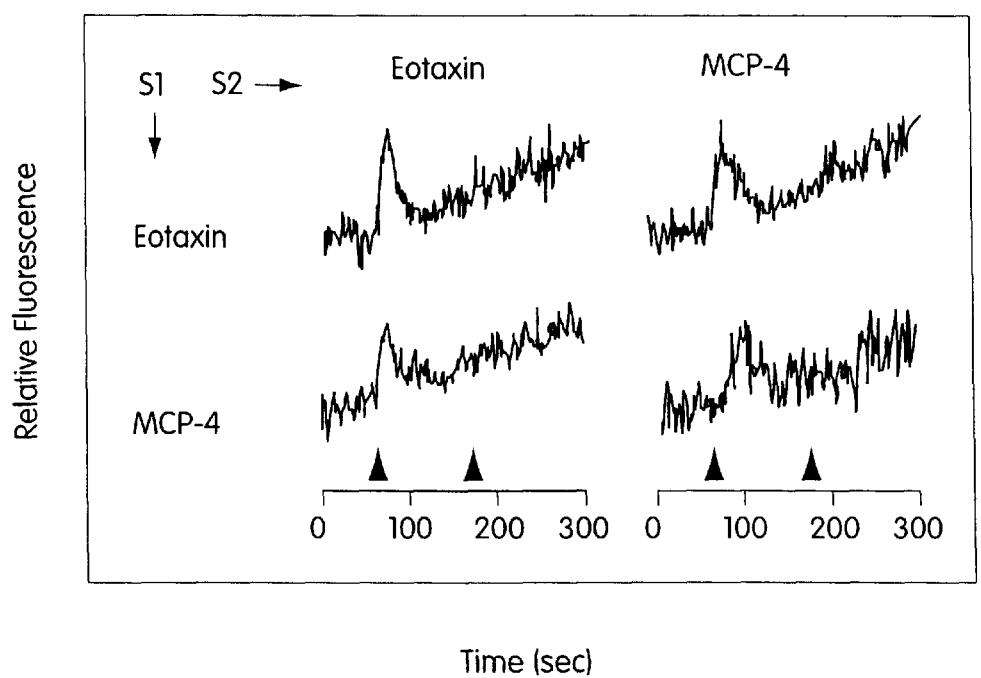

FIG. 14B is a series of tracings depicting desensitization of calcium transients in HEK 293 cells stably transfected with CKR3B. Fluorescence was monitored as described in the legend of FIG. 14A.

DETAILED DESCRIPTION

Two new members of the β-chemokine family, MCP-4 and MCP-5, have been isolated and characterized. The expression pattern of the genes encoding these chemokines was examined in normal tissue and in a variety of clinically relevant circumstances, such as in cytokine stimulated endothelial, epithelial, and hematopoietic cells, in hypertrophic sinus tissue, and in two in vivo models of pulmonary inflammation. In addition, the chemotactic activity of MCP-4 and MCP-5 proteins on various leukocytes, and the receptors through which this activity is exerted, are described.

The following examples are meant to illustrate, not limit, the invention.

EXAMPLE 1

Cloning of Human MCP-4 and MCP-5 cDNA

A. Isolation of the human MCP-4 gene

A human MCP-4 cDNA was isolated from a heart cDNA library using a human eotaxin genomic probe, as follows. A 1.1 kb genomic fragment of the human eotaxin gene containing exon 2 and the coding portion of exon 3 was $^{32}$P-labeled with the Klenow fragment of DNA polymerase and used to probe a λgt10 human heart cDNA library (Clontech, Palo Alto, Calif.). Approximately $10^6$ phage were plated, transferred to GeneScreen Plus (DuPont, Wilmington, Del.), and hybridized for 18 hours at 42° C. in a buffer containing 20 mM Tris (pH 7.5), 50% formamide, 10% dextran sulfate, 5×SSC, 1×Denhardt's solution (0.0002% (w/v) polyvinylpyrrolidone, 0.0002% (w/v) BSA, 0.0002% (w/v) Ficoll 400), and 100 mg/ml of heat-denatured herring sperm DNA solution. The filters were washed for 30 minutes at room temperature with 2×SSC and 0.1% SDS followed by a 30 minute wash at 60° C. with 0.2×SSC and 0.1% SDS. Eight hybridizing plaques were identified and purified. The inserts were amplified by the polymerase chain reaction (PCR) using a pair of λgt10 flanking primers. The PCR consisted of 30 thermocycles of 95° C. for 60 seconds (during which the DNA was denatured), 55° C. for 60 seconds (during which the primers annealed to the template), and 72° C. for 60 seconds (during which a complementary sequence was polymerized). The amplified PCR products were subcloned into a pCRII vector (Invitrogen, San Diego, Calif.), and the sequence of both strands was obtained using SEQUENASE™ (USB-Amersham, Arlington Heights, Ill.). Alignment of the DNA sequences and homology analysis was performed by using the CLUSTAL analytical program and the GAP program (Genetics Computer Group at the University of Wisconsin, Madison, Wis.).

The MCP-4 cDNA was 823 bp long, consisting of a 34 bp 5' untranslated region, a 297 bp coding region, and a 492 bp 3' untranslated region (FIG. 1A). A single AUUUA sequence was identified in the 3' untranslated region (FIG. 1A). This sequence motif has been shown to decrease the stability of cytokine mRNA (Shaw et al., Cell 46:659–667, 1986). The entire cDNA sequence of human MCP-4 was compared with the nucleotide sequence of the known human chemokines. MCP-4 was found to be 62%, 58%, and 57% identical to MCP-1, MCP-3, and eotaxin, respectively (Table 1). The nucleotide sequence of human MCP-4 was also compared to known mouse chemokines and found to be most homologous to eotaxin (57% identical), and 54% and 51% identical to MCP-3 and MCP-1, respectively.

TABLE 1

Homology of Human MCP4 with other Chemokines

| Chemokine | Identity (%) | Amino Acid Similarity (%) | Nucleic Acid Identity (%) |
|---|---|---|---|
| Hu MCP1 | 65 | 79 | 62 |
| Hu MCP2 | 57 | 70 | ND |
| Hu MCP3 | 65 | 77 | 58 |
| HU EOT | 66 | 76 | 57 |
| Hu RANTES | 32 | 57 | 41 |
| Hu MIP-1α | 39 | 54 | 45 |
| Hu MIP-1β | 39 | 61 | 41 |
| Hu-IL-8 | 28 | 53 | 27 |
| Mu MCP1 | 54 | 69 | 51 |
| Mu MCP3 | 53 | 70 | 54 |
| Mu EOT | 54 | 66 | 57 |
| Mu RANTES | 35 | 59 | 42 |

The human MCP-4 cDNA encodes a 99 amino acid protein containing a highly conserved 23 amino acid signal peptide (FIG. 1A). Signal peptidase cleavage is predicted to occur after the sequence, Pro-Gln-Gly-Leu-Ala, which is invariant in human MCP-1, -2, -3, and eotaxin (FIG. 2A). The resulting 76 amino acid sequence is predicted to have an N-terminal Gln, which is characteristic of the MCP family. The putative mature protein is predicted to have a molecular weight of 8,599 Da, a pI of 10, and appears to lack N-linked glycosylation sites. At the amino acid level, human MCP-4 exhibits 66%, 65%, 57%, and 65% identity with human eotaxin, MCP-1, MCP-2, and MCP-3, respectively, and has 54%, 54%, and 53% identity with mouse eotaxin, MCP-1 and MCP-3, respectively. Thus, human MCP-4 is as closely related to eotaxin as it is to proteins in the MCP family. However, in contrast to eotaxin, MCP-4 has an N-terminal Gln residue and it lacks the two amino acid N-terminal gap that is characteristic of the eotaxin proteins.

B. Isolation of the murine MCP-5 gene

Human MCP-4 cDNA was radiolabelled and used as a probe to screen a 129SV mouse genomic library (Stratagene, La Jolla, Calif.). Approximately $10^6$ phage were plated, transferred to GeneScreen Plus (DuPont, Wilmington, Del.), hybridized for 18 hours at 50° C. in a low stringency hybridization buffer (0.6M NaCl, 80 mM Tris-HCl, 4 mM EDTA, 0.1% (w/v) sodium pyrophosphate, 0.1% (w/v) SDS, 10×Denhardt's solution, 100 μg/ml denatured herring sperm DNA) at 50° C. and washed at 60° C. in 1×SSC/0.1% SDS. In order to exclude JE, the putative murine orthologue of human MCP-1, the filters were rehybridized as described with a full-length JE cDNA fragment and washed at 65° C. in 0.1×SSC/0.1% SDS. Fifteen plaques, which hybridized more strongly with the human MCP-4 probe than with the murine JE probe, were analyzed by PCR using two sets of degenerate oligonucleotides corresponding to highly conserved regions of murine and human CC chemokines and the MCP-eotaxin subfamily. The first set was designed to amplify Exon 1-2 and consisted of a 5' oligomer (5'-CTTCTGKGYCTGCTGYTCA-3'; SEQ ID NO:17) and a 3' oligomer (5'-ACAGCYTYYYDGGGACA-3'; SEQ ID NO:18). The second set was designed to amplify Exon 2-3 and consisted of a 5' oligomer (5'-

TGTCCCHRRRARGCTGT-3'; SEQ ID NO:19) and a 3' oligomer (5'-GSKTCAGCRCAGAYYTC-3'; SEQ ID NO:20). The reactions were heated to 95° C. for 5 minutes and then subjected to 30 rounds of the following thermocycle: 94° C. for 1 minute, 45° C. for 1 minute and 72° C. for 1.5 minutes. The final round of extension at 72° C. was prolonged to 8 minutes.

When the first set of primers was employed, five of the fifteen plaques were shown to contain DNA that was amplified as an 800 bp PCR product. These products were subcloned into the pCRII vector (Invitrogen, San Diego, Calif.) and sequenced (Sequenase Kit, United States Biochemical, Cleveland, Ohio). All five subclones contained novel, overlapping sequence that appeared to be homologous to members of the MCP subfamily.

In order to determine the complete structure of the MCP-5 cDNA, 5' and 3' RACE PCR was performed using RNA isolated from IFNγ-treated RAW 264.7 cells. The 5' and 3' ends of the cDNA for murine MCP-5 were isolated using a 3' oligonucleotide in exon 2 (5'-CTGGCTGCTTGTGATTCTCCTGT-3'; SEQ ID NO:21), a 5' oligonucleotide at the end of exon 1 (5'-CAGTCCTCAGGTATTGGCTGG-3; SEQ ID NO:22), and the Marathon™ cDNA Amplification Kit (Clontech, Palo Alto, Calif.). The amplified products were cloned into the pCR2.1 vector (In Vitrogen, San Diego, Calif.) and sequenced. Based on the sequence obtained, oligonucleotides capable of amplifying full-length cDNA from IFNγ-treated RAW cell poly A+ RNA were synthesized using the 5' oligomer 5'-AGCTTTCATTTCGAAGTCTTTG-3'(SEQ ID NO:23) and the 3' oligomer 5'-TAGATTCGGTTTAATTGGCCC-3'(SEQ ID NO:24). The products produced by PCR with these oligonucleotides were cloned into pCR2.1 and sequenced.

The cDNA was 514 bp long with an open reading from that encoded 104 amino acids. The 5' region of the cDNA encoded a 22 amino acid hydrophobic leader sequence whose cleavage site was predicted to occur at a position similar to the other MCPs and eotaxin (FIGS. 1B and 2B) resulting in a mature protein of 9.3 kDa with a pI of 9.4. The 3' untranslated region contained a single polyadenylation signal of a rare type also found in human eotaxin (ATTAAA) and four mRNA destabilization signals (ATTTA; FIG. 2B) that have been reported to decrease the mRNA stability of other cytokine mRNAs (Shaw et al., Cell 46:659–667, 1986).

The sequence of murine MCP-5 has been deposited with GenBank and assigned the accession number U66670. The sequence comparison shown in FIG. 2B was generated using the program SeqVu (from The Garvin Institute of Medical Research, Sydney, Australia). Sequences were aligned for maximal homology, using the positions of the four conserved cysteine residues as fixed points.

The sequence of murine MCP-5 is most homologous to human MCP-1. The percent amino acid/nucleic acid identity is shown in Table 2. These figures depict comparison of the open reading frames and the full length cDNAs using the GAP program (supplied by the Genetics Computer Group at the University of Wisconsin Madison, Wis.), which uses the algorithm of Needleman and Wunsch to maximize the number of matches and minimize the number of gaps in two complete sequences. ND indicates that the percent identity was not determined. Like human MCP-1, murine MCP-5 does not contain the additional serine/threonine rich glycosylated 49 amino acid C-terminal extension that JE uniquely possesses (FIG. 2B). MCP-5 is unique among the MCP proteins in that its N-terminal amino acid is predicted to by glycine, a feature that it shares with human eotaxin (FIGS. 1B and 2B).

TABLE 2

|  | mMCP5 | mJE | mMCP3 | mEot | hMCP1 | hMCP2 | hMCP3 | hMCP4 | hEot |
|---|---|---|---|---|---|---|---|---|---|
| mMCP5 |  | 47/50 | 58/57 | 49/53 | 66/64 | 56/ND | 60/62 | 56/58 | 58/59 |
| mJE | 47/50 |  | 49/54 | 49/51 | 52/63 | 53/ND | 52/52 | 54/51 | 49/50 |
| mMCP3 | 58/57 | 49/54 |  | 46/48 | 59/60 | 51/ND | 61/67 | 53/67 | 54/54 |
| mEot | 49/53 | 49/51 | 46/48 |  | 53/54 | 52/ND | 57/53 | 54/50 | 59/55 |
| hMCP1 | 66/64 | 52/63 | 59/60 | 53/54 |  | 62/ND | 74/66 | 65/61 | 71/63 |
| hMCP2 | 56/ND | 53/ND | 51/ND | 52/ND | 62/ND |  | 58/ND | 57/ND | 61/ND |
| hMCP3 | 60/62 | 52/52 | 61/67 | 57/53 | 74/66 | 58/ND |  | 64/58 | 70/63 |
| hMCP4 | 56/58 | 54/51 | 53/67 | 54/50 | 65/61 | 57/ND | 64/58 |  | 66/58 |
| hEot | 58/59 | 49/50 | 54/54 | 59/55 | 71/63 | 61/ND | 70/63 | 66/58 |  |

EXAMPLE 2

Gene Analysis and Chromosomal Location

A. Southern blot analysis of MCP-4

High molecular weight genomic DNA was isolated from human peripheral blood leukocytes (PBMCs), and separate samples were digested with one of four restriction endonucleases: PstI, HindIII, BglII, or EcoRI. Approximately 20 mg of digested DNA were electrophoresed on a 0.8% agarose gel, transferred to GeneScreen Plus, and hybridized for 18 hours at 42° C. with the MCP-4 cDNA probe described in Example 1. The blots were first washed at low stringency (2×SCC, 0.1% SDS, 50° C.) and then at high stringency (0.1×SSC, 0.1% SDS, 65° C.) for 30 minutes each. This analysis revealed that human MCP-4 is a single copy gene (FIG. 3A). Furthermore, under highly stringent hybridization and washing conditions, the MCP-4 cDNA can be used as a probe to uniquely detect MCP-4. Low stringency Southern blot analysis (FIG. 3B) revealed multiple bands, which represent closely related β-chemokine genes.

In order to determine the chromosomal location of the MCP-4 gene, PCR-based screening of the National Institute of General Medical Sciences (NIGMS) somatic cell hybrid panel #2 (available from the A.T.C.C., Rockville, Md.) was performed using MCP-4 specific oligonucleotide primers (5'-TCAGCCAGATGCACTCAACG-3' (SEQ ID NO.:25) and 5'-TGGAAAAGTCATTTCACGTA-3' (SEQ ID NO.:26)) from exons 2 and 3, respectively. The reaction was performed using 100 mg of template DNA, which was denatured initially at 94° C. for 2 minutes and then subjected to 30 repetitions of the following thermocycle: 94° C. for 30 seconds, 55° C. for 30 seconds, and 72° C. for 60 seconds. The reaction products were separated by electrophoresis on a 1% agarose gel, and visualized by staining with ethidium bromide.

Oligonucleotide primers specific for human MCP-4 genomic sequences were also used to amplify human, mouse, and hamster genomic DNA. No product was seen when rodent DNA was used. However, an ~850 bp product was observed in human genomic DNA and in a somatic cell hybrid line containing human chromosome 17 as its only human chromosome. The other rodent-human hybrid cell lines did not contain DNA that could be amplified with the designated primers. Thus, MCP-4 is located on human chromosome 17.

B. Southern blot analysis of MCP-5

Samples containing approximately 10 μg of mouse genomic DNA were digested separately with one of four restriction endonucleases: BamHI, EcoRI, XbaI, or HindIII. The digests were then electrophoresed through an agarose gel (0.8%), transferred to GeneScreen Plus™, hybridized under conditions of high stringency (50% formamide, 10% dextran sulfate, 5×SSC, 1×Denhardt's solution, 1% SDS, 100 μg/ml denatured herring sperm DNA, and 20 mM Tris at 42° C.) with a radiolabeled MCP-5 probe, and washed for 40 minutes at 55° C. in 0.2×SSC/0.1% SDS. The blot was then exposed to X-ray film. A scanned image of the resulting autoradiogram is shown in FIG. 3C. A schematic representation of the genomic organization of the mouse MCP-5 gene, including the intron-exon structure, selected restriction sites, and the mature mRNA is shown in FIG. 3D.

C. The chromosomal location of MCP-5

The chromosomal location of MCP-5 was determined by single-stranded conformational polymorphism (SSCP) analysis using a pair of PCR primers in intron 2 that detected a polymorphism when using DNA from C57BL/6J and *Mus spretus* mice (FIG. 3E). The 5' "sense" oligonucleotide used was 5'-TTACAGGTCAGGTCCCCTACT-3'(SEQ ID NO:27) and the 3' "anti-sense" oligonucleotide was 5'-CTCCTTATCCAGTATGGTCCTG-3' (SEQ ID NO:28).

A panel of genomic DNA from 94 interspecific backcross animals between (C57BL/6J X SPRET/Ei)F$_1$ X SPRET/Ei (Jackson BSS) was used to map the MCP-5 gene based on the SSCP polymorphism. The MCP-5 gene cosegregated with Scya7 (Fic) and Scya11 (eotaxin) in this cross, placing it between D11Mit markers 7 and 36 on Chromosome 11. A comparison with the consensus map from the Mouse Genome Database (FIG. 3F) revealed this to be the region of Chromosome 11 containing the CC chemokine gene cluster designated Scya1-11. The MCP-5 gene has been assigned the designation Scya12 (FIG. 3F). In FIG. 3F, the right-hand panel shows a segment of the central part of the map of chromosome 11 from the Jackson BSS cross described, containing approximately 1500 loci. The data are: proximal-Nos2-1 recombinant/94 animals (1.1+/−0.1 cM)-Scya12-2recombinants/94 animals (2.1+/−1.5 cM)-Mpmv4-distal. The left-hand panel of FIG. 3F shows the Mouse Genome Database consensus map, wherein the estimated relative positions of the loci are given at cM offset from the centromere. D11Mit4 is offset at 37, Scya1-11 is offset at 45.4, and D11Bir12 is offset at 53. Other CC chemokines are shown and referred to as Scyl-11.

EXAMPLE 3

MCP-4 and MCP-5 Gene Expression

A. MCP-4 mRNA Expression in Normal Human Tissue

In order to examine the expression of human MCP-4 in different tissues, Northern blot analysis was performed as follows. Northern blots of multiple human tissue samples were obtained from Clontech and hybridized in the buffer described in Example 1 at 42° C. for 18 hours. The blots were then washed with 0.2×SSC and 0.1% SDS at 65° C. for 60 minutes. In order to control for potential variations in the quantity of RNA loaded, the blots were stripped by washing with 0.1×SSC and 0.1% SDS at 90° C. for 60 minutes and rehybridized with either a human β-Actin probe or a glyceraldehyde-3 phosphate dehydrogenase (GADPH) cDNA probe (Clontech).

This analysis revealed an ~850 bp transcript that probably corresponds to the mature human MCP-4 mRNA. The highest levels of constitutive MCP-4 expression were observed in normal human small intestine, colon, and lung with lower but clearly detectable expression in heart, placenta, and thymus. Lower levels of expression were also seen in muscle, kidney, pancreas, prostate, liver, testis and ovary. However, no expression was detected in brain, spleen or peripheral blood leukocytes (FIG. 4A).

B. Expression of MCP-4 in Inflamed Human Nasal Tissue

To examine the possibility that MCP-4 plays a role in allergic inflammation, MCP-4 expression was analyzed by in situ hybridization of nasal tissue obtained from nine patients with sinusitis and from six normal controls. All patients were adults between the ages of 19–45, who were selected because the suffered from chronic sinusitis for more than one year, (Hamid et al., Proc. Natl. Acad. Sci. USA 84:6760–6764, 1987). Patients were given an allergy skin test and, based on the result, placed in either an allergic or non-allergic subgroup. Biopsies of 2–3 mm were obtained from the maxillary sinuses of patients with chronic sinusitis and nasal mucosal biopsy specimens were taken from the inferior and middle turbinates of the six control subjects. The tissue was fixed by immersion in 4% paraformaldehyde for 2 hours, washed, embedded, and cut into sections (each 8 μm thick) before processing for in situ hybridization.

In situ hybridization was performed as previously described (Hamid et al., J. Clin. Invest. 87:1541–1546, 1991; Hamid et al., J. Clin. Invest. 94:870–876, 1994). Briefly, $^{35}$S-labelled RNA probes coding for MCP-4 mRNA were applied to permeabilized tissue sections, and the cRNA-mRNA hybrid was visualized using autoradiography. To characterize the MCP-4 mRNA-positive cells, particularly the inflammatory cells, digoxigenin-labeled probes were used. In a blind study, the MCP-4 mRNA signal was assessed in at least two sections from each subject. The hybridization signal in the epithelium was presented as the percentage of positive epithelial cells within the total epithelium. The mRNA positive cells in the subepithelium were expressed as the mean number of positive cells/high power field (0.20 mm$^2$). As a negative control, sections were hybridized with sense probes or pretreated with RNase prior to hybridization with anti-sense probes.

The level of MCP-4 mRNA expression was significantly higher in the tissue obtained from patients with sinusitis (both in the epithelial and subepithelial tissue) than in the tissue obtained from unaffected individuals. A quantitative assessment of the MCP-4 mRNA-positive cells in these patients is shown in Table 3. There was not a significant difference between the expression of MCP-4 in the tissue obtained from individuals in the allergic and non-allergic groups. Most of the mRNA expression was localized to the epithelium, particularly the basal layer. Most of the positive cells among the inflammatory infiltrate were mononuclear cells with abundant cytoplasm, a feature that is consistent with macrophage morphology. There were other positive cells, however, including small mononuclear cells, which could be lymphocytes, and granulocytes, which could be either eosinophils or neutrophils.

TABLE 3

| Tissue studied | No. of cases studied | Mean % epithelium + ve for MCP-4 mRNA | Mean no. of inflammatory cells/field + ve for MCP-4 mRNA in the subepithelium |
| --- | --- | --- | --- |
| Allergic sinusitis | 4 | 71.8 ± 10.7 | 12 ± 1.5 |
| Non-allergic sinusitis | 5 | 77.5 ± 10.0 | 13.3 ± 1.3 |
| Normal control | 6 | 14.6 ± 3.8 | 3.4 ± 0.3 |

C. MCP-5 Expression in Normal Murine Tissue and Murine Cell Lines

RNA was isolated from the organs of BALB/c mice by lysing the tissue in guanidinium isothiocyanate and pelleting the RNA through a 5.7 M $CsCl_2$ cushion (Chirgwin et al., Biochem. 18:5294–5299, 1979). The polyA$^+$ fraction was isolated from total RNA by oligo-dT cellulose chromatography (Pharmacia, Piscataway, N.J.). RNA STAT-60 (Tel Test-B Inc., Friendswood, Tex.) was used to isolate RNA from mouse leukocytes and cell lines.

To generate a Northern blot, 10 µg of total RNA was fractionated on a 1.2% agarose gel containing 0.7% formaldehyde and transferred to a GeneScreen™ membrane. The membrane was then exposed to $^{32}$P-dCTP-labeled MCP-5 or JE cDNA probes under hybridization conditions. A probe for the ribosomal protein rpL32 (Shen et al., Proc. Natl. Acad. Sci. USA 89:8240–8244, 1992) was used as a control for the quantity of RNA loaded. Hybridization was performed under conditions of high stringency, and the membrane was washed at 55° C. in 0.2×SSC, 0.1% SDS for 40 minutes. SVEC cells, from an SV40 virus-immortalized murine endothelial cell line and RAW 264.7 cells (American Type Culture Collection, Rockville, Md.) were cultured for 6 hours or 18 hours in DMEM supplemented with 10% iron fortified calf serum (without additions) that contained either 200 U/ml recombinant murine IFNγ (Genentech Inc., San Francisco, Calif.), 5 ng/ml recombinant murine IL-1β (Genzyme, Cambridge, Mass.), or 10 ng/ml recombinant murine IL-4 (Genzyme, Cambridge, Mass.). Mouse bone marrow-derived mast cells were obtained by culturing mouse bone marrow from FVB mice in the presence of 50% WEHI-3-conditioned medium for 4 weeks. Mast cells were sensitized with IgE anti-TNP at 50 µg/ml and either stimulated with TNP-BSA at 100 µg/ml for 4 hours at 37° C. or treated with 2.5 mg/ml of concanavalin A (ConA) for 4 hours at 37° C.

The procedures described above revealed an approximately 550 bp transcript that corresponds to the mature mouse MCP-5 mRNA. The highest levels of constitutive MCP-5 expression were observed in normal lymph nodes. MCP-5 mRNA was also seen in heart, lung, breast, salivary glands, thymus, colon, kidney, small intestine, and brain (the salivary gland and breast tissue contained lymph nodes). In contrast, no expression was detected in spleen, skeletal muscle, bone marrow, liver, or peripheral blood leukocytes (FIG. 4B).

The expression of MCP-5 and JE were compared in the mouse tissues listed above because these proteins have similar biological profiles and bind the same receptor. The highest constitutive expression of JE was seen in the salivary gland with low levels detected in other organs, such as lymph nodes. The 550 and 800 bp JE transcripts correspond to known 3' splice variants (Kawahara et al., J. Biol. Chem. 264:679–682, 1989).

As shown in FIG. 4C, MCP-5, JE, and rpL32 expression was also examined in subsets of leukocytes. RNA was isolated from eosinophils purified from the spleens of CD5-IL5 transgenic mice (Eos), bone marrow-derived mast cells that were either untreated (Ctl) or stimulated with either IgE (anti-TNP and TNP-BSA (IgE)), or ConA (ConA). In addition, RNA was harvested from resident peritoneal macrophages (RMΦ), elicited peritoneal macrophages (EMΦ; 76% MNC, 24% PMN), and elicited peritoneal neutrophils (ENΦ; 95% PMN, 5% MNC). Blots were hybridized and washed sequentially under conditions of high stringency with MCP-5, JE and rpL32 cDNA probes and exposed for 14 days, 3 days, or 18 hours, respectively.

No expression was detected in eosinophils, bone marrow-derived mast cells, or resident peritoneal macrophages. Furthermore, stimulation of these mast cells with either IgE or ConA did not induce MCP-5 expression. However, ConA induced the expression of JE (FIG. 4C) and both IgE and ConA treatment induced expression of murine CCRI (Gao et al., Biochem. Biophys. Res. Comm. 223:679–684, 1996). Activated macrophages, which were elicited in the peritoneal cavity by treatment with thioglycolate, expressed significant levels of MCP-5 mRNA. Neutrophils, which were elicited in the peritoneal cavity by treatment with sodium casein, also appeared to express MCP-5 mRNA. MCP-5 mRNA was not detected in either an unstimulated or stimulated allogeneic cytolytic CD8$^+$ T cell clone.

The ability of various stimuli to induce MCP-5 mRNA in the RAW264.7 macrophage cell line was evaluated because it appeared that activated macrophages were a primary source of MCP-5 mRNA. RNA was harvested from cells that were either untreated or treated for 18 hours with interferon-γ (IFNγ at 200 U/ml), or LPS (lipopolysaccharide) at 0.1, 1.0, 10, or 100 ng/ml. The RNA was then analyzed on Northern blots that were hybridized with MCP-4, JE, and rpL32 cDNA probes, washed sequentially under conditions of high stringency, and exposed for 7 days, 3 days, and 18 hrs, respectively.

The expression of MCP-5 was also examined in cytokine-stimulated murine endothelial cells (SVEC cells). MCP-5 was not induced in SVEC cells by IFNγ, IL-4 (10 ng/ml), or IL-1β (5 ng/ml), while JE was induced by IFNγ and IL-4 (FIG. 4D) and eotaxin was induced by IFNγ (Rothenberg et al. Proc. Natl. Acad. Sci. USA 92:896–8964, 1995). JE was similarly expressed in activated macrophages and induced in RAW cells by LPS and IFNγ (FIG. 4D).

D. MCP-5 mRNA Expression in Murine Models of Pulmonary Inflammation

In order to determine whether MCP-5 is associated with the immune response in vivo, MCP-5 expression was examined in the lungs of mice that had been infected with *Nippostronylus brasiliensis* and in a murine model of OVA-induced pulmonary inflammation (FIG. 4C).

The *N. brasiliensis* model was generated as described by Coffman et al. (Science 245:308–310, 1989). Briefly, twelve week old female BALB/cJ mice were injected with 750 third stage *N. brasiliensis* larvae, their lungs were harvested 7, 10 or 14 days later, and RNA was extracted from the tissue and analyzed by Northern blotting. The level of MCP-5 mRNA was markedly increased by day 7. The expression level peaked on day 10 and returned to control levels by day 14. MCP-5 mRNA accumulation preceded the peak recruitment of pulmonary macrophages, neutrophils, and eosinophils that characterize the granulomatous immune response to this pathogen (Coffman et al., supra).

The aerosolized OVA model is generated as follows (see also MacLean et al., J. Exp. Med., in press, 1996). BALB/cJ mice that were between 5 and 10 weeks old were immunized with 10 μg of OVA (Sigma Chemical Co., St. Louis, Mo.) and 1 mg of aluminum hydroxide (via an intraperitoneal injection) on days 0, 7, and 14. Control mice were "sham-immunized" by treatment with aluminum hydroxide only. An aerosol challenge with OVA (50 mg/ml in sterile sale) was administered 7–10 days after the final immunization. The mice were sacrificed 3, 6, 24, or 48 hours after the aerosol challenge, their lungs were harvested, and RNA was extracted from the tissue. At least 3 mice were present in each group and at each time point of harvest.

MCP-5 mRNA was detected in the OVA-immunized mice 3 hours after aerosol challenge (FIG. 4C; left-most lane labeled IC) and remained at an elevated level at the 48 hour time point (right-most lane labeled IC). In contrast, MCP-5 mRNA in challenged, sham-immunized mice (SC) remained at the same level as before the aerosol challenge. In this model, as following infection with *N. brasiliensis*, the accumulation of MCP-5 mRNA preceeded the peak accumulation of pulmonary macrophages, lymphocytes and eosinophils that characterize the immune response.

Expression of JE was also elevated in both models of pulmonary inflammation. However, in the OVA model, levels of JE mRNA returned to baseline by 48 hours but MCP-5 levels remained elevated.

EXAMPLE 4

Cytokine Regulation of MCP-4 in Endothelial and Epithelial Cells

RNA was isolated from cultured cells using RNA-STAT 60 (Tel Test-B Inc., Friendswood Tex.), according to the manufacturer's recommendations. Total RNA (20 mg) was fractionated on a 1.2% agarose gel containing 0.2 M formaldehyde, transferred to GeneScreen™, and hybridized with $^{32}$P-dCTP Klenow-labeled, random primed probes. A human MCP-1 probe was generated from a full length human MCP-1 cDNA isolated from a human lung library (Clontech), and the template for a human vascular cell adhesion molecule-1 (VCAM-1) probe was as described in Cybulsky et al. (Am. J. Pathology, 138:815–820, 1991).

The capacity of human umbilical cord endothelial cells (HUVEC) to express MCP-4 mRNA was evaluated as follows. Human umbilical vein endothelial cells (HUVEC) were obtained at passage two from Clonetics (San Diego, Calif.) and treated at passage three with the following cytokines: IL-1α (5 ng/ml), IL-4 (20 ng/ml), IFNγ (100 ng/ml), and TNFα (10 ng/ml; all cytokines were obtained from Genzyme, Cambridge, Mass.).

These cells had no detectable constitutive MCP-4 expression, but IL-1α, TNFα and, to a lesser extent, IFNγ stimulated the accumulation of MCP-4 mRNA within six hours. These levels decreased within 18 hours of stimulation (FIG. 5A). In contrast to MCP-1 expression, the expression of human MCP-4 was not significantly increased in HUVECs by stimulation with IL-4 (FIG. 5A). TNFα and IFNγ acted synergistically, and IL-4 prolonged the TNFα-induced accumulation of eotaxin mRNA. Human MCP-1 and human vascular cell adhesion molecule (VCAM-1) were used as controls for HUVEC's responsiveness to the cytokines tested, and β-actin was used as a control for RNA loading (FIG. 5A).

The ability of two respiratory epithelial cell lines, BEAS-2B and A549, were also tested for their ability to express MCP-4 mRNA in response to cytokine stimulation. These cells were maintained in Dulbecco's Modified Eagle's Medium (DMEM)/F-12 (BEAS-2B) and F12K (A549) medium. Epithelial cells grown to confluence were stimulated with increasing doses of either IL-1β, TNFα, or IFNγ, or with 10 nM phorbol 12-mysristate 13-acetate (PMA), transforming growth factor-α (TGFα; 10 ng/ml) or TGFβ (10 ng/ml). Human cells U937 and HL60 were obtained from the American Type Culture Collection (A.T.C.C., Rockville, Md.) and maintained in DMEM. MCP-4 mRNA expression was not detected by Northern analysis in A549 cells in the absence of cytokine stimulation. However, stimulation of the cells with 0.1 ng/ml of IL-1β or 10 ng/ml of TNFα for 4 hours induced the accumulation of a distinct ~850 bp MCP-4 mRNA species (FIG. 5B). The addition of 10 nM PMA to the medium was associated with the presence of a faint but detectable MCP-4 mRNA signal. However, MCP-4 mRNA was not detected after 4 hours of stimulation with 10 ng/ml IFNγ, 10 ng/ml TGFα, or 5 ng/ml TGFβ (FIG. 5B). Treatment of A549 cells with 10 ng/ml of TNFα induced maximal MCP-4 mRNA expression at four hours, which declined over the subsequent 48 hours (FIG. 5C). Identical results were obtained for IL-1β-induced accumulation of MCP-4 in A549 cells. Likewise, the addition of TNFα similarly increased MCP-4 mRNA expression in BEAS-2B cells six hours after stimulation, with decreasing levels after 18 hours of stimulation (FIG. 5D). IFNγ acted synergistically with TNFα and IL-1 to induce MCP-4 mRNA accumulation in both BEAS-2B cells (FIG. 5D) and A549 cells. Furthermore, while IL-4 alone did not induce a detectable expression of MCP-4 in the BEAS-2B line, it clearly acted synergistically with TNF, IL-1 and IFNγ (FIG. 5D).

EXAMPLE 5

Expression of MCP-4 in Leukocytes

The expression of eotaxin mRNA was examined in U937 cells, a monocytic tumor line, in HL60 cells, a myelocytic tumor line, and in peripheral blood leukocyte subtypes by the method described in Example 4. U937 cells constitutively expressed MCP-4 mRNA, which was unaffected by IFNγ treatment (FIG. 6A). MCP-4 mRNA was undetectable by Northern blot analysis of total RNA in untreated HL60 cells. However, there was a detectable MCP-4 signal in an eosinophilic subline of HL60 (available from the A.T.C.C., Rockville, Md.). These cells were maintained in Iscove's Modification of DMEM supplemented with 0.5 mM butryic acid (Sigma Chemical Co., St Louis, Mo.) as described by Tomonaga et al., 1986). The medium was supplemented with 10% iron-fortified calf serum (MediaTech, Hendon, Va.), 50 U/ml penicillin, 50 mg/ml streptomycin, and 2 mM L-glutamine. Peripheral blood mononuclear cells, peripheral blood neutrophils, untreated peripheral blood eosinophils, peripheral blood eosinophils cultured in the presence of IL-3 for 3 days, Jurkat and H9 T cells, and RM3 B cells did not express detectable MCP-4 mRNA (FIGS. 6A, 6B, and 6C). However, MCP-4 mRNA was detected in peripheral mononuclear cells cultured in the presence of PHA and IL-2 for 3 days (FIG. 6B). While three HIV-specific cytolytic CD8$^+$ T cell clones induced the expression of RANTES upon activation with an anti-CD3 monoclonal antibody, MCP-4 mRNA was not detected (data for one of the three clones tested is shown in FIG. 6B).

EXAMPLE 6

Generation of Biologically Active Recombinant Human MCP-4 Protein

To examine the biological properties of human MCP-4, the protein was expressed and purified from COS cells and *E. coli* cells.

A. Production of Recombinant MCP-4 in E. coli

DNA encoding recombinant human MCP-4, beginning with the putative mature amino-terminal glutamine at position 24 and ending with the carboxy terminal threonine at position 98, was amplified by PCR using the human MCP-4 cDNA as a template. The oligonucleotide primers used were designed to amplify a sequence that contained BamHI sites on both ends, and that would encode a protein with an amino-terminal factor Xa site (IEGR). Amplified cDNA was subsequently sub-cloned using a TA cloning kit (Invitrogen) and sequenced. The construct was liberated by BamHI digestion, cloned into the BamHI sites of vector PQE8 (Qiagen Inc, Chatsworth, Calif.), and then transformed into the E. coli strain M15. Expression of MCP-4 in pQE8 resulted in a fusion protein containing an amino-terminal Met-Arg-Gly-Ser-(His)$_6$ (SEQ ID NO.:29) tag, which was purified essentially as described (Rothenberg et al. Mol., Med. 2:334–348, 1996), with the following minor modifications. Recombinant M15 E. coli containing the PQE8 plasmid engineered to express human MCP-4 were induced with isopropyl β-D-thiogalactopyranoside (IPTG) for 2 hours. Following centrifugation, the bacterial pellet was resuspended in 50 mM Tris (pH 8.0), 0.2 M NaCl, 2 mM EDTA, 0.1 mM PMSF, 1 mM benzamidine, and 5 mM β-mercaptoethanol at 5 ml/gram of wet bacteria. Lysozyme was added to a final concentration of 0.2 mg/ml and the bacterial suspension was incubated on ice for 20 minutes. Triton-X-100 was then added to 1%, and the incubation was resumed for an additional 10 minutes. The suspension was sonicated on ice and centrifuged at 10,000×g for 20 minutes at 4° C. The pellet was resuspended 6 M guanidine HCl, 0.1 M sodium phosphate and 0.01 M Tris HCl (pH 8.0), and applied to a nickel-NTA chromatography column (ProBond", Invitrogen) as described (Rothenberg et al., Mol. Med. 2:334–348, 1996). Recombinant MCP-4 was eluted from the column with 8 M urea buffer (described above) at pH 8.0 containing 0.25 M imidazole. The protein was further purified by high pressure liquid chromatography (HPLC) on a C4 reverse phase semi-preparative column (#214TP510, Vydac, Hesperia Calif.). Buffer A consisted of Milli Q dH$_2$O/0.1% trifluoroacetic acid (TFA), and buffer B consisted of 95% acetonitrile/0.1% TFA. The sample was loaded in 10% buffer B and run on a linear gradient on a Waters HPLC system. The gradient went from 10% to 20% buffer B over 5 minutes, and from 20% to 90% buffer B over 27 minutes. MCP-4 eluted at ~40% buffer B. Fractions corresponding to peaks on the chromatogram were collected and analyzed by SDS-PAGE to ascertain which peak represented human MCP-4. Once this was established, the sample was lyophilized, resuspended in factor Xa buffer (20 mM Tris-HCl, 100 mM NaCl, 2 mM CaCl$_2$, pH 8.0) containing 1 M Urea, and digested for 2 hours at room temperature with factor Xa (Boehringer Mannheim, Indianapolis, Ind.) at an enzyme/protein weight ratio of 1:10. The digested protein was repurified by reverse phase HPLC using the same conditions as above, lyophilized, and resuspended in H$_2$O. The concentration of purified MCP-4 protein was determined by comparing the optical density (OD) at 550 nm to a dilution series of bovine serum albumen, following addition of the BCA reagent (Pierce, Rockford, Ill.).

B. MCP-4 Expression in COS Cells

To express MCP-4 in COS cells, PCR primers were designed to amplify the coding region of human MCP-4 plus a 30 nucleotide sequence encoding a 2 amino acid spacer followed by the 10 amino acid FLAG epitope (GSDYKDDDDK; SEQ ID NO:30). The 30 nucleotide extension was located immediately upstream from the MCP-4 stop codon. The resulting PCR product was sub-cloned into the pCDNA1/Amp$^R$ vector, sequenced, and transfected into COS cells using DEAE-dextran, according to standard methods. Following transfection, cells were maintained in DMEM supplemented with 1% FCS for four days, after which time the supernatant was harvested and centrifuged at 1,000×g for 15 minutes. MCP-4-FLAG was purified from the supernatant by affinity chromatography using an anti-FLAG monoclonal antibody (M2) column (Eastman Kodak Co., New Haven, Conn.) at 4° C. After washing the column with TBS (50 mM Tris-HCl, 15 mM NaCl, pH 7.4) the recombinant MCP4-FLAG protein was eluted with 0.1 M glycine hydrochloride, pH 3.5 and immediately neutralized with 1 M Tris, pH 8.0. The eluted protein was concentrated by ultrafiltration using Centricon 3 (Amicon, Danvers, Mass.) and dialyzed into phosphate buffered saline, pH 7.4. Recovered protein was quantified using the BCA Protein Assay Reagent (Pierce, Rockford, Ill.), and approximately 100 ng of protein was electrophoresed into a Tris/Tricine 12.5% SDS-polyacrylamide gel under reducing conditions. The gel was electrotransferred onto a PVDF membrane (Dupont, Boston, Mass.) and analyzed by Western blotting using an anti-FLAG M2 monoclonal antibody followed by a horseradish peroxidase-conjugated sheep anti-mouse antibody. (Kirkegard & Perry, Gaithersburg, Md.) and developed by chemiluminescence (Dupont, Boston, Mass.).

The MCP-4 cDNA was engineered into the pCDNA-I/Amp expression vector, which bears a C-terminal FLAG tag, and used to transiently transfect COS cells. The supernatant of these cells provided a source of MCP-4 protein that was produced and processed by eukaryotic cells. The FLAG epitope was used to detect and purify MCP-4 from the COS cell supernatant (FIG. 7A, lane 4). MCP-4 was expressed in E. coli as a fusion protein containing an N-terminal histidine tag separated from the predicted mature N-terminal Gln of MCP-4 by a factor Xa consensus site. This strategy was employed to generate MCP-4 protein with the predicted mature N-terminus; the presence of an unmodified amino-terminal amino acid is critical for the biological activity of MCP-1 and eotaxin. Following nickel affinity chromatography and reverse phase HPLC chromatography, the purified MCP-4 protein (with the tag) migrated as a doublet with an apparent Mr of ~10–12 kDa when electrophoresed in a denaturing polyacrylamide gel (FIG. 7A, lane 1). This material exhibited no activity in an assay for monocyte chemotaxis (FIG. 7B), even at 1000 ng/ml. Therefore, the purified histidine tagged-MCP-4 protein was subjected to factor Xa digestion. Analysis by SDS-PAGE of the factor Xa digested (his)6-tagged MCP-4 protein revealed that the doublet had been converted to a smaller doublet migrating at ~8–9 kDa. This change in size is consistent with removal of the six N-terminal histidines. Two additional digestion products were also seen migrating at ~6 kDa and ~4 kDa. The factor Xa digested MCP-4 protein was repurified by reverse phase HPLC and tested on elutriated peripheral blood monocytes. The uncut MCP-4 protein had no chemotactic activity, while the factor Xa cut MCP-4 protein exhibited potent and dose-dependent monocyte chemotactic activity (FIG. 7B). Due to the fact that additional cleavage of MCP-4 by factor Xa could not be suppressed, subsequent experiments (presented in the Examples below) utilized MCP-4 produced by PeproTech (Rocky Hill, N.J.). Sequence analysis confirmed that this material was a single molecular species containing the mature N-terminal Gln. However, in the Tris/Trice SDS-PAGE gels system, this material also migrated as a doublet at ~8 kDa with a dimer apparent at ~16 kDa (FIG. 7A, lane 2).

Translation of human MCP-4, beginning with the putative N-terminal Gln residue, predicts an 8,599 Da protein. MCP-4 produced by E. coli migrates at ~8 kDa on a 12.5% Tris/Tricine SDS-polyacrylamide gel, while MCP-4-FLAG migrates at ~9 kDa. MCP-4 has no consensus sites for N-linked glycosylation, but it may contain O-linked carbohydrates and sialic residues. However, since the MCP-4-FLAG contains 10 more amino acids at the carboxy terminus than the MCP-4 produced by E. coli, it is likely that MCP-4 is not heavily glycosylated, and may not be glycosylated at all. In addition, MCP-4 seems to aggregate, as evidenced by the dimer that appears on the Coomassie stained gel.

EXAMPLE 7

Induction of Chemotaxis

A. MCP-4 Induced Monocyte and Eosinophil Chemotaxis

The chemotactic activity of the recombinant human MCP-4 protein was tested on primary human monocytes, neutrophils and eosinophils as follows. Fifty ml of replicate cells at $2 \times 10^6$ cells/ml for eosinophils, $1.0 \times 10^6$ cells/ml for neutrophils, and $5 \times 10^6$ cells/ml for mononuclear cells and monocytes in HBSS buffer (MediaTech) supplemented with 0.05% low endotoxin BSA (Sigma Chemical Co., St Louis, Mo.), were placed in the top wells of a 48 well micro-chemotaxis chamber (NeuroProbe, Inc., Cabin John, Md.; Falk et al., J. Immunol. Methods 33:239–247, 1980). A standard 5-$\mu$m pore polycarbonate filter (eosinophils and monocytes) and a polyvinylpyrrolidone-free 3-$\mu$m pore polycarbonate filter (neutrophils) separated the cells from buffer alone (30 ml), buffer containing recombinant chemokines, or affinity purified FLAG-tagged MCP-4 protein. Cells were incubated at 37° C. (60 minutes for eosinophils, 30 minutes for neutrophils, and 90 minutes for mononuclear cells and monocytes). The cells that migrated across the filter and adhered to the bottom side were stained with Diff-Quick (Baxter Scientific, McGaw Park, Ill.), and the number of cells per 400× field were counted.

MCP-4 exhibited chemotactic activity at concentrations comparable to other chemotactic MCPs, and this activity was as robust as the peak chemotactic responses elicited by these MCPs. However, the other MCPs did begin to exhibit a reproducible chemotactic response at ~5–10 ng/ml, while 50 ng/ml of MCP-4 was required to detect a consistent chemotactic response, and the peak MCP-4 effect was seen at 100–1000 ng/ml. This response was observed for both purified monocytes (FIG. 8) and monocytes recruited from a mononuclear cell preparation (FIG. 9A). MCP-4 was also chemotactic for human peripheral blood eosinophils in a dose-dependent manner (FIG. 9B). There was variability in the magnitude of the eosinophil chemotactic response from donor to donor when compared to eotaaxin, and variability in the dose-response, but purified eosinophils from all donors tested (n=5) responded to MCP-4. In contrast, recombinant MCP-4 did not elicit chemotaxis from human neutrophils, which responded strongly to IL-8 (FIG. 9C). Recombinant MCP-4 FLAG protein was also chemotactic for human peripheral blood monocytes and eosinophils, but not neutrophils. Therefore, potential post-translational modifications of MCP-4 and the carboxy-terminal FLAG epitope do not significantly affect the chemotactic activity of MCP-4.

B. MCP-5 Induction of Leukocyte Chemotaxis

Murine eosinophils, macrophages, and neutrophils and human mononuclear cells were suspended in HBSS with 0.05% BSA at 2.5, 5, 1, and $5 \times 10^6$ cells/ml, respectively, and replicate cells were placed in the top well of a 48 well micro-chemotaxis chamber (Neuro Probe, Inc. Cabin John, Md.). A polycarbonate filter with 5-$\mu$m pores (eosinophils, macrophages, and mononuclear cells) and a PVP-free filter with 3-$\mu$m pores (neutrophils) separated the cells from buffer alone or buffer containing purified recombinant murine eotaxin, human MCP-1, human IL-8 (PeproTech, Rocky Hill, N.J.) or murine MIP1$\alpha$, murine MIP-1$\beta$, murine JE, murine KC (R&D Systems, Minneapolis, Minn.). Murine MCP-5 was expressed and purified from E. coli by PeproTech, Inc. as the predicted mature 82 amino acid protein beginning with the N-terminal glycine. N-terminal sequence analysis of the purified recombinant MCP-5 preparation confirmed its homogeneity and the N-terminal glycine. Cells were incubated at 37° C. for 30 minutes (neutrophils), 60 minutes (eosinophils) or 90 minutes (macrophages and mononuclear cells) and the cells that migrated across the filter and adhered to the bottom side of the filter were stained with Diff-Quick (Baxter Scientific, McGaw Park, Ill.).

Figure 9D:
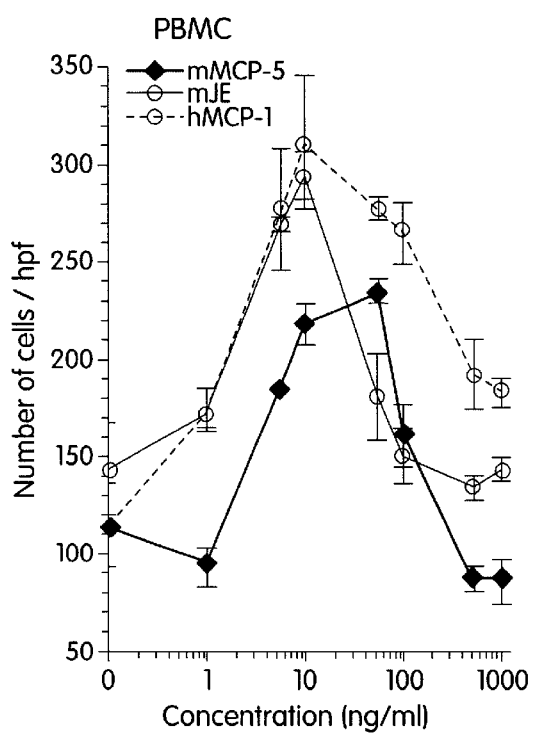
Figure 9E:
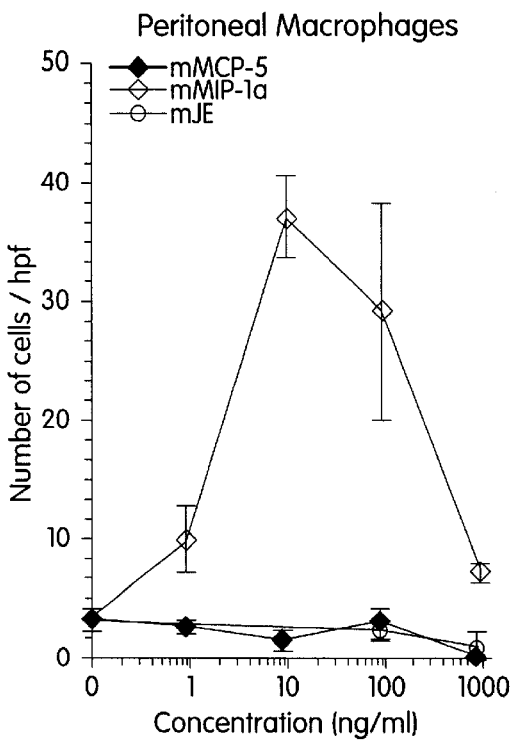
Figure 9F:
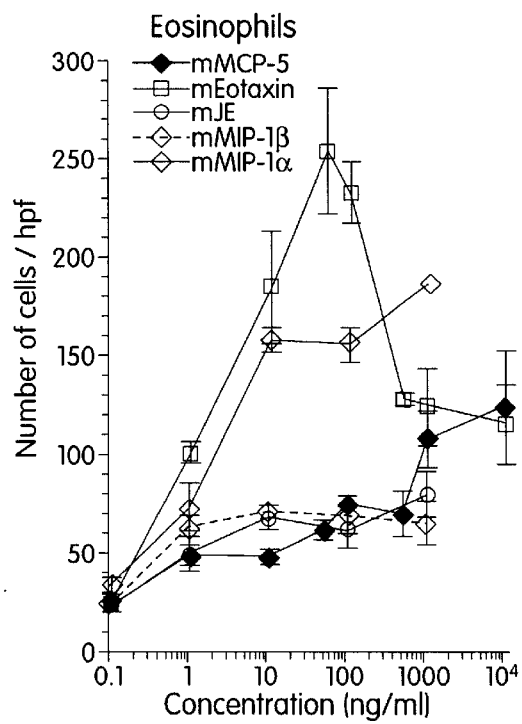
Figure 9G:
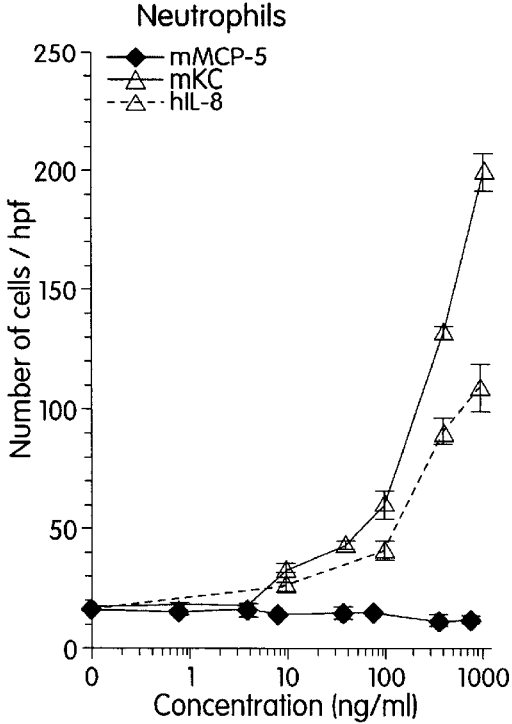

The chemotactic activity of purified recombinant MCP-5 was evaluated on human peripheral blood monocytes, mouse thioglycolate elicited peritoneal macrophages, mouse-eosinophils, and mouse neutrophils. MCP-5 was a potent chemoattractant for human peripheral blood monocytes as was mouse JE and human MCP-1 (FIG. 9D). MCP-5 had no activity on elicited mouse peritoneal macrophages, as was also absent for murine JE, although these macrophages did respond to murine MIP-1$\alpha$ as a positive control (FIG. 9E). MCP-5 had minimal activity on murine eosinophils and only at doses 1000 ng/ml, while these cells were very responsive to the positive controls, eotaxin (peak chemotaxis at 50 ng/ml 94.5 nM) and MIP-1$\alpha$, and only minimally responsive to the negative controls, JE and MIP-1$\beta$ (FIG. 9F). Murine neutrophils exhibited no response to MCP-5 but responded strongly to the control agents, mouse KC and human IL-8 (FIG. 9G). These results demonstrate that purified MCP-5 is a potent dose-dependent chemotactic agent for peripheral blood monocytes.

EXAMPLE 8

MCP-4 Induces the Release of Histamine from Basophils

A. Purification of Monocytes, Eosinophils and Neutrophils

Human mononuclear cells and granulocytes were obtained from whole peripheral blood of non-atopic and mildly atopic donors by passing the blood through a two step (1.077/1.119) Ficoll-Hypaque (Sigma Chemical Co., St. Louis, Mo.) density gradient. Monocytes were separated from the mononuclear cell layer by counter current flow elutriation using a JE-6 Beckman Centrifuge (Mason et al., Scand. J. Haematol, 34:5, 1985). The resulting monocyte fraction was estimated by examining Diff-Quick stained cytospin preparations and found to be more than 90% pure. Contaminating cells were lymphocytes. Human eosinophils were purified from the granulocyte layer by negative selection with anti-CD16-coated immunomagnetic microbeads and the MACS magnet (Hansel et al., J. Immunol. Methods 145:105–110, 1991; Miltenyi Biotech, Auburn, Calif.). The resulting eosinophil purity was more than 90%, as determined by microscopic examination of Diff-Quick-stained cytospin preparations. Contaminating cells were neutrophils.

B. Basophil Histamine Release Assays

Histamine release was determined by a modification of previously reported methods (Bischoff et al., J. Exp. Med., 172:1577–1582, 1990). The peripheral blood of mildly-atopic human donors was subjected to centrifugation over Ficoll-Paque (Pharmacia, Piscataway, N.J.) and the top layer of cells was resuspended at $3 \times 10^6$ cells/ml in HA buffer (125 mM NaCl, 5 mM KCl, 1 mM $MgCl_2$, 1 mM $CaCl_2$, 0.5 mM glucose and 0.025% BSA). Aliquots of the cells were warmed to 37° C., exposed to HA buffer alone, or to HA buffer containing either human IL-3 or human IL-5 (Genzyme) at 10 ng/ml for 10 minutes, and then challenged with-recombinant human MCP-1, MCP-3, or MCP-4 (PeproTech Inc., Rocky Hill, N.J.). After 20 minutes, the cells were centrifuged, and the supernatant was analyzed for histamine content by an enzyme-immunoassay (Immunotech, Westbrook, Me.). Histamine release was expressed as the percentage of the total content of the sample (determined after cell lysis by soinication).

In order to determine whether MCP-4 is able to stimulate histamine release from basophils, histamine release was measured from basophils that were obtained from mildly atopic donors, either as freshly isolated or primed with IL-3. MCP-4 induced histamine release from primed basophils from 2 of the 4 donors tested (Table 4). MCP-3 had a similar effect in one of the MCP-4 responsive donor tested. In contrast, MCP-1 induced histamine release from IL-3-primed basophils from all four donors.

TABLE 4

| | | Histamine Release (%) Chemokine | | | | | |
|---|---|---|---|---|---|---|---|
| | | | MC P1 | MC P3 | | MCP4 | |
| | Cytokine 10 ng/ml | None | 500 | 500 | 100 | 250 (ng/ml) | 500 |
| 1 | 0 | 3.5 | 1.0 | 4.2 | ND | 1.2 | ND |
| | IL-3 | 3.6 | 29.0 | 8.0 | ND | 2.4 | ND |
| 2 | 0 | 4.2 | 2.9 | 2.0 | ND | ND | 0.2 |
| | IL-3 | 4.1 | 77.0 | 41.0 | ND | ND | 88.0 |
| 3 | 0 | 22.0 | 27.0 | ND | 28.0 | ND | 50.0 |
| | IL-3 | 36.0 | 87.0 | ND | 77.0 | ND | 83.0 |
| 4 | 0 | 0.1 | 0.2 | ND | 0.1 | ND | 0.2 |
| | IL-3 | 0.1 | 26.0 | ND | 1.0 | ND | 4.0 |

EXAMPLE 9

Analysis of Calcium Flux

A. Calcium Flux in Mononuclear Cells in Response to MCP-4

To determine whether MCP-4 induces a calcium flux in responding leukocytes, mononuclear cells were loaded with the calcium sensitive dye fura-2 and their response to human MCP-4 was monitored with a fluorimeter. Purified cells were loaded with 5.0 mM of the acetoxymethyl ester of fura-2 (fura-2 AM; Molecular Probes, Eugene, Oreg.) for 60 minutes at 37° C. in the dark at $1 \times 10^7$/ml in DMEM supplemented with 1% heat-inactivated FBS. Loaded cells were washed twice and resuspended in a buffer containing 145 mM NaCl, 4 mM KCl, 1 mM $NaHPO_4$, 0.8 mM $MgCl_2$, 1.8 mM $CaCl_2$, 25 mM Hepes and 22 mM glucose. Two ml of cells ($2 \times 10^6$ cells/ml) were placed in a continuously stirring cuvette at 37° C. in a dual-wavelength excitation source fluorimeter (Photon Technology Inc, South Brunswick, N.J.). Changes in the level of cytosolic free calcium were determined after addition of various human chemokines by monitoring the excitation fluorescence intensity emitted at 510 nm in response to sequential excitation at 340 nm and 380 nm. The data are presented as the relative ratio of fluorescence at 340 nm and 380 nm.

Concordant with the chemotaxis data presented above, MCP-4 induced a dose-dependent calcium flux in mononuclear cells (FIG. 10A) but not in neutrophils, even though the neutrophils responded appropriately IL-8 (FIG. 10C). The half-maximal effective concentration of the MCP-4 induced monocyte calcium transient was ~35 nM, reaching saturation at ~125 nM (FIG. 10A). Rapid successive exposure to the same ligand is known to desensitize the signaling capacity of the G protein-linked receptors that are bound by chemokines. Likewise, exposure of cells to different ligands that utilize the same receptor can result in desensitization. Therefore, other chemokines, such as MCP-1, MCP-3, and RANTES, which are known to induce a calcium flux in human monocytes, were tested for the ability to cross-desensitize the MCP-4 signal. MCP-4 had no apparent effect on subsequent stimulation with either MCP-1 (FIG. 10A) or RANTES (FIG. 10B), even when a maximal initial MCP-4 stimulus was followed by a 20-fold lower MCP-1 stimulus. However, MCP-1 given first at 5 nM was able to completely desensitize the cells to a subsequent 100 nM MCP-4 stimulation (FIG. 10A). MCP-4 and MCP-3 were able to cross-desensitize each other in a dose-dependent manner (FIG. 10B), but MCP-4 and RANTES did not cross-desensitize each other (FIG. 10B).

B. Calcium Flux in Leukocytes in Response to MCP-5

Chemokines induce cell migration and activation by binding to specific G protein-coupled, seven transmembrane cell surface receptors on leukocytes. Signalling through these receptors results in a transient calcium flux. In order to determine whether MCP-5 induced a calcium flux in responding leukocytes, and thus examine the leukocyte specificity of MCP-5, purified subsets of leukocytes were loaded with the calcium sensitive dye fura 2, and their response to MCP-5 was monitored by fluorimetry.

Monocytes, macrophages, eosinophils and neutrophils were purified as follows. Peripheral blood mononuclear cells (PBMCs) were obtained from normal donors by density gradient centrifugation using 1.077 Histopaque™ (Sigma Chemical Co., St. Louis, Mo.). Murine eosinophils were isolated from the spleens of IL-5 transgenic mice by immuno-magnetic separation to remove the contaminating splenocytes, as described by Rothenberg et al., Mol. Med. 2:334–348, 1996). This process included subjecting splenocytes to hypotonic lysis in order to remove erythrocytes. The remaining leukocytes were labeled with anti-Thy-1 (M5/49), anti-B220 (6B2), or anti-Lyt-2 (53-6.7). The antibody labeled cells were treated with sheep anti-rat serum coated-magnetic microbeads, and eosinophils were enriched by negative selection through a MACS magnet (Miltenyi Biotech., Auburn, Calif.). The purity of the eosinophils was greater than 90%, according to microscopic examination of Diff-Quick-stained (Baxter Scientific, McGaw Park, Ill.) cytospin preparations. The contaminating cells were mononuclear. Macrophages were isolated from the peritoneal cavity of mice that had been treated 2 days prior with 1 ml of 2.5% Brewers thioglycollate (by intraperitoneal injection; Difco, Detroit, Calif.; Luo et al., J. Immunol. 153:4616–4624, 1994). Neutrophils were isolated from the peritoneal cavity of mice that had been treated either 4 or 18 hours previously with 1 mg of 9% sodium casein (by intraperitoneal injection; Sigma Chemical Co., St. Louis, Mo.). Macrophages and neutrophils were further purified by centrifugation in self-forming Percoll gradients. The resulting preparations were typically more than 90% pure.

Purified cells were loaded with 5.0 µM of the acetoxymethyl ester of fura-2 (fura-2 AM; Molecular Probes, Eugene, Oreg.) for 60 minutes at 37° C. in the dark at $1 \times 10^7$ cells/ml in DMEM supplemented with 1% heat-inactivated FBS. Loaded cells were washed twice and resuspended in a buffer containing 145 mM NaCl, 4 mM KCl, 1 mM $NaHPO_4$, 0.8 mM $MgCl_2$, 1.8 mM $CaCl_2$, 25 mM HEPES and 22 mM glucose. Two mls of cells ($5 \times 10^6$ cells/ml) were placed in a continuously stirring cuvette at 37° C. in a dual-wavelength excitation source fluorimeter (Photon Technology Inc., South Brunswick, N.J.). Changes in cytosolic free calcium were determined after addition of the chemokines by monitoring the excitation fluorescence intensity emitted at 150 nm in response to sequential excitation at 340 nm and 380 nm. The data are presented as the relative ratio of fluorescence at 340 and 380 nm.

MCP-5 induced a dose-dependent calcium flux in mononuclear cells (FIG. 11C) but not in eosinophils, even at 50 µg/ml or 5 µM, or in neutrophils. As controls, the purified eosinophils responded appropriately to eotaxin and MIP-1α (FIG. 11D) but did not respond to JE or MIP-1β. Furthermore purified neutrophils responded appropriately to KC and IL-8 (FIG. 11E). The half-maximal effective concentration of the MCP-5-induced mononuclear cell calcium transient was approximately 7.5 ng/ml (75 nM) and reached saturation at approximately 500 ng/ml (50 nM; FIG. 11F). These results demonstrate that MCP-5 induces a calcium flux in mononuclear cells, but not in eosinophils or neutrophils.

EXAMPLE 10

Receptor Analysis

A. CKR2b and CKR3 are MCP-4 Receptors

To determine whether MCP-4 utilizes one of the known CC chemokine receptors, a panel of HEK-293 cell lines selected for stable expression of CKRs was used to test the ability of MCP-4 to induce a calcium transient (FIG. 11A). HEK293 cells were transfected with pREP9 expression plasmids encoding CC CKR2B, CC CKR3 and CC CKR5, and a pCEP4 expression plasmid encoding CC CKR1 as previously described. Individual colonies resistant to G418 (1 mg/ml) or hygromycin (250 µg/ml) were selected and expanded. The derivation of these cell lines and their selectivity for CC chemokines other than MCP-4 have been previously reported. Cells were grown to confluence in DMEM with 10% FBS and G418 or hygromycin, harvested in PBS, loaded with 2.5 mM of fura-2 AM at 37° C. for 45 minutes, and then washed twice in PBS. Cells (at $1 \times 10^6$/ml HBSS pH 7.4) were placed in a continuously stirred cuvette at 37° C. in an MSIII fluorimeter (Photon Technology Inc., South Brunswick, N.J.). Fluorescence was monitored at excitation frequencies of 340 nm and 380 nm, and emission frequencies of 510 nm. The data were collected every 200 msec, and presented as the relative ratio of fluorescence excited at 340 nm and 380 nm.

MCP-4 at 50 nM induced a calcium flux response in the CKR2B and CKR3 transfectants, but not in the CKR1 or CKR5 transfectants. The CKR1 cell line responded to MIP-1α, RANTES, and MCP-3, and the CKR5 cell line responded to MIP-1α, MIP-1β, and RANTES, confirming expression of the corresponding receptors in these MCP-4 unresponsive targets. Both the CKR2B and CKR3 cell lines responded to MCP-4 in a concentration-dependent manner with half-maximal effective concentrations of 15 and 20 nM, respectively, and reached saturation at 100 nM in each case (FIG. 11B). The $EC_{50}$ values are ~2-fold greater than those previously defined for eotaxin at CKR3 and for MCP-1 and MCP-3 at CKR2B using the calcium flux response in the same transfectants.

Cross-desensitization experiments were also performed on the CKR2b and CKR3 cell lines. As in mononuclear cells MCP-1 desensitized the MCP-4 response in the CKR2B cell line (FIG. 12A), although MCP-4 and MCP-3 did not extinguish the MCP-1 response. MCP-3 cross-desensitized the MCP-4 response but, in contrast to mononuclear cells, MCP-4 did not cross-desensitize the MCP-3 response. Using the CKR3 cell line (FIG. 12B) we were able to demonstrate that eotaxin and MCP-4 cross-desensitized each other using the same concentration of ligand. This discrepancy has been seen with other chemokine-induced calcium transients on leukocytes vs. a cell line-expressing a cloned chemokine receptor. The mechanism of homologous and heterologous desensitization for chemokine receptors may involve both physical sequestration as well as functional inactivation by phosphorylation. The ability of each chemokine to induce these processes could differ in different cell types, even for the same receptor, and could account for the asymmetric desensitization patterns observed in primary leukocytes and receptor transfectants.

B. CCR2 is an MCP-5 Receptor

Rapid and successive exposure to the same ligand desensitizes the signalling capacity of G protein-linked receptors. Likewise, exposure of cells to different ligands that utilize the same receptor signalling pathway can also result in desensitization. Therefore, the ability of other chemokines, such as mouse JE and human MCP-1, which are known to induce a calcium flux in human monocytes, were tested for their ability to cross-desensitize the MCP-5 signal. MCP-5 at 100 nM was able to completely desensitize the cells to subsequent stimulation with a 100 mM JE or human MCP-1 (FIG. 11C). This effect was dose-dependent. When the initial dose of MCP-5 was lowered to 1 nM, the mononuclear cells were no longer desensitized to subsequent stimulation with either 100 nM JE or MCP-1. In addition, 100 nM MCP-5 completely desensitized a subsequent cellular response to a 100 nM MCP-5 challenge. In contrast, mononuclear cells initially stimulated with 100 nM JE were not desensitized to a subsequent stimulation with 100 nM MCP-5 (FIG. 11C). Initial treatment of eosinophils and neutrophils with 100 nM MCP-5 had no effect on the ability of eosinophils to respond to 10 nM eotaxin or 10 mM MIP-1α (FIG. 11D), or on the ability of neutrophils to respond to 10 nM KC (FIG. 11E). These results suggest that MCP-5 uses a receptor signalling pathway that is held in common by JE and MCP-1 and that is different from the receptor pathway utilized by MIP-1α, MIP-β, eotaxin, and KC.

The studies of receptor desensitization described above suggested that MCP-5 shares a receptor with JE and MCP-1, and the signalling studies of eosinophils suggested that MCP-5 does not signal through the two receptors known to be expressed on eosinophils, CCR3 and CCR1. In order to directly test these suggestions, a panel of HEK-293 cell lines selected for stable expression of CCRs was used to examine the ability of MCP-5 to induce calcium flux.

HEK-293 cells stably expressing human CCR2b, CCR1, and CCR3, and murine CCR2 and CCR5 with the "FLAG"

epitope at the extreme amino-terminus were prepared as described by Boring et al. (J. Biol. Chem. 271:7551–7558, 1996) and Monteclaro et al. (J. Biol. Chem. 271:19084–19092, 1996). The cells were grown in MEM with Eagle's salts supplemented with 10% fetal calf serum, 100 μg/ml penicillin, 100 μg/ml streptomycin, and 800 μg/ml G418 (Life Technologies Inc., Gaithersburg, Md.). For calcium fluorimetry, cells were grown to log phase, loaded with the calcium-specific dye indo-1 AM (Molecular Probes, Eugene, Oreg.), and assayed by spectrofluorimetry for changes in the concentration of intracellular calcium in response to addition of chemokines.

MCP-5 (100 nM) reproducibly induced a robust intracellular calcium flux in cells expressing CCR2 (FIG. 12B) but not CCR1, CCR3, or CCR5. In control experiments, functional expression of the cloned receptors in these MCP-5 unresponsive targets was confirmed: the CCR1- and CCR5-expressing cell lines responded to MIP-1α, and the CCR3-expressing line responded to eotaxin. Dose-response experiments demonstrated that MCP-5 was an excellent ligand for human CCR2b ($EC_{50}$±5 nM) as was MCP-1, and both were more potent ligands than JE (FIG. 12B (i)). Since the MCP-5 described herein is a murine protein, it was compared directly to JE for activation of the murine MCP-1 receptor, CCR2. As shown in FIG. 12B (ii), JE induced a more robust intracellular calcium flux than MCP-5 in HEK-293 cells stably expressing murine CCR2.

Desensitization studies using cells transfected with human CCR2b revealed that MCP-5 blocked subsequent responses to MCP-5, MCP-1, and JE (FIG. 12C). Similar results were obtained when the initial agonist was MCP-1 or JE (FIG. 12C). However, MCP-1 did not completely desensitize the CCR2b transfectants to subsequent MCP-5 stimulation (FIG. 12C). These data are consistent with the desensitization responses observed on human PBMCs, and with the hypothesis that MCP-5 is a full agonist for the human MCP-1 receptor (CCR2b).

Other Embodiments

The studies described herein, in which the novel chemokines MCP-4 and MCP-5 were discovered and characterized, provide the means to control the movement of inflammatory cells and, thereby, alter the immune response. For example, selectively suppressing these chemokines can be used to suppress the immune response in the event of an inflammatory condition such as asthma, atherosclerosis, arthritis, adult respiratory distress syndrome, multiple sclerosis, and glomerulonephritis. In addition, administration of MCP-4 or MCP-5, or the receptor binding domains of these proteins, may prevent infection from pathogens that utilize chemokine receptors to enter the cell. For example, the human immunodeficiency virus (HIV) is thought to be an infectious agent that uses the chemokine receptor binding mechanism. Therefore, blocking receptor binding could prevent viral entry into the cell. Conversely, administering MCP-4 or MCP-5 may enhance the immune response, e.g., in the event of an infection or tumor.

MCP-4 and MCP-5 Protein Expression

In general, the polypeptides of the invention, MCP-4 and MCP-5, can be produced by transforming suitable host cells with all or part of the corresponding cDNA in a suitable expression vehicle. Those skilled in the art of molecular biology will understand that any of a wide variety of expression systems may be used to provide the recombinant polypeptide. The precise host cell used is not critical to the invention. MCP-4 or MCP-5 polypeptides may be produced in a prokaryotic host, such as the bacterium *E. coli*, or in a eukaryotic host, such as an insect cell (e.g., Sf21 cells), or a mammalian cells (e.g., COS cells, NIH 3T3 cells, or HeLa cells). These cells are available from many sources, including the American Type Culture Collection (Rockville, Md.; see also Ausubel et al., Current Protocols in Molecular Biology, John Wiley & Sons, New York, N.Y., 1994). For a detailed description of the production of MCP-4 by *E. coli*, see Example 6 above.

The method of transduction and the expression vehicle will depend on the host system selected. Transduction methods are described by Ausubel et al. (supra), and expression vehicles may be chosen from those widely known, such as those described in Cloning Vectors: A Laboratory Manual (P. H. Pouwels et al., 1985, Supp. 1987).

A preferred expression system is the baculovirus system, in which the expression vector pBacPAK9 (Clontech, Palo Alto, Calif.) is frequently used. If desired, this system may be used in conjunction with other protein expression techniques, for example, the myc tag technique described by Evan et al., (Mol. Cell. Biol. 5:3610–3616, 1985).

Alternatively, MCP-4 or MCP-5 may be produced by stably-transfected mammalian cell lines. Numerous vectors suitable for stable transfection of mammalian cells are available to the public (see Pouwels et al., Supra). Methods for constructing stably-transfected mammalian cell lines are also publically available (e.g., in Ausubel et al., supra).

In addition to the example provided above, cDNA encoding all or part of the MCP-4 or MCP-5 polypeptide can be cloned into an expression vector, such as pCVSEII-DHFR or pAdD26SV(A), which includes the dihydrofolate reductase (DHFR) gene. Integration of the plasmid containing the MCP-4- or MCP-5-encoding gene into the host cell chromosome is selected for by inclusion of 0.01-300 μM methotrexate in the cell culture medium (as described in Ausubel et al., supra). This type of selection can be accomplished in most cell types. Preferably, the cells will be DHFR-deficient, such as CHO DHFR cells (A.T.C.C. Accession No. CRL 9096). Recombinant protein expression can be increased by DHFR-mediated amplification of the transfected gene. Methods for selecting cell lines bearing gene amplifications, which generally involve extended cell culture in medium containing increasing levels of methotrexate, are described in Ausubel et al. (supra).

Alternatively, the proteins of the invention, particularly fragments thereof, can be produced by chemical synthesis (e.g., using the methods described in Solid Phase Peptide Synthesis, Second Edition, The Pierce Chemical Company, Rockford, Ill., 1984).

Once the recombinant MCP-4 or MCP-5 proteins are expressed, they can be isolated by standard biochemical techniques, such as affinity chromatography, and purified further, e.g., by high performance liquid chromatography (see, e.g., Fisher, Laboratory Techniques in Biochemistry and Molecular Biology, Eds., Work and Burdon, Elsevier, 1980).

As described above, MCP-4 has an N-terminal glutamine residue, as does MCP-1, MCP-2, and MCP-3. The biological activity of the expressed polypeptide may be substantially reduced either by addition of one or more amino acids prior to the N-terminal glutamine, or the deletion of one or more N-terminal residues. Addition of such amino acids may be particularly desirable for generating antiviral and anti-inflammatory polypeptide compounds. Such mutants may be produced by standard methods of genetic engineering and used to suppress the immune response or block pathogen entry via chemokine receptors.

It is likely that, when administered in excess, the N-terminal mutant MCP-4 or MCP-5 polypeptide will suppress the immune response by effectively competing for the limited number of cell surface receptors, thereby blocking the response of these cells to the wild-type chemokine signals. As discussed below, the gene encoding such mutant polypeptides can also be administered.

Generation of Anti-MCP-4 or Anti-MCP-5 Antibodies

In order to generate MCP-4 or MCP-5-specific antibodies, the full-length MCP-4 or MCP-5 coding sequences or portions thereof can be expressed as C-terminal fusion molecules with glutathione S-transferase (GST; Smith et al., Gene 67:31–40, 1988). The coding sequence may encode either the full-length proteins, or fragments of these proteins that are likely to be antigenic, such as fragments that lie outside highly conserved regions or that contain a high proportion of charged residues. The fusion protein, which should conform to a predicted size, can then be purified with glutathione-Sepharose beads, eluted with glutathione, cleaved with thrombin (at an engineered cleavage site), and purified to the degree necessary for immunization of rabbits. Primary immunizations are typically carried out the Freund's complete adjuvant and subsequent immunizations with Freund's incomplete adjuvant. Antibody titres are monitored by Western blot and immunoprecipitation analyses using the thrombin-cleaved MCP-4 or MCP-5 protein fragment of the GST-MCP-4 or GST-MCP-5 fusion protein. Immune sera are affinity purified using CNBr-Sepharose-coupled MCP-4 or MCP-5 proteins. The specificity of the antiserum can be determined using a panel of unrelated GST fusion proteins (such as GST-p53, and GST-Rb) and GST-trypsin (which may be generated by PCR using published sequences).

As an alternate or adjunct immunogen, peptides corresponding to relatively unique regions of MCP-4 or MCP-5 (i.e. peptides that can be used to generate antibodies that specifically bind MCP-4 or MCP-5) may be generated and coupled to keyhole limpet hemocyanin (KLH) through an introduced C-terminal lysine. Antiserum to each of these peptides is then similarly affinity purified on peptides conjugated to BSA, and specificity is tested by ELISA and Western blot analysis using peptide conjugates.

Alternatively, monoclonal antibodies may be prepared using the MCP-4 and MCP-5 proteins described herein and standard hybridoma technology (see, e.g., Kohler et al., Nature 256:495, 1975; Kohler et al., Eur. J. Immunol. 6:511, 1976; Kohler et al., Eur. J. Immunol. 6:292, 1976; Hammerline et al., In Monoclonal Antibodies and T Cell Hybridomas, Elsevier, New York, N.Y., 1981). Once produced, monoclonal antibodies can be tested for their ability to specifically bind MCP-4 or MCP-5, as appropriate, by Western blot or immunoprecipitation analyses. Antibodies that specifically recognize MCP-4 or MCP-5 are considered useful in the invention; antibodies that can block the activity of MCP-4 or MCP-5 would be useful as agents to specifically block the accumulation of leukocytes (particularly monocytes) in unwanted instances of inflammation.

Generation of Transgenic Animals

Methods for generating transgenic animals, which incorporate an exogenous DNA molecule into their genome and pass it to their offspring, are well known to skilled artisans. Typically, the exogenous DNA is introduced into single-celled embryos that are obtained by mating male and female mice from a defined inbred genetic background (Brinster et al., Proc. Natl. Acad. Sci. USA 82:4438–4442, 1985). If the mating is successful, the female mouse is sacrificed and the fertilized eggs are removed from the reproductive system. At this time, pronuclei are visible under the light microscope. Exogenous DNA, such as the MCP-4 or MCP-5 cDNA disclosed herein, is then introduced into the egg. Typically, the DNA is microinjected into a pronucleus, but other methods of transfection may also be used. A number of the microinjected eggs are then implanted into a pseudopregnant female mouse (pseudopregnancy is achieved by mating a normal female mouse with a vasectomized male mouse). These eggs will develop for the fill period of gestation. The surrogate mother delivers the mice that develop from these eggs, which are then tested (when they are approximately 4 weeks old) for the presence of the exogenous DNA.

Identification and Administration of Compounds that Modulate Expression of MCP-4 and/or MCP-5

Isolation of the MCP-4 and MCP-5 cDNAs also facilitates the identification of molecules that increase or decrease the expression of these genes in vivo. Many quantitative assays for gene expression are known and may be utilized in this aspect of the invention. A few examples are provided below.

In order to identify molecules that modulate MCP-4 or MCP-5 gene expression, candidates are added at varying concentrations to the culture medium of cells expressing either MCP-4 or MCP-5 mRNA. MCP-4 or MCP-5 expression is then measured, for example, by Northern blot analysis using MCP-4 or MCP-5 cDNA hybridization probes. The level of MCP-4 or MCP-5 expression in the presence of the candidate molecule is compared with that measured in its absence.

Alternatively, the effect of the candidate molecule may be assessed at the level of translation by measuring the level of MCP-4 or MCP-5 protein, for example, by Western blot analysis or immunoprecipitation with an MCP-4 or MCP-5-specific antibody.

If the modulatory compound is an inhibitory compound, it may function by competing with MCP-4 or MCP-5 for the limited number of chemokine receptors on the cell surface. These compounds may be identified by, for example, examining the binding of MCP-4 or MCP-5 to their respective receptors in the presence and absence of the candidate compound. A compound that blocks chemokine receptors may be especially useful as an antiviral agent because some viruses, including the human immunodeficiency virus that causes AIDS, gain entry to the cell via chemokine receptors.

Candidate modulators may be purified, substantially purified, or may remain as one component of a mixture of compounds (e.g., as an extract or a supernatant obtained from a cell culture). In an assay of mixed compounds, MCP-4 or MCP-5 expression can be tested against progressively smaller subsets of the candidate compound pool. These subsets may be produced, e.g., by standard purification techniques such as HPLC or FPLC, until a single compound or a minimal group of compounds is demonstrated to modulate the expression of MCP-4 and/or MCP-5.

Alternatively, or in addition, candidate modulatory compounds may be screened for those which modulate the chemotaxis of, e.g., monocytes, toward MCP-4 or MCP-5 producing cells. In this approach, chemotactic activity is simply compared in any standard assay of chemotaxis (including those described herein), under otherwise equivalent conditions, in the presence and absence of the candidate compound. Candidate modulatory compounds include peptide and non-peptide molecules, such as those found in cell extracts, mammalian serum, growth medium in which mammalian cells have been grown, or synthetic compounds.

Particularly useful modulators of MCP-4 or MCP-5 expression include tumor necrosis factor-α, interleukin-1, interleukin-4, and interferon-gamma.

A molecule that decreases MCP-4 or MCP-5 expression or MCP-4 or MCP-5 chemotactic activity is considered particularly useful in the invention. This molecule may be used, for example, as a therapeutic to decrease the cellular levels of MCP-4 or MCP-5 expression, and thereby decrease the symptoms associated with MCP-4 or MCP-5 expression, including asthmatic reaction, chronic obstructive pulmonary diseases, bronchiectasis, cystic fibrosis, and inflammatory bowel diseases (i.e., Crohn's Disease and ulcerative colitis). Compounds that alleviate the inflammation associated with sinusitis are of particular interest. Infections, such as parasitic infections may also be treated with a molecule that inhibits MCP-4 or MCP-5 expression.

Conversely, a molecule that enhances MCP-4 or MCP-5 expression may be used in the treatment of cancer. As described below, enhanced leukocyte chemotaxis to the site of the tumor is desirable.

Modulatory compounds may be administered with a pharmaceutically-acceptable diluent, carrier, or excipient, according to conventional pharmaceutical practice. Any appropriate route of administration may be employed. For example, administration can be parenteral, intravenous, subcutaneous, intramuscular, intracranial, intraorbital, opthalmic, intraventricular, intracapsular, intraspinal, intracistermal, intraperitoneal, transmucosal, or oral. The modulatory compound can be formulated in various ways, according to the corresponding route of administration. For example liquid solutions can be made for ingestion or injection; gels or powders can be made for ingestion, inhalation, or topical application. Methods for making such formulations are well known and can be found in, for example, "Remington's Pharmaceutical Sciences."

MCP-4 or MCP-5-based Therapies

To enhance, for example, the infiltration of leukocytes into a tumor, a functional MCP-4 or MCP-5 gene or polypeptide may be administered to the patient.

Retroviral vectors, adenoviral vectors, adeno-associated viral vectors, and other viral vectors with the appropriate tropism may be used as a gene transfer delivery system for a therapeutic eotaxin gene construct. Suitable vectors are generally known (see, e.g., Miller, Human Gene Therapy 15:14, 1990; Firedman, Science 244:1275–1281, 1989; Eglitis et al., BioTechniques 6:608–614, 1988; Tolstoshev et al., current Opinion in biotechnology 1:55–61, 1990). Retroviruses are particularly well developed and have been used in clinical settings (Rosenberg et al., N. Engl. J. Med 323:370, 1990; Anderson et al., U.S. Pat. No. 5,399,346).

Gene therapies that are not mediated by viral vectors may also be employed. For example, nucleic acid molecules encoding all or part of MCP-4 or MCP-5 may be encapsulated in liposomes and administered by lipofection (Felgner et al., Proc. Natl. Acad. Sci. USA 84:7413, 1987; Ono et al., Neuroscience Lett. 117:259, 1990; Brigham et al., Am. J. Med. Sci. 298:278, 1989; Staubinger and Papahadjopoulos, Meth. Enzymol. 101:512, 1983). Alternatively, the cells may be transfected by application of the nucleic acid molecules conjugated with asialorosonucoid-polylysine (Wu et al., J. Biol. Chem. 263:14621, 1988; Wu et al., J. Biol. Chem. 264:16985, 1989). Alternatively, MCP-4 or MCP-5 mRNA may be administered directly. The mRNA can be produced by any standard technique, but is most readily produced by in vitro transcription using an MCP-4 or MCP-5 cDNA under the control of a high efficiency promoter (e.g., the T7 promoter).

Preferably, the therapeutic MCP-4 or MCP-5 DNA construct is applied to the site of the malignancy or inflammation, to the tissue in the larger vicinity of a malignancy or inflammation, or to the blood vessels supplying these areas. The DNA construct administered may contain any suitable promoter, from which MCP-4 or MCP-5 gene expression is directed. Examples of such promoters include the human cytomegalovirus promoter, the simian virus 40 promoter, and the metallothionein promoter. Alternatively, the promoter may be cell type-specific. For example, the tyrosine hydroxylase promoter may be used to direct gene expression within catecholinergic neurons.

Ideally, the production of MCP-4 or MCP-5 by any gene therapy approach described herein will result in a cellular level of MCP-4 or MCP-5 expression that is at least equivalent to the normal, cellular level of expression of these genes. Skilled artisans will recognize that these therapies may be used in combination with more traditional therapies, such as surgery, radiotherapy, or chemotherapy.

SEQUENCE LISTING (1) GENERAL INFORMATION:

(iii) NUMBER OF SEQUENCES: 30

(2) INFORMATION FOR SEQ ID NO: 1:

(i) SEQUENCE CHARACTERISTICS:
      (A) LENGTH: 823 base pairs
      (B) TYPE: nucleic acid
      (C) STRANDEDNESS: single
      (D) TOPOLOGY: linear (ii) MOLECULE TYPE: Other (xi) SEQUENCE DESCRIPTION: SEQ ID NO: 1:

```
AACATTGTGA AATCTCCAAC TCTTAACCTT CAACATGAAA GTCTCTGCAG TGCTTCTGTG      60

CCTGCTGCTC ATGACAGCAG CTTTCAACCC CCAGGGACTT GCTCAGCCAG ATGCACTCAA     120
```

-continued

```
CGTCCCATCT ACTTGCTGCT TCACATTTAG CAGTAAGAAG ATCTCCTTGC AGAGGCTGAA    180

GAGCTATGTG ATCACCACCA GCAGGTGTCC CCAGAAGGCT GTCATCTTCA GAACCAAACT    240

GGGCAAGGAG ATCTGTGCTG ACCCAAAGGA GAAGTGGGTC CAGAATTATA TGAAACACCT    300

GGGCCGGAAA GCTCACACCC TGAAGACTTG AACTCTGCTA CCCCTACTGA AATCAAGCTG    360

GAGTACGTGA AATGACTTTT CCATTCTCCT CTGGCCTCCT CTTCTATGCT TTGGAATACT    420

TCTACCATAA TTTTCAAATA GGATGCATTC GGTTTTGTGA TTCAAAATGT ACTATGTGTT    480

AAGTAATATT GGCTATTATT TGACTTGTTG CTGGTTTGGA GTTTATTTGA GTATTGCTGA    540

TCTTTTCTAA AGCAAGGCCT TGAGCAAGTA GGTTGCTGTC TCTAAGCCCC CTTCCCTTCC    600

ACTATGAGCT GCTGGCAGTG GGTTTGTATT CGGTTCCCAG GGGTTGAGAG CATGCCTGTG    660

GGAGTCATGG ACATGAAGGG ATGCTGCAAT GTAGGAAGGA GAGCTCTTTG TGAATGTGAG    720

GTGTTGCTAA ATATGTTATT GTGGAAAGAT GAATGCAATA GTAGGACTGC TGACATTTTG    780

CAGAAAATAC ATTTTATTTA AAATCTCCTA AAAAAAAAAA AAA                      823
```

(2) INFORMATION FOR SEQ ID NO: 2:

(i) SEQUENCE CHARACTERISTICS:
        (A) LENGTH: 98 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO: 2:

```
Met Lys Val Ser Ala Val Leu Leu Cys Leu Leu Leu Met Thr Ala Ala
 1               5                  10                  15

Phe Asn Pro Gln Gly Leu Ala Gln Pro Asp Ala Leu Asn Val Pro Ser
                20                  25                  30

Thr Cys Cys Phe Thr Phe Ser Ser Lys Lys Ile Ser Leu Gln Arg Leu
            35                  40                  45

Lys Ser Tyr Val Ile Thr Thr Ser Arg Cys Pro Gln Lys Ala Val Ile
 50                  55                  60

Phe Arg Thr Lys Leu Gly Lys Glu Ile Cys Ala Asp Pro Lys Glu Lys
65                  70                  75                  80

Trp Val Gln Asn Tyr Met Lys His Leu Gly Arg Lys Ala His Thr Leu
                85                  90                  95

Lys Thr
```

(2) INFORMATION FOR SEQ ID NO: 3:

(i) SEQUENCE CHARACTERISTICS:
        (A) LENGTH: 514 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 3:

```
CTAGCTTTCA TTTCGAAGTC TTTGACCTCA ACATGAAGAT TCCACACTT CTATGCCTCC     60

TGCTCATAGC TACCACCATC AGTCCTCAGG TATTGGCTGG ACCAGATGCG GTGAGCACCC    120

CAGTCACGTG CTGTTATAAT GTTGTTAAGC AGAAGATTCA CGTCCGGAAG CTGAAGAGCT    180

ACAGGAGAAT CACAAGCAGC CAGTGTCCCC GGGAAGCTGT GATCTTCAGG ACCATACTGG    240
```

```
ATAAGGAGAT CTGTGCTGAC CCCAAGGAGA AGTGGGTTAA GAATTCCATA AACCACTTGG      300

ATAAGACGTC TCAAACCTTC ATCCTTGAAC CTTCATGTCT AGGCTGAGAG TTCCAAAAAC      360

TCTTACGTAT TTCCCCCTGA AGTTCCCCAC GGGCAGTGTG ATATTTATTA TGATATCTAA      420

AAAGAGATGT TTTTAATAAT TTAAACAAAC TTGCTTAAAT AATATTTAAT GGTATTTAAG      480

TAATATTTGG GCCAATTAAA CCGAATCTAA TTTA                                 514
```

(2) INFORMATION FOR SEQ ID NO: 4:

(i) SEQUENCE CHARACTERISTICS:
        (A) LENGTH: 104 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO: 4:

```
Met Lys Ile Ser Thr Leu Leu Cys Leu Leu Leu Ile Ala Thr Thr Ile
 1               5                  10                  15

Ser Pro Gln Val Leu Ala Gly Pro Asp Ala Val Ser Thr Pro Val Thr
                20                  25                  30

Cys Cys Tyr Asn Val Val Lys Gln Lys Ile His Val Arg Lys Leu Lys
            35                  40                  45

Ser Tyr Arg Arg Ile Thr Ser Ser Gln Cys Pro Arg Glu Ala Val Ile
    50                  55                  60

Phe Arg Thr Ile Leu Asp Lys Glu Ile Cys Ala Asp Pro Lys Glu Lys
65                  70                  75                  80

Trp Val Lys Asn Ser Ile Asn His Leu Asp Lys Thr Ser Gln Thr Phe
                85                  90                  95

Ile Leu Glu Pro Ser Cys Leu Gly
            100
```

(2) INFORMATION FOR SEQ ID NO: 5:

(i) SEQUENCE CHARACTERISTICS:
        (A) LENGTH: 99 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO: 5:

```
Met Lys Val Ser Ala Ala Leu Leu Cys Leu Leu Leu Ile Ala Ala Thr
 1               5                  10                  15

Phe Ile Pro Gln Gly Leu Ala Gln Pro Asp Ala Ile Asn Ala Pro Val
                20                  25                  30

Thr Cys Cys Tyr Asn Phe Thr Asn Arg Lys Ile Ser Val Gln Arg Leu
            35                  40                  45

Ala Ser Tyr Arg Arg Ile Thr Ser Ser Lys Cys Pro Lys Glu Ala Val
    50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr
```

(2) INFORMATION FOR SEQ ID NO: 6:

(i) SEQUENCE CHARACTERISTICS:
     (A) LENGTH: 77 amino acids
     (B) TYPE: amino acid
     (C) STRANDEDNESS: unknown
     (D) TOPOLOGY: linear (ii) MOLECULE TYPE: protein (xi) SEQUENCE DESCRIPTION: SEQ ID NO: 6:

Ala Gln Pro Asp Ser Val Ser Ile Pro Ile Thr Cys Cys Phe Asn Val
1               5                   10                  15

Ile Asn Arg Lys Ile Pro Ile Gln Arg Leu Glu Ser Tyr Thr Arg Ile
            20                  25                  30

Thr Asn Ile Gln Cys Pro Lys Glu Ala Val Ile Phe Lys Thr Lys Arg
        35                  40                  45

Gly Lys Glu Val Cys Ala Asp Pro Lys Glu Arg Trp Val Arg Asp Ser
    50                  55                  60

Met Lys His Leu Asp Gln Ile Phe Gln Asn Leu Lys Pro
65                  70                  75

(2) INFORMATION FOR SEQ ID NO: 7:

(i) SEQUENCE CHARACTERISTICS:
          (A) LENGTH: 99 amino acids
          (B) TYPE: amino acid
          (C) STRANDEDNESS: unknown
          (D) TOPOLOGY: linear (ii) MOLECULE TYPE: protein (xi) SEQUENCE DESCRIPTION: SEQ ID NO: 7:

Met Lys Ala Ser Ala Ala Leu Leu Cys Leu Leu Thr Ala Ala Ala
1               5                   10                  15

Phe Ser Pro Gln Gly Leu Ala Gln Pro Val Gly Ile Asn Thr Ser Thr
            20                  25                  30

Thr Cys Cys Tyr Arg Phe Ile Asn Lys Lys Ile Pro Lys Gln Arg Leu
        35                  40                  45

Glu Ser Tyr Arg Arg Thr Thr Ser Ser His Cys Pro Arg Glu Ala Val
    50                  55                  60

Ile Phe Lys Thr Lys Leu Asp Lys Glu Ile Cys Ala Asp Pro Thr Gln
65                  70                  75                  80

Lys Trp Val Gln Asp Phe Met Lys His Leu Asp Lys Lys Thr Gln Thr
            85                  90                  95

Pro Lys Leu (2) INFORMATION FOR SEQ ID NO: 8:

(i) SEQUENCE CHARACTERISTICS:
          (A) LENGTH: 97 amino acids
          (B) TYPE: amino acid
          (C) STRANDEDNESS: unknown
          (D) TOPOLOGY: linear (ii) MOLECULE TYPE: protein (xi) SEQUENCE DESCRIPTION: SEQ ID NO: 8:

Met Lys Val Ser Ala Ala Leu Leu Trp Leu Leu Leu Ile Ala Ala Ala
1               5                   10                  15

Phe Ser Pro Gln Gly Leu Ala Gly Pro Ala Ser Val Pro Thr Thr Cys
            20                  25                  30

Cys Phe Asn Leu Ala Asn Arg Lys Ile Pro Leu Gln Arg Leu Glu Ser

```
                35                  40                  45
Tyr Arg Arg Ile Thr Ser Gly Lys Cys Pro Gln Lys Ala Val Ile Phe
    50                  55                  60

Lys Thr Lys Leu Ala Lys Asp Ile Cys Ala Asp Pro Lys Lys Lys Trp
65                  70                  75                  80

Val Gln Asp Ser Met Lys Tyr Leu Asp Gln Lys Ser Pro Thr Pro Lys
                85                  90                  95

Pro
```

(2) INFORMATION FOR SEQ ID NO: 9:

(i) SEQUENCE CHARACTERISTICS:
        (A) LENGTH: 93 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO: 9:

```
Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
                20                  25                  30

Ala Cys Cys Phe Ser Tyr Thr Ser Arg Gln Ile Pro Gln Asn Phe Ile
                35                  40                  45

Ala Asp Tyr Phe Glu Thr Ser Ser Gln Cys Ser Lys Pro Ser Val Ile
    50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala
                85                  90
```

(2) INFORMATION FOR SEQ ID NO: 10:

(i) SEQUENCE CHARACTERISTICS:
        (A) LENGTH: 92 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO: 10:

```
Met Lys Leu Cys Val Thr Val Leu Ser Leu Leu Met Leu Val Ala Ala
1               5                   10                  15

Phe Cys Ser Pro Ala Leu Ser Ala Pro Met Gly Ser Asp Pro Pro Thr
                20                  25                  30

Ala Cys Cys Phe Ser Tyr Thr Ala Arg Lys Leu Pro Arg Asn Phe Val
                35                  40                  45

Val Asp Tyr Tyr Glu Thr Ser Ser Leu Cys Ser Gln Pro Ala Val Val
    50                  55                  60

Phe Gln Thr Lys Arg Ser Lys Gln Val Cys Ala Asp Pro Ser Glu Ser
65                  70                  75                  80

Trp Val Gln Glu Tyr Val Tyr Asp Leu Glu Leu Asn
                85                  90
```

(2) INFORMATION FOR SEQ ID NO: 11:

(i) SEQUENCE CHARACTERISTICS:

(A) LENGTH: 84 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO: 11:

Met Lys Val Ser Ala Ala Arg Leu Ala Val Ile Leu Ile Ala Thr Ala
1               5                   10                  15

Leu Cys Ala Pro Ala Ser Ala Ser Pro Tyr Ser Ser Asp Thr Thr Pro
            20                  25                  30

Cys Cys Phe Ala Tyr Ile Ala Arg Pro Leu Pro Arg Ala His Ile Lys
        35                  40                  45

Glu Tyr Phe Tyr Thr Ser Gly Lys Cys Ser Asn Pro Ala Val Val Phe
    50                  55                  60

Val Thr Arg Lys Asn Arg Gln Val Cys Ala Asn Pro Glu Lys Lys Trp
65                  70                  75                  80

Val Arg Met Ser (2) INFORMATION FOR SEQ ID NO: 12:

(i) SEQUENCE CHARACTERISTICS:
        (A) LENGTH: 148 amino acids
        (B) TYPE: amino acid
        (C) STRANDEDNESS: unknown
        (D) TOPOLOGY: linear (ii) MOLECULE TYPE: protein (v) FRAGMENT TYPE: N-terminal (xi) SEQUENCE DESCRIPTION: SEQ ID NO: 12:

Met Gln Val Pro Val Met Leu Leu Gly Leu Leu Phe Thr Val Ala Gly
1               5                   10                  15

Trp Ser Ile His Val Leu Ala Gln Pro Asp Ala Val Asn Ala Pro Leu
            20                  25                  30

Thr Cys Cys Tyr Ser Phe Thr Ser Lys Met Ile Pro Met Ser Arg Leu
        35                  40                  45

Glu Ser Tyr Lys Arg Ile Thr Ser Ser Arg Cys Pro Lys Glu Ala Val
    50                  55                  60

Val Phe Val Thr Lys Leu Lys Arg Glu Val Cys Ala Asp Pro Lys Lys
65                  70                  75                  80

Glu Trp Val Gln Thr Tyr Ile Lys Asn Leu Asp Arg Asn Gln Met Arg
                85                  90                  95

Ser Glu Pro Thr Thr Leu Phe Lys Thr Ala Ser Ala Leu Arg Ser Ser
            100                 105                 110

Ala Pro Leu Asn Val Lys Leu Thr Arg Lys Ser Glu Ala Asn Ala Ser
        115                 120                 125

Thr Thr Phe Ser Thr Thr Thr Ser Ser Thr Ser Val Gly Val Thr Ser
    130                 135                 140

Val Thr Val Asn
145

(2) INFORMATION FOR SEQ ID NO: 13:

(i) SEQUENCE CHARACTERISTICS:
        (A) LENGTH: 97 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO: 13:

```
Met Arg Ile Ser Ala Thr Leu Leu Cys Leu Leu Ile Ala Ala Ala
 1               5                  10                  15

Phe Ser Ile Gln Val Trp Ala Gln Pro Asp Gly Pro Asn Ala Ser Thr
                20                  25                  30

Cys Cys Tyr Val Lys Lys Gln Lys Ile Pro Lys Arg Asn Leu Lys Ser
            35                  40                  45

Tyr Arg Arg Ile Thr Ser Ser Arg Cys Pro Trp Glu Ala Val Ile Phe
50                      55                  60

Lys Thr Lys Lys Gly Met Glu Val Cys Ala Glu Ala His Gln Lys Trp
65                  70                  75                  80

Val Glu Glu Ala Ile Ala Tyr Leu Asp Met Lys Thr Pro Thr Pro Lys
                85                  90                  95

Pro
```

(2) INFORMATION FOR SEQ ID NO: 14:

(i) SEQUENCE CHARACTERISTICS:
        (A) LENGTH: 97 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO: 14:

```
Met Gln Ser Ser Thr Ala Leu Leu Phe Leu Leu Leu Thr Val Thr Ser
 1               5                  10                  15

Phe Thr Ser Gly Val Leu Ala His Pro Gly Ser Ile Pro Thr Ser Cys
                20                  25                  30

Cys Phe Ile Met Thr Ser Lys Lys Ile Pro Asn Thr Leu Leu Lys Ser
            35                  40                  45

Tyr Lys Arg Ile Thr Asn Asn Arg Cys Thr Leu Lys Ala Ile Val Phe
50                      55                  60

Lys Thr Arg Leu Gly Lys Glu Ile Cys Ala Asp Pro Lys Lys Lys Trp
65                  70                  75                  80

Val Gln Asp Ala Thr Lys His Leu Asp Gln Lys Leu Gln Thr Pro Lys
                85                  90                  95

Pro
```

(2) INFORMATION FOR SEQ ID NO: 15:

(i) SEQUENCE CHARACTERISTICS:
        (A) LENGTH: 148 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO: 15:

```
Met Gln Val Pro Val Met Leu Leu Gly Leu Leu Phe Thr Val Ala Gly
 1               5                  10                  15

Trp Ser Ile His Val Leu Ala Gln Pro Asp Ala Val Asn Ala Pro Leu
                20                  25                  30

Thr Cys Cys Tyr Ser Phe Thr Ser Lys Met Ile Pro Met Ser Arg Leu
            35                  40                  45
```

```
Glu Ser Tyr Lys Arg Ile Thr Ser Ser Arg Cys Pro Lys Glu Ala Val
 50                  55                  60
Val Phe Val Thr Lys Leu Lys Arg Glu Val Cys Ala Asp Pro Lys Lys
 65                  70                  75                  80
Glu Trp Val Gln Thr Tyr Ile Lys Asn Leu Asp Arg Asn Gln Met Arg
                 85                  90                  95
Ser Glu Pro Thr Thr Leu Phe Lys Thr Ala Ser Ala Leu Arg Ser Ser
                100                 105                 110
Ala Pro Leu Asn Val Lys Leu Thr Arg Lys Ser Glu Ala Asn Ala Ser
            115                 120                 125
Thr Thr Phe Ser Thr Thr Thr Ser Ser Thr Ser Val Gly Val Thr Ser
            130                 135                 140
Val Thr Val Asn
145
```

(2) INFORMATION FOR SEQ ID NO: 16:

(i) SEQUENCE CHARACTERISTICS:
        (A) LENGTH: 97 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO: 16:

```
Met Arg Ile Ser Ala Thr Leu Leu Cys Leu Leu Leu Ile Ala Ala Ala
 1               5                  10                  15
Phe Ser Ile Gln Val Trp Ala Gln Pro Asp Gly Pro Asn Ala Ser Thr
                 20                  25                  30
Cys Cys Tyr Val Lys Lys Gln Lys Ile Pro Lys Arg Asn Leu Lys Ser
            35                  40                  45
Tyr Arg Arg Ile Thr Ser Ser Arg Cys Pro Trp Glu Ala Val Ile Phe
 50                  55                  60
Lys Thr Lys Lys Gly Met Glu Val Cys Ala Glu Ala His Gln Lys Trp
 65                  70                  75                  80
Val Glu Glu Ala Ile Ala Tyr Leu Asp Met Lys Thr Pro Thr Pro Lys
                 85                  90                  95
Pro
```

(2) INFORMATION FOR SEQ ID NO: 17:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 17:

CTTCTGKGYC TGCTGYTCA                                        19

(2) INFORMATION FOR SEQ ID NO: 18:

(i) SEQUENCE CHARACTERISTICS:
        (A) LENGTH: 17 base pairs
        (B) TYPE: nucleic acid
        (C) STRANDEDNESS: single
        (D) TOPOLOGY: linear

```
    (ii) MOLECULE TYPE: Other (xi) SEQUENCE DESCRIPTION: SEQ ID NO: 18:

ACAGCYTYYY DGGGACA                                                      17

(2) INFORMATION FOR SEQ ID NO: 19:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 19:

TGTCCCHRRR ARGCTGT                                                      17

(2) INFORMATION FOR SEQ ID NO: 20:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 20:

GSKTCAGCRC AGAYYTC                                                      17

(2) INFORMATION FOR SEQ ID NO: 21:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 21:

CTGGCTGCTT GTGATTCTCC TGT                                               23

(2) INFORMATION FOR SEQ ID NO: 22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 22:

CAGTCCTCAG GTATTGGCTG G                                                 21

(2) INFORMATION FOR SEQ ID NO: 23:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 23:
```

```
AGCTTTCATT TCGAAGTCTT TG                                            22
```

(2) INFORMATION FOR SEQ ID NO: 24:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 24:

```
TAGATTCGGT TTAATTGGCC C                                             21
```

(2) INFORMATION FOR SEQ ID NO: 25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 25:

```
TCAGCCAGAT GCACTCAACG                                               20
```

(2) INFORMATION FOR SEQ ID NO: 26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 26:

```
TGGAAAAGTC ATTTCACGTA                                               20
```

(2) INFORMATION FOR SEQ ID NO: 27:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 27:

```
TTACAGGTCA GGTCCCCTAC T                                             21
```

(2) INFORMATION FOR SEQ ID NO: 28:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 28:

```
CTCCTTATCC AGTATGGTCC TG                                            22
```

(2) INFORMATION FOR SEQ ID NO: 29:

```
        (i) SEQUENCE CHARACTERISTICS:
            (A) LENGTH: 89 amino acids
            (B) TYPE: amino acid
            (C) STRANDEDNESS: unknown
            (D) TOPOLOGY: unknown (ii) MOLECULE TYPE: protein (xi) SEQUENCE DESCRIPTION: SEQ ID NO: 29:

Met Arg Gly Ser His His His His His His Ile Glu Gly Arg Gln Pro
 1               5                  10                  15

Asp Ala Leu Asn Val Pro Ser Thr Cys Cys Phe Thr Phe Ser Ser Lys
                20                  25                  30

Lys Ile Ser Leu Gln Arg Leu Lys Ser Tyr Val Ile Thr Thr Ser Arg
            35                  40                  45

Cys Pro Gln Lys Ala Val Ile Phe Arg Thr Lys Leu Gly Lys Glu Ile
        50                  55                  60

Cys Ala Asp Pro Lys Glu Lys Trp Val Gln Asn Tyr Met Lys His Leu
65                  70                  75                  80

Gly Arg Lys Ala His Thr Leu Lys Thr
                85

(2) INFORMATION FOR SEQ ID NO: 30:

(i) SEQUENCE CHARACTERISTICS:
            (A) LENGTH: 10 amino acids
            (B) TYPE: amino acid
            (C) STRANDEDNESS: unknown
            (D) TOPOLOGY: unknown (ii) MOLECULE TYPE: protein (xi) SEQUENCE DESCRIPTION: SEQ ID NO: 30:

Gly Ser Asp Tyr Lys Asp Asp Asp Asp Lys
 1               5                  10
```

Additional embodiments are within the following claims.

What is claimed is:

1. A substantially pure nucleic acid molecule comprising nucleotides 35–331 of SEQ ID NO: 1, wherein said nucleic acid molecule encodes a monocyte chemotactic protein (MCP)-4 polypeptide.

2. The nucleic acid molecule of claim 1, wherein said molecule is operably linked to a regulatory sequence comprising a promoter.

3. A vector comprising the nucleic acid molecule of claim 1.

4. A cell comprising the vector of claim 3.

* * * * *